US010647755B2

(12) United States Patent
Sun et al.

(10) Patent No.: US 10,647,755 B2
(45) Date of Patent: May 12, 2020

(54) PHOTORESPONSIVE PROTEIN HYDROGELS AND METHODS AND USES THEREOF

(71) Applicant: THE HONG KONG UNIVERSITY OF SCIENCE AND TECHNOLOGY, Kowloon (HK)

(72) Inventors: Fei Sun, Kowloon (HK); Ri Wang, Sai Kung (HK)

(73) Assignee: The Hong Kong University of Science and Technology, Kowloon (HK)

( * ) Notice: Subject to any disclaimer, the term of this patent is extended or adjusted under 35 U.S.C. 154(b) by 37 days.

(21) Appl. No.: 15/974,927

(22) Filed: May 9, 2018

(65) Prior Publication Data

US 2019/0345227 A1 Nov. 14, 2019

(51) Int. Cl.
| | | |
|---|---|---|
| A61K 38/00 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 14/78 | (2006.01) | |
| C12N 5/0775 | (2010.01) | |
| C07K 14/435 | (2006.01) | |
| C12N 5/00 | (2006.01) | |
| C12N 5/077 | (2010.01) | |

(52) U.S. Cl.
CPC ............ *C07K 14/78* (2013.01); *C07K 14/435* (2013.01); *C12N 5/0068* (2013.01); *C12N 5/0656* (2013.01); *C12N 5/0662* (2013.01); *C07K 2319/60* (2013.01); *C12N 2509/00* (2013.01); *C12N 2533/50* (2013.01); *C12N 2537/10* (2013.01); *C12N 2539/00* (2013.01)

(58) Field of Classification Search
None
See application file for complete search history.

(56) References Cited

U.S. PATENT DOCUMENTS

| 4,816,567 A | 3/1989 | Cabilly et al. |
| 6,613,582 B1 | 9/2003 | Kodadek et al. |

OTHER PUBLICATIONS

Wang et al. "B12-dependent photoresponsive protein hydrogel for controlled stem cell/protein release" Proc. Natl. Acad. Sci. 114: 5912-5917. (Year: 2017).*
Seetulsingh-Goorah SP, "Mechanisms of adenosine-induced cytotoxicity and their clinical and physiological implications," Biofactors, 27:213-230 (2006).
Tessmar JK, Göpferich AM, "Matrices and scaffolds for protein delivery in tissue engineering," Adv Drug Deliv Rev, 59:274-291 (2007).
Shah NJ, et al., "Adaptive growth factor delivery from a polyelectrolyte coating promotes synergistic bone tissue . . . ," Proc Natl Acad Sci USA, 111(35):12847-12852 (2014).
Hu J, et al., "Enhancing pharmacokinetics, tumor accumulation, and antitumor efficacy by elastin-like polypeptide fusion of interferon alpha," Adv Mater, 27:7320-7324 (2015).
Kloxin, AM, et al., "Photodegradable hydrogels for dynamic tuning of physical and chemical properties," Science, 324 (5923):59-69 (2009).
Luo, Y and Shoichet MS, "A photolabile hydrogel for guided three-dimensional cell growth and migration," Nature Materials, 3(4):249-253 (2004).
Wirkner, M et al., "Triggered cell release from materials using bioadhesive photocleavable linkers," Advanced Materials, 23(34):3907-3910 (2011).
Zhou, H & Hockin HK Xu, "The fast release of stem cells from alginate-fibrin microbeads in injectable scaffolds for bone tissue eng . . . ," Biomaterials, 32(30):7503-7513 (2011).
Leslie, SK et al., "Controlled release of rat adipose-derived stem cells from alginate microbeads," Biomaterials, 34(33):8172-8184 (2017).
Mak, WC et al., "Thermo-rheological responsive microcapsules for time-dependent controlled release of human mesenchymal . . . ," Biomaterials Science, 5:2241-2250 (2017).
Lee KY, Mooney DJ, "Hydrogels for tissue engineering," Chem Rev, 101(7):1869-1879 (2001).
DeForest CA, Anseth KS, "Advances in bioactive hydrogels to probe and direct cell fate," Annu Rev Chem Biomol Eng, 3:421-444 (2012).
Langer R, Tirrell DA, "Designing materials for biology and medicine," Nature, 428:487-492 (2004).
Burdick JA, Murphy WL, "Moving from static to dynamic complexity in hydrogel design," Nat Commun, 3:1269 (2012).
DeForest CA, Anseth KS, "Cytocompatible click-based hydrogels with dynamically tunable properties through orthogonal photoconjugation . . . ," Nat Chem, 3:925-931 (2011).
Tomatsu I, Peng K, Kros A, "Photoresponsive hydrogels for biomedical applications," Adv Drug Deliv Rev, 63:1257-1266 (2011).
Katz JS, Burdick JA, "Light-responsive biomaterials: Development and applications," Macromol Biosci, 10:339-348 (2010).
Yagai S, Kitamura A, "Recent advances in photoresponsive supramolecular self-assemblies," Chem Soc Rev, 37:1520-1529 (2008).
Deisseroth K, "Optogenetics," Nat Methods, 8(1):26-29 (2011).
Ercole F, Davis TP, Evans RA, "Photo-responsive systems and biomaterials: photochromic polymers, light-triggered self-assembly, . . . ," Polym Chem, 1:37-54 (2010).
Fairbanks BD, et al.,"Thiol-Yne Photopolymerizations: Novel mechanism, kinetics, and step-growth formation of highly cross-linked networks," Macromolecules, 42:211-217 (2009).

(Continued)

*Primary Examiner* — James H Alstrum-Acevedo
*Assistant Examiner* — Zachary J Miknis
(74) *Attorney, Agent, or Firm* — Duane Morris LLP

(57) ABSTRACT

The present disclosure provides light-sensitive protein hydrogels, and methods of their use thereof. The hydrogels can be used for cell encapsulation, culturing, and selective release under appropriate light conditions.

20 Claims, 33 Drawing Sheets
(11 of 33 Drawing Sheet(s) Filed in Color)
Specification includes a Sequence Listing.

(56) References Cited

OTHER PUBLICATIONS

DeForest CA, Polizzotti BD, Anseth KS, "Sequential click reactions for synthesizing and patterning three-dimensional cell microenvironments," Nat Mater, 8:659-664 (2009).
DeForest CA, Tirrell DA, "A photoreversible protein-patterning approach for guiding stem cell fate in three-dimensional gels," Nat Mater, 14:523-531 (2015).
Alvarez-Lorenzo C, Bromberg L, Concheiro A, "Light-sensitive intelligent drug delivery systems," Photochem Photobiol, 85:848-860 (2009).
Fairbanks B.D., et al., "A versatile synthetic extracellular matrix mimic via thiol-norbornene photopolymerization," Adv Mater, 21:5005-5010 (2009).
Sun F, Zhang, et al., "Synthesis of bioactive protein hydrogels by genetically encoded SpyTag-SpyCatcher chemistry," Proc Natl Acad Sci USA, 111(31):11269-11274 (2014).
Banta S, Wheeldon IR, Blenner M, "Protein engineering in the development of functional hydrogels," Annu Rev Biomed Eng, 12:167-186 (2010).
Gao X, Fang J, Xue B, Fu L, Li H, "Engineering protein hydrogels using SpyCatcher-SpyTag chemistry," Biomacromolecules, 17:2812-2819 (2016).
Fang J., et al., "Forced protein unfolding leads to highly elastic and tough protein hydrogels," Nat Commun, 4:2974 (2013).
Murphy W.L., et al., "Dynamic hydrogels: Translating a protein conformational change into macroscopic motion," Angew Chem Int Ed, 46:3066-3069 (2007).
Botyanszki Z, et al., "Engineered catalytic biofilms: Site-specific enzyme immobilization onto *E. coli* curli nanofibers," Biotechnol Bioeng, 112(10):2016-2024 (2015).
Zhang WB, Sun F, Tirrell DA, Arnold FH, "Controlling macromolecular topology with genetically encoded SpyTag-SpyCatcher chemistry," J Am Chem Soc, 135:13988-13997 (2013).
Matsunaga R, Yanaka S, Nagatoishi S, Tsumoto K, "Hyperthin nanochains composed of self-polymerizing protein shackles," Nat Commun, 4:2211 (2013).
Fairhead M, et al., "SpyAvidin hubs enable precise and ultrastable orthogonal nanoassembly," J Am Chem Soc, 136:12355-12363 (2014).
Liu ZD, et al., "A novel method for synthetic vaccine construction based on protein assembly," Sci Rep UK, 4:7266 (2014).
Bedbrook CN, et al., "Genetically encoded spy peptide fusion system to detect plasma membrane-localized proteins in vivo," Chem Biol, 22: 1-14 (2015).
Urry DW, "Physical chemistry of biological free energy transduction as demonstrated by elastic protein-based polymers," J Phys Chem B 101:11007-11028 (1997).
Santoro M, Tatara AM, Mikos AG, "Gelatin carriers for drug and cell delivery in tissue engineering," J Control Release, 190:210-218 (2014).
Vo TN, Kasper FK, Mikos AG, "Strategies for controlled delivery of growth factors and cells for bone regeneration," Adv Drug Deliv Rev, 64:1292-1309 (2012).
Sension RJ, et al., "Time-resolved spectroscopic studies of B12 coenzymes: Comparison of the influence of solvent on the primary . . . ," J Phys Chem B, 109:21954-21962 (2005).
Nguyen, L. T., et al., "Lipid Pools As Photolabile "Protecting Groups": Design of Light-Activatable Bioagents," Angew. Chem., 125:10120-10123 (2013).
Marks, J. D., et al., "By-passing Immunization" J. Mol. Biol., 222:581-597 (1991).
Prescher, J. A., Bertozzi, C. R.,"Chemistry in living systems," Nat. Chem. Biol. 1(1): 13-21 (2005).
Jones, P. T., et al., "Replacing the complementarity-determining regions in a human antibody with those from a mouse," Nature, 321:522-525 (1986).
Riechmann, et al., "Reshaping human antibodies for therapy," Nature, 332:323-327 (1988).
Verhoeyen, et al., "Reshaping Human Antibodies: Grafting an Antilysozyme Activity," Science, 239:1534-1536 (1988).
Kohler, et al., "Continuous cultures of fused cells secreting antibody of predefined specificity," Nature, 256:495-497 (1975).
Clackson, T., et al., "Making antibody fragments using phage display libraries," Nature, 352:624-628 (1991).
Paleologue, A., et al., "Photo-Induced Protein Cross-Linking to 5S RNA and 28-5.8S RNA within Rat-Liver 60S Ribosomal Subunits," Eur. J. Biochem., 149, 525-529 (1985).
Hino, N., et al., "Protein Photo-Cross-Linking in Mammalian Cells by Site-Specific Incorporation of a Photoreactive Amino Acid," Nature Methods, 2(3):201-206 (2005).
Suda,Y., et al., "Novel Photo Affinity Cross-Linking Resin for the Isolation of Heparin Binding Proteins," Journal of Bioactive and Compatible Polymers, 15:468-477 (2000).
Bochet, C. G., "Orthogonal Photolysis of Protecting Groups," Angew. Chem. Int. Ed. 40:2071-2073 (2001).
Sui ZJ, King WJ, Murphy WL, "Protein-based hydrogels with tunable dynamic responses," Adv Funct Mater, 18:1824-1831 (2008).
Kutta RJ, et al., "The photochemical mechanism of a B12-dependent photoreceptor protein," Nat Commun, 6:7907 (2015).
Jost M, et al., "Structural basis for gene regulation by a B12-dependent photoreceptor," Nature, 526:536-541 (2015).
Ortiz-Guerrero JM, et al., "Light-dependent gene regulation by a coenzyme B12-based photoreceptor," Proc Natl Acad Sci USA, 108(18):7565-7570 (2011).
Jost M, et al., "The transcription factor CarH safeguards use of adenosylcobalamin as a light sensor by altering the photolysis products," Biochemistry, 54:3231-3234 (2015).
Zakeri B, et al, "Peptide tag forming a rapid covalent bond to a protein, through engineering a bacterial adhesin," Proc Natl Acad Sci USA, 109:E690-E697 (2012).
Schoene C, Fierer JO, Bennett SP, Howarth M, "SpyTag/SpyCatcher cyclization confers resilience to boiling on a mesophilic enzyme," Angew Chem Int Ed, 53:6101-6104 (2014).
Veggiani G, et al., "Programmable polyproteams built using twin peptide superglues," Proc Natl Acad Sci USA, 113(5):1202-1207 (2016).
Reddington SC, Howarth M, "Secrets of a covalent interaction for biomaterials and biotechnology: SpyTag and SpyCatcher," Curr Opin Chem Biol, 29:94-99 (2015).
Chen AY, et al., "Synthesis and patterning of tunable multiscale materials with engineered cells," Nat Mater, 13:515-523 (2014).
Huebsch, N. et al., "Matrix elasticity of void-forming hydrogels controls transplanted-stem-cell mediated bone formation," Nature Materials, 14(12):1269-1277 (2015).
Shell, T. et al., "Tunable Visible and Near-IR Photoactivation of Light-Responsive Compounds by Using Fluorophores as . . . ", Angew. Chem. Int. Ed. 53:875-878 (2014).
Devereux et al., "A comprehensive set of sequence analysis programs for the VAX," Nucleic Acids Research, 12(1):387-395 (1984).
Altschul S. F., "A Protein Alignment Scoring System Sensitive at All Evolutionary Distances," J Mol Evol., 36:290-300 (1993).
Altschul, S. F. et al., "Basic Local Alignment Search Tool," J Mol Biol. 215:403-10 (1990).
Henikoff and Henikoff, "Amino acid substitution matrices from protein blocks," Proc. Natl. Acad. Sci. USA, 89:10915-10919 (1992).
Karlin and Altschul, "Applications and statistics for multiple high-scoring segments in molecular . . . ," Proc. Natl. Acad. Sci. USA, 90:5873-5787 (1993).
Zakeri, et al., "Peptide tag forming a rapid covalent bond to a protein, through engineering a . . . ," Proc. Natl. Acad. Sci. USA, 109(12):4347-4348 (2012).
Sun, et al., "Synthesis of bioactive protein hydrogels by genetically encoded SpyTag-SpyCatcher chemistry," Proc. Natl. Acad. Sci. USA, 111(31):11269-11274 (2014).
Carothers, W. H., "Polymers and Polyfunctionality," Trans. Faraday Soc. 32, 39 (1935).

\* cited by examiner

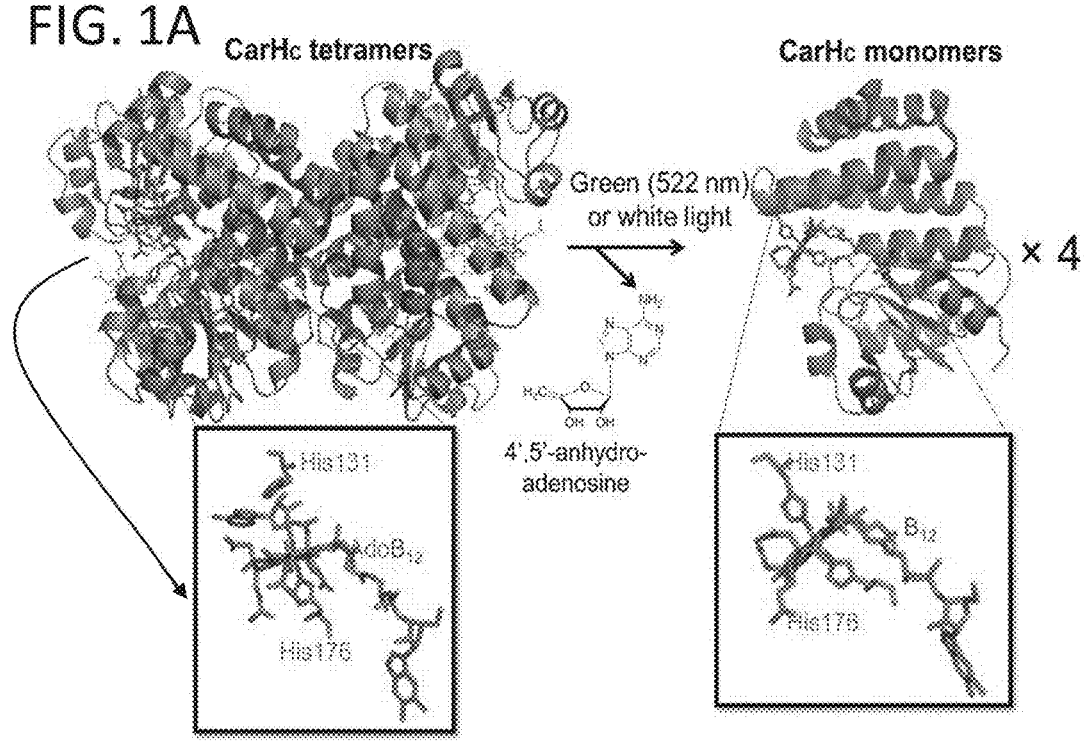
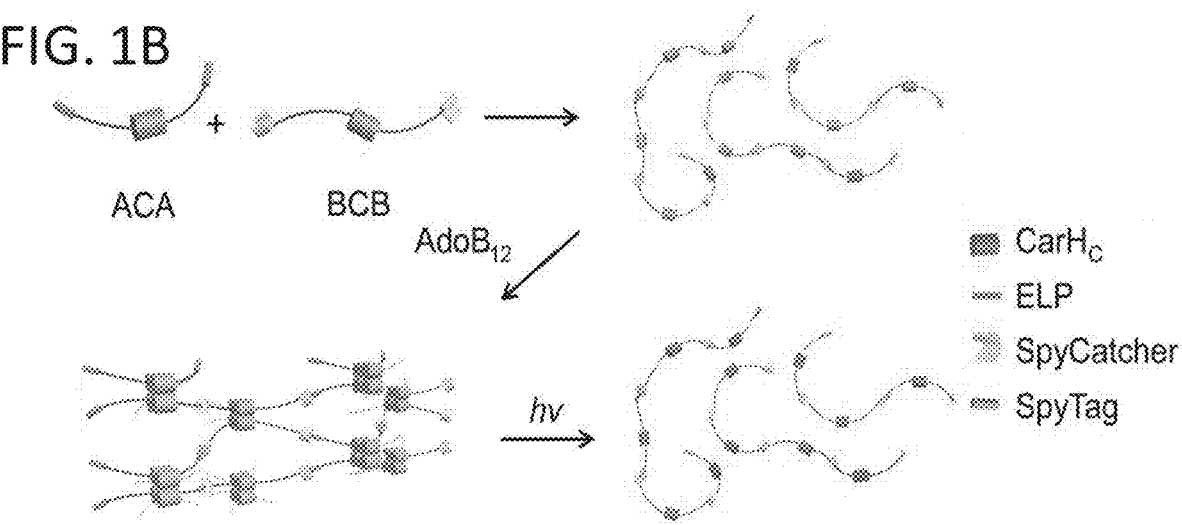

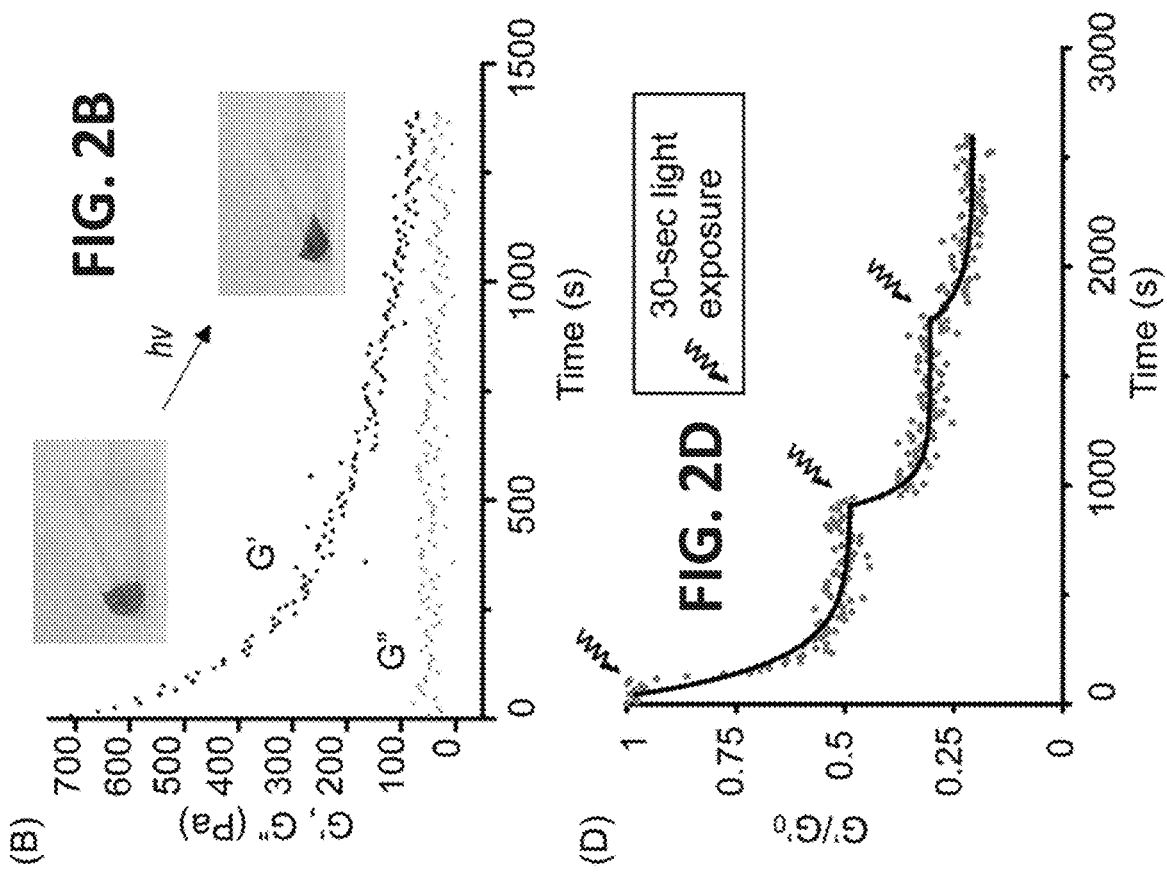

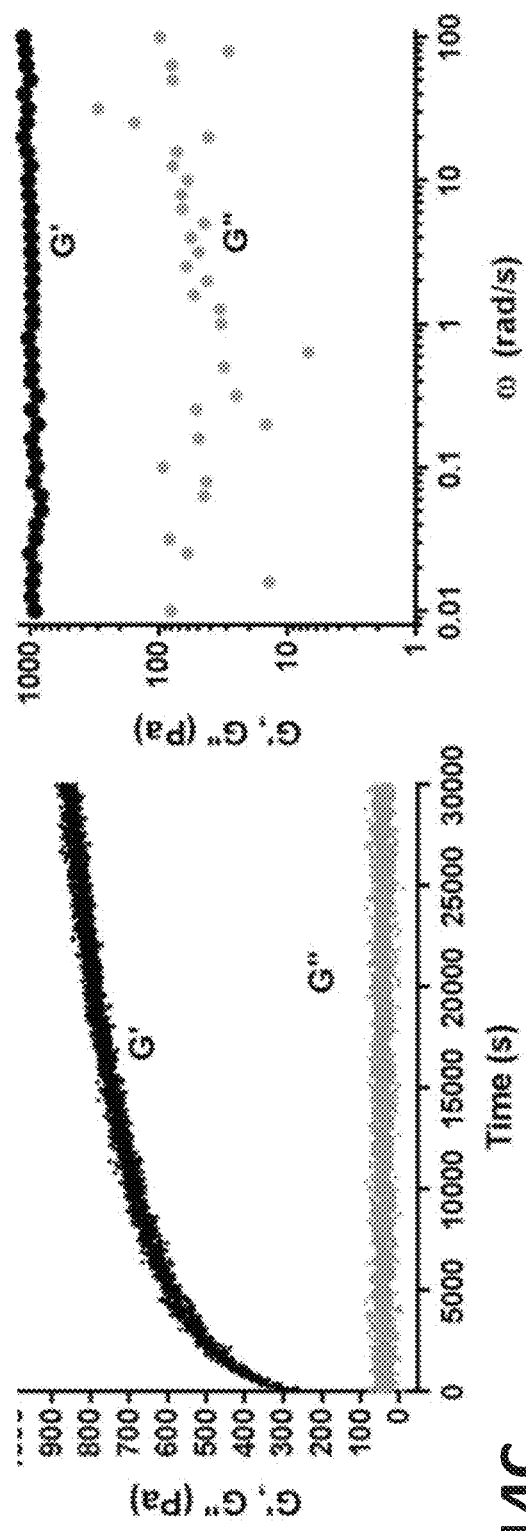
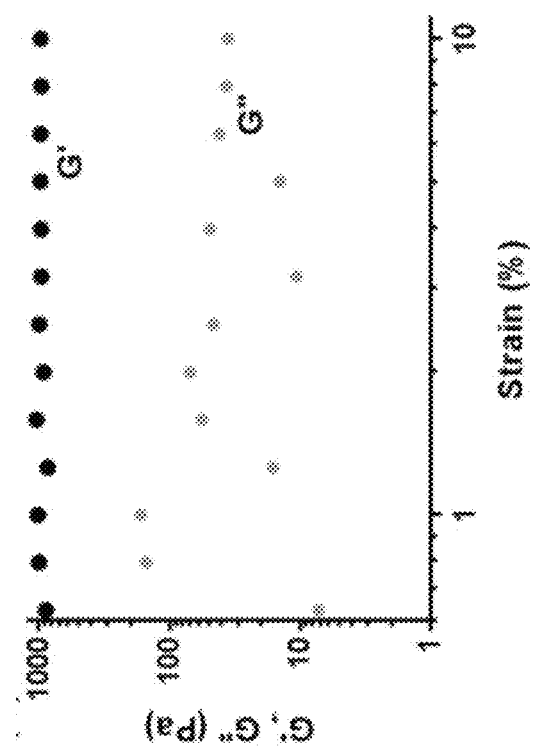
FIG. 14A
FIG. 14B
FIG. 14C

FIG. 18
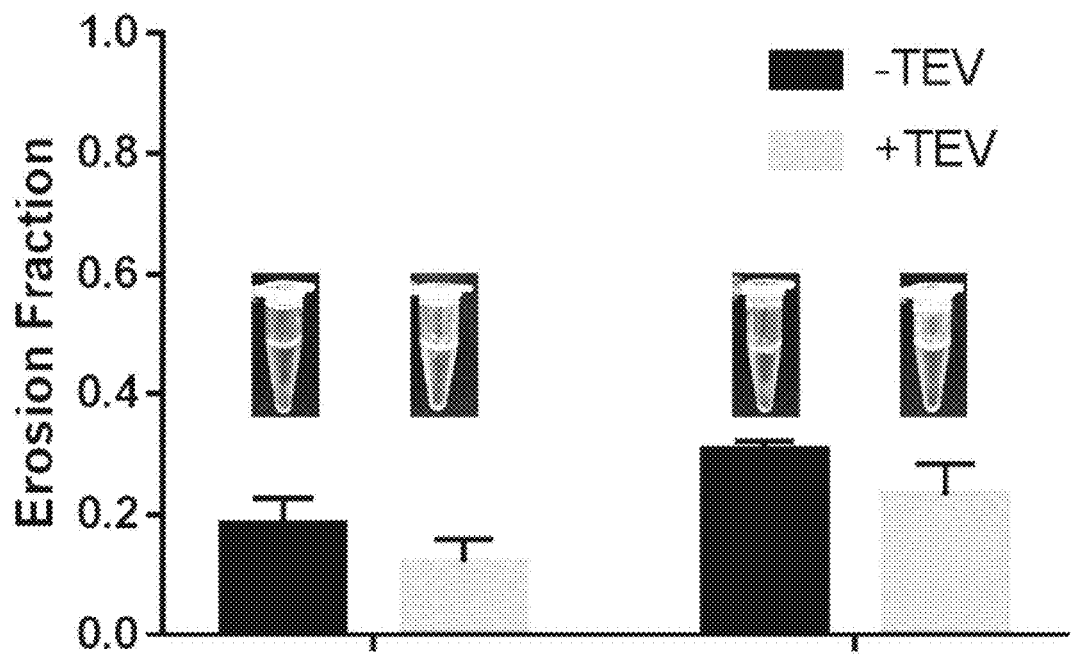
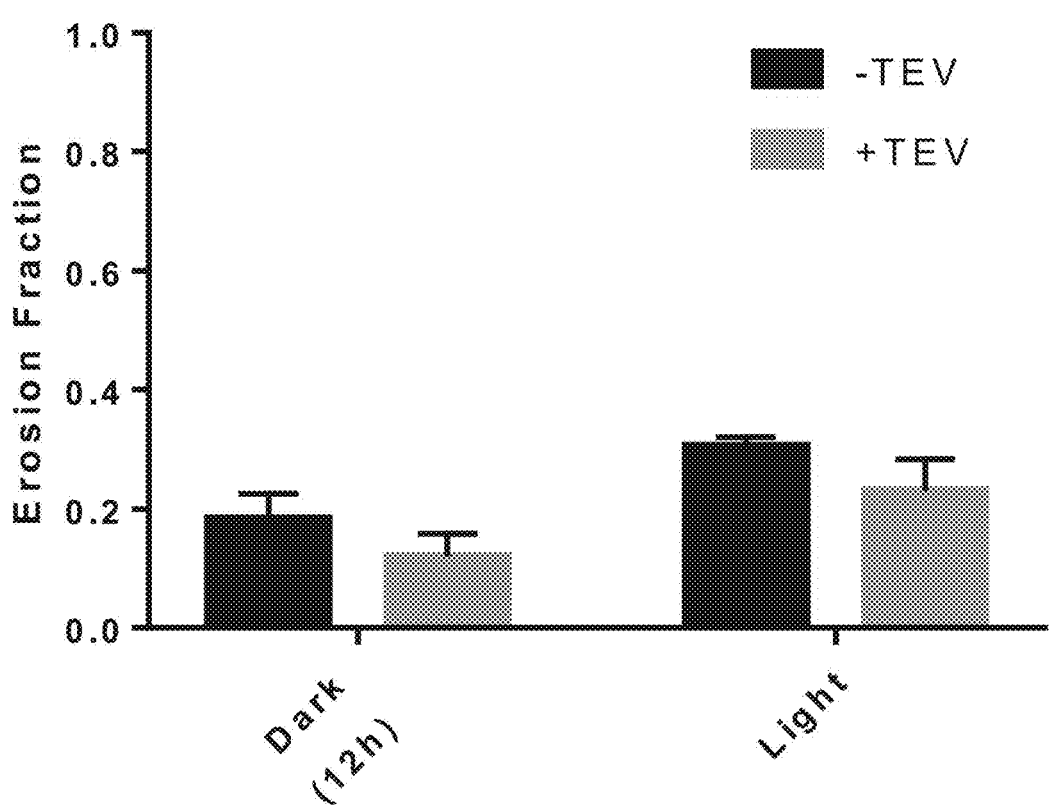

FIG. 19A

SpyCatcher-ELP-CarH$_C$-ELP-SpyCatcher (BCB)

```
ATGAAAGGCAGCAGCCATCATCATCATCATCACGTCGACATCCCAACGACCGAAAACCTGTATTTCAGGGCGCCAT
GGTTGATACCTTATCAGGTTTATCAAGTGAGCAAGGTCAGTCCGTGATATGACAATTGAAGAAGATAGTGCTACCC
ATATTAAATTCTCAAAACGTGAGGACGCAAAGAGTTAGCTGGTGCAACTATGGAGTTGCGTGATTCATCTGGT
AAAACTATTAGTACATGGATTTCAGATGACAAGTGAAAGATTTCTACCTGTATCCAGGAAAATATACATTTGTCGA
AACCGCAGCACCAGACGCGGTTATGAGAGGTAGCAACTGCTATTACCTTTACAGTTAATGAGCAAGGTCAGTGTAA
ATGGCAAAGCAACTAAAGGTGACGCTCATATTGACGGTCCGCAAGGTATTTGGGTGCCGGGCGTGTGCCACGGCGTG
GGTGTTCCGGGCGTTGGTGCGTCCGGTGCGGGCGCGGGGCGTGTCCGGTGTTGGTGTGTCCGGGCGTGTGGG
TGCCGGGCGTGGGCGTGCCCGGGCCCGAAGCTCTGGGCGGTGATCTGGCGGGCGCCGAAGCTCTGTTTCG
TCGTGGCCTGCTCTTCTGGGGCCCGGAAATCGGCGTTGCTGAAGAACAACCTGGAGCCGGTTCTGAAGGCGGGCGAAG
CTTGGCACCCGTGGCAGGTTTCCCGCCGGTGCAGGTTCCTGGTGACTACGCCGGTCCTGGTGACTACGCCGGTGC
CTGGACCCTGGCAGGTTTCCCGCCGGTGCAGGTTCCTGGTGACTACGCCGGTCCTGGTGACTACGCCGGTGC
GATGCTGCCGCCGTACCATCTGCGCTTCGAAGGGCGCGGTGCCGGATATCTGGGCCGGATATCTGCGCTGCCGGACC
TGCGTGCACTGGCCGCGCCGCCTGGGCGTGGGCCAGGCGCGGTGGTCTGAGCGCGCAGCCGTGCTGTGCTCTG
CCTGACGGTGCCGAATACATGGAAGATCGGAAGACCTGAAAGGCCTGAAAGCCCGCGCGGTGCCGCGGTCCGGCG
TCTGGGTGGCCCGAATACATGGAAGATCGGAAGACCTGAAAGGCCTGGTGTTCCGGGCCGTTGGTGTGCCG
CAATCGCTATTGTGCCGCGTCCGGGCGGTAGGGTCCGCAGGGTGCCGGGTGTCCGGGCCGTTGGTGTGCCGGGG
GGCGTCGGCCGTGTTCCGGGCGTAGGGTGGGTGTTCCGGGCGTAGGTGTGCCGGGGCGTTGGTGTGCCGGGGTG
CGTAGGTGTTCCGGGCGTAGGTGTGCCGGGGCGTTGGTGTGCCGGGCCATGCGGCCATGCGGCCGTTGATACCTTA
TGGCCGTGGCCCGCCACATCCCGACATCCCGGTGATATGACAACTATGGCAACTATGGCGCCATATTAAATTCTC
TCAGGGTTTATCAAGTGAGCAAGGTCAGTGAGCAAGGTGAAGATTGACAAGTTGCGTGATTCATCTGTAAATTCTCTC
AAAACGTGATGAGGACGCAACGCAAAGAGTTAGCTGGTGCAACTATGCAACTATGGCGTGATTCATCTGTAAATTCTC
CATGGATTTCAGATGACAAGTGAAAGATTCTACCTTTACAGTTAATGAGCAAGGTCAGTGTAAAAACTATTAGTA
GACGGTTATGAGGTTATCAAGTGGACAAGTGCTGTTACCTTTACAGTTAATGAGCAAGGTCAGTGTAAAAACTATTAGTA
CACGGTTATGAGGTTATCAAGTGGACAACTGCTATTACCTTTACAGTTACTGTAAGGTCAAAGCAAC
TAAAGGTGACGCTCATATTGACGGTTCCGCAAGGTATTTGGGGTCAGCTCGAGTGGAAGAAATAA
```

FIG. 19B

MKGSSHHHHHHVDIPTTENLYFQGAMVDTLSGLSSEQGQSGDMTIEEDSATHIKFSKRDEDGKELA
GATMELRDSSGKTISTWISDGQVKDFYLYPGKYTFVETAAPDGYEVATAITFTVNEQGQVTVNGKA
TKGDAHIDGPQGIWGQLEGHGVGVPGVGVPGEGVPGVGVPGVGVPGEGVPGVGVPGEGVPG
VGVPGVGVPGEGVPGVGVPGVGVPGEIPGTGTHEAIRGDIASFEAIRRGIVEHGCAEFHIASIPTIRFICELLIIAGFPPGFPVLVIPPGFPH
IICAMLAVHLRRCVPAIVLGEDTIPIEDIPALAGGACAVLSAVLSEPIAISDIADR
VHLGGGCDEELARLGAHLGAHLMEDLKGLADALNPGGFKEAITSVPGVGVPGVGVPGEGVPGVGVP
GVGVPGVGVPGEGVPGVGVPGVGVPGGLVDIPTTEN
LYFQGAMVDTLSGLSSEQGQSGDMTIEEDSATHIKFSKRDEDGKELAGATMELRDSSGKTISTWIS
DGQVKDFYLYPGKYTFVETAAPDGYEVATAITFTVNEQGQVTVNGKATKGDAHIDGPQGIWGQLEW
KK

FIG. 20A

SpyTag-ELP-CarH$_C$-ELP-SpyTag (ACA)

ATGAAAGGCAGCAGCCATCATCATCATCATCATGTTGACGCCCATATTGTCATGGTTGATGCATACAAGCCGACGAA
GCTCGACGGCCACGGCCTGGCGTTCCGGGCCGTGTGCCGGGCCGTGTGCCGGAAGGTGTGCCGGGCG
TCGGTGTGCCGGGCGTTGGTGTTCCGGGCCGTTGGTGTGCCGGGCCGTGAGGGTGTGCCGGGCGTT
GGTGTTCCCGGGCCGTGTGCCGGGCCGTGTTCCCGGGCCGTGTTCCCGGGCGTGTGCCGGGCGTAGG
TGTGCCGGGCGTTGGTGACGCTCCCAGAAGATCTGGGCACCGGCACTGCTGCCGGGTGATCTGGCGG
GCGCCGAAGCTCTGCGTTTCGTGGCCCTGCGTGGCGTTCTGAGCCGTTCTGAGCACCTGCTGCCGGTG
CTGCGTGAAGTGGGCGAAGCTTGGCACCGGTGAAATCGGCGTTGCAGAAGAACCTGGCGAGCACCTTCCTGCG
CGCCGGTCTGCAAGGAGCTGGACCTGGCAGGTTCCCGGGCCGTCCTGCCTGGTGACTACGCCCGCGGGCCG
AACGCCACGAAATCCCGCGGTGCGATGCTGGCGGGCGTACCATCTGCTCGCCGTAAGGGCGTCGCCGGCGTCGTGCTGTATCGTCTGGGCCCG
GATACTCCCGCGTCTGCCTGCCGTGCACCGGTCACCGGGTGCCCCTGAAAGATCTGGCACCGCCGTGTTTCCTGGCGGCCCAGGGCGCAG
CGAACCGGCGTCGTCCTGCGGTGCCGATGCCCTGGTCACCGGGCCGTCGCCGGTGTTTCCTGGCGCTGAAAGCCTGTGGCTGCCG
GCCCCGGAAGCCCGGGCGTTCCCGGGCGTGCCGGGCGTAGGTGTTCCCGGGCGTAGGTGTGTCCCGGGCGAGGGTGT
TCCGGGCCGTTGGTGTGCCGGGCGTCGGCGTGTGCCGGGCGTAGGTGTGCCGGGCGAAGGCGTGCCGGGCGTGC
CGGGGCGTAGGTGCCGGGCGTAGGTGTGCCGGGCGTAGGTGTTCCCGGGCGTAGGTGTTCCCGGGCGTGAAGGCGTGCCG
GGCGTTGGTGTGCCGGGCTGTGGGCCGTGCTGCTCGACGCCCATATTGTCATGGTTGATGCATACAAGCC
GACGAAGCTGACTGGAAGAAATAA

FIG. 20B

MKGSSHHHHHHVDAHIVMVDAYKPTKLDGHGVGVPGEGVPGVGVPGVGVPGEGVPGV
GVPGVGVPGEGVPGVGVPGVGVPGEGVPGVGVPGVGVPGEIPGCRGDMPGCRGDSGLPLEPY
KGPCRAKCADICIASGKQIISFPGCPKEFKSGCIRCLCAGYHIPPGCKAEAAKMLI
KGPCRAFTSVPGVGVPGEGVPGVGVPGVGVPGEGVPGVGVPGVGVPGEGVP
GVGVPGVGVPGGLLDAHIVMVDAYKPTKLEWKK

FIG. 21A mCherry-CarH_C

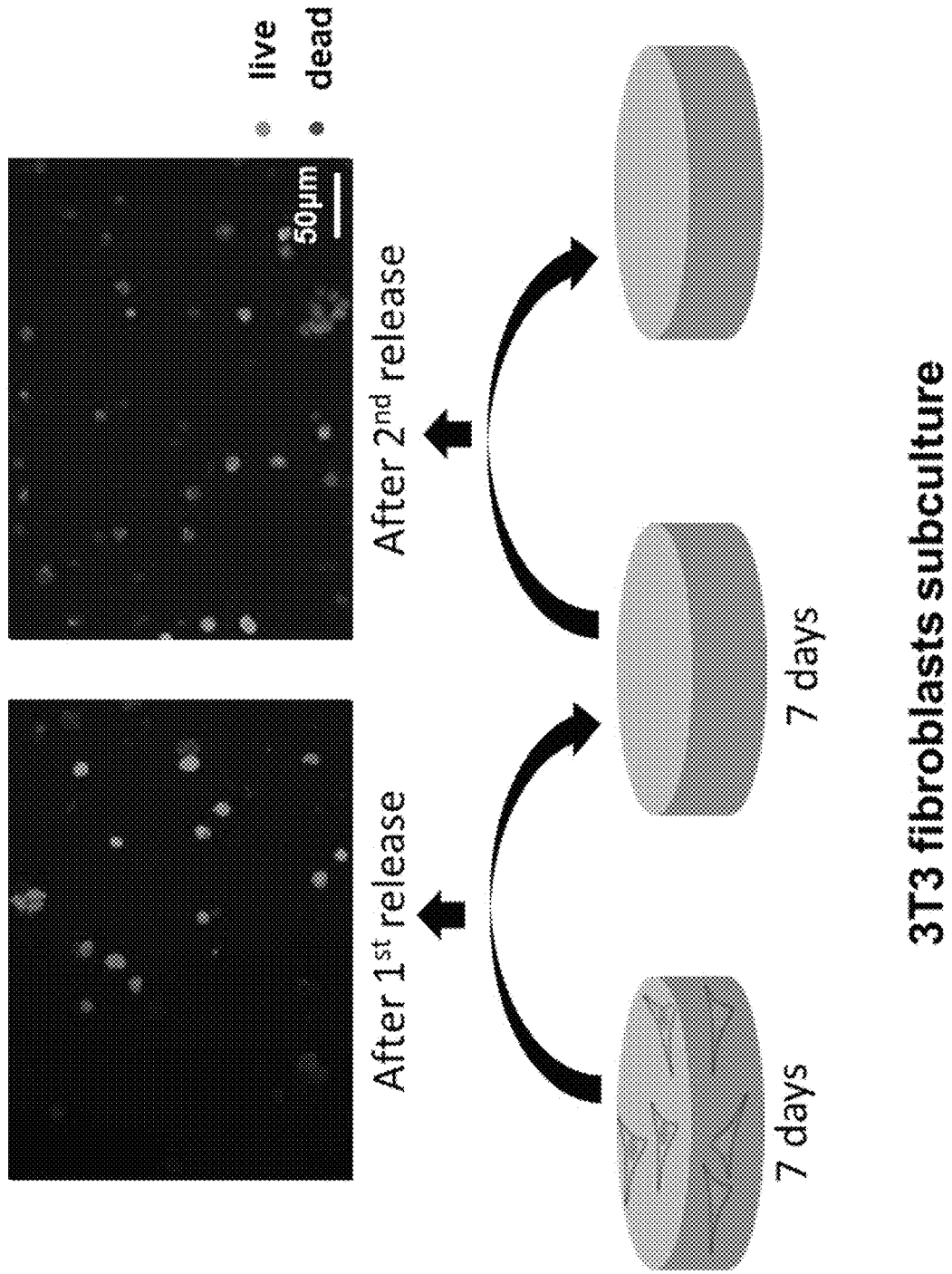

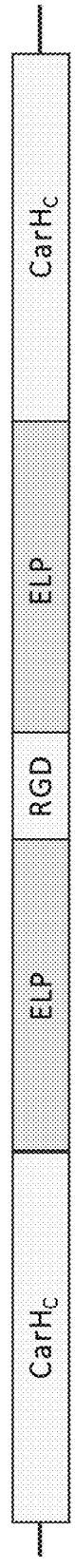
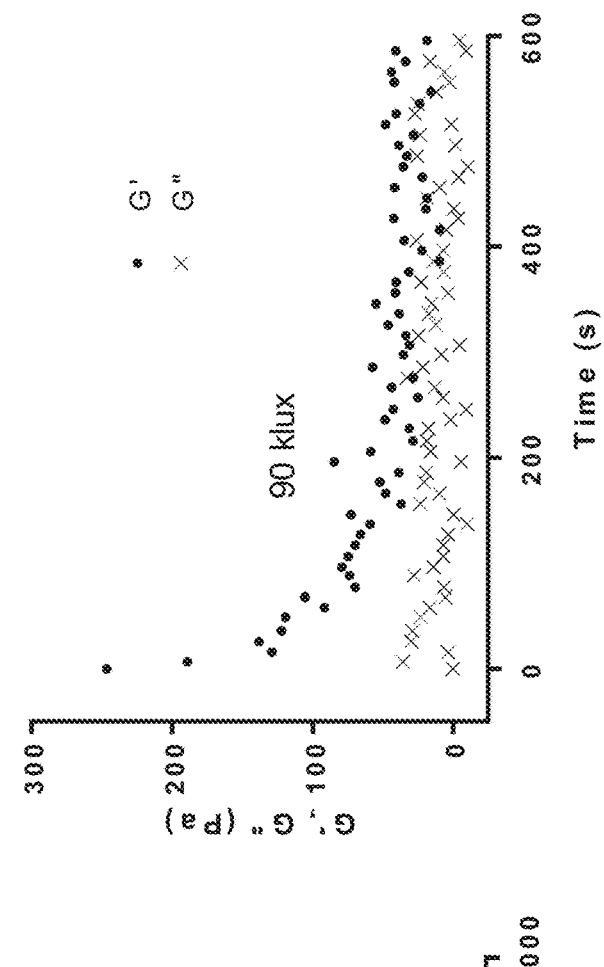
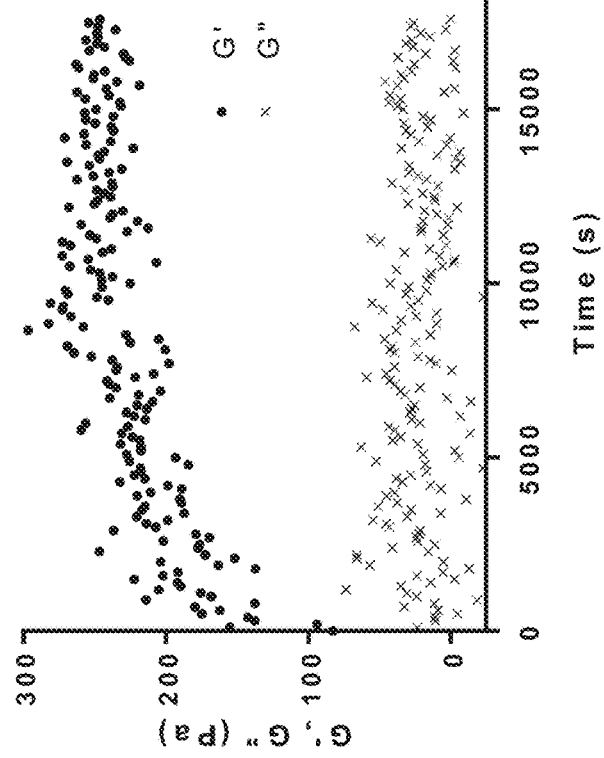

FIG. 26A

Nucleotide sequence of AA (SpyTag-Elastin Protein-SpyTag)

ATGAAAGGCAGCAGCCAGCCATCATCATCATCATCACGTCGACGCCCATATTGTCATGGTTGATGCATACA
AGCCGACGAAGCTGGACGGCCACGGCGTGGTTGTTCCGGGCGTGGTTCCGGGTGTGCCGGGTGTGGGTGTG
CCGGGCGAAGGTGTGCCGGGCGTTGGTGTTCCGGGCGTTGTGCCGGGCGTGGTGCCGGGCGTTGG
CGTTGGCGTGCCGGGCGAGGGTGTGCCGGGCGTTGTGCCGGGCGAAGGTGTGCCGGGCGTTGGTGAG
GCGTGCCGGGCGTACCGGCGTGGTGATAGTCCGGGCCAGCTCTGCCCGATCGCCACTAGTGTGCCGG
CTCTATGCGGTTACCCGGCGTGGTGATAGTCCGGGCGTGTTCCGGGCGTAGGTGTGCCGGGCGTC
GGGTCGGCGCCGGGCGTGGTGTTCCGGGCGTAGGTGTGCCGGGCGAGGGTGTCCGGGCGTGGGCGT
GCCGGGCGTAGGTGTTCCGGGCGTAGGTGTGTTCCGGGCGTAGGTGTGCCGGGCGTAGAGGCGTCCGG
GGGTTGGTGCCGGGTGTGCCGGGCGTGCCGGGCCTGCTCGACGCCATATTGTCATGGTTGATG
CATACAAGCCGACGAAGCTCGAGTGGAAGAAA

FIG. 26B

Amino acid sequence of AA
MKGSSHHHHHHVDAHIVMVDAYKPTKLDGHGVGVPGVGVPGEGVPGVGVPGVGVPGVGVPGVG
VPGVGVPGEGVPGVGVPGVGVPGEGVPGVGVPGVGELYAVTGRGDSPASSAPIATS
VPGVGVPGVGVPGVGVPGVGVPGVGVPGVGVPGEGVPGVGVPGVGVPGVGVPGE
GVPGVGVPGVGVPGGLLDAHIVMVDAYKPTKLEWKK

FIG. 27A

Nucleotide sequence of AAA (SpyTag-Elastin Protein-SpyTag-Elastin Protein-SpyTag)

ATGAAAGGCAGCAGCCATCATCATCATCATCACGTCGACGCCCATATTGTCATGGTTGATGCATACAAGCCG
ACGAAGCTCGACGGCCACGGCGTGGGTGTTCCGGGCGTTCCGGGCGTTGGTGTTCCGGGCGTGCCGGGCGAAG
GTGTGCCGGGCGTCGGTGTGTTCCGGGCGTTGGTGTTCCGGGCGTTCCGGGCGTTGGTGTGCCGGGCGTGCCGGG
CGAGGGTGTGCCGGGCGTTGGTGTTCCGGGCGTGGGTGTTCCGGGCGTGCCGGGCGTGCCGGGCGTCGGTGTT
CCGGGCGAGGGTGTGCCGGGCGTTGCCGGGCGTTGGTCCGGGCGTTGAGCTCGCCCATATTGTCATGGTTGATGC
ATACAAGCCGACGAAGACTAGTGTGCCGGGCGTCGGGGTGTTCCGGGCGTAGGTGTTCCGGGCGAGGGTGTT
CCGGGCGTTGGTGTTCCGGGCGTCCGGGCGTGGGTGTTCCGGGCGTAGGTGTTCCGGGCGTGCCGGGCGAGG
GTGTGCCGGGCGTGCCGGGCGTTGGTGTGCCGGGCGTGCCGGGCGTGCCGGGCGTAGGTGTTCCGGG
TGAAGGCCGTGCCGGGCCTTGGTCCGGGCCTGCTCGACGCGCCATATTGTC
ATGGTTGATGCATACAAGCCGACGAAGCTCGAGTGGAAGAAA

FIG. 27B

Amino acid sequence of AAA

MKGSSHHHHHHVDAHIVMVDAYKPTKLDGHGVGVPGVGVPGVGVPGVPGVPGEGVPGVGVPGVGVPGVGVPGVG
VPGEGVPGVGVPGVGVPGVGVPGVGVPGELAHIVMVDAYKPTKTSVPGVGVPGVGVP
GEGVPGVGVPGVGVPGVGVPGEGVPGVGVPGVGVPGVGVPGVGVPGVGVPGGL
LDAHIVMVDAYKPTKLEWKK

FIG. 28A

Nucleotide sequence of BB. (SpyCatcher-Elastin Protein-SpyCatcher)

ATGAAAGGCAGCAGCCATCATCATCATCATCACGTCGACATCCAACGACCGAAAACCTGTATTTCAGG
GCGCCATGGTTGATACCTTATCAAGTTGAGCAAGTCAGTCGGTGATATGACAATGAAGAA
GATAGTGCTACCCATATTAAATTCTCAAACGTGATGAGGACGGCAAAGAGTAGCTGGTGCAACTATGG
AGTTGCGTGATTCATCTGGTAAAACTATTAGTACATGGATTTCAGATGGACAAGTGAAAGATTTCTACCTG
TATCCAGGAAAATATACATTGTCGAAACCGCAGCACCAGACGGTTATGAGGTAGCAACTGCTATTACCTT
TACAGTTAATGAGCAAGGTCAGGTTACTGTAAATGCAAAGCAACTAAAGGTGACGCTCATATTGACGGT
CCGCAAGGTATTTGGGGTTCAGCTCGAGGGCCACGGCGTGGGGTGTCCGGTGTGCCGGGCGTCCGGCGTTGGTGTCCG
GGTGTGCCGGGCGAAGGTGTCCGGGCGTCCGGGCGTGTGCCGGGCGTCCGGCGTTGGTGTCCG
GGCGTTGGCGTGCCGGGCGAGGGTGTCCGGGCGTGTTCCGGGCGTGTTCCGGGCGTGTGCCGGGCGTGGC
GTGCCGGGCGTCGGTGTTCCGGGCGAGGGTGTGCCGGGCGTAGGTGTGCCGGGCGTTGGTGAGCTCTAT
GCGGTTACCGGCCGTCGGTGGTAGTCCGGCCAGTCGCCGATCGCCCACTAGTGTGCGGGCGTCGGCG
TGCCGGGCGTAGGTGTTCCGGGCGAGGGTGTTCCGGGCGAGGGTGTTGGTGTCCGGGCGTCCGGGCG
TGGGTGTTCCGGGCGTAGGTGTGCCGGGCGTGTCCGGGTGTCCGGGTGAAGGCGGTGTCCGGGCGTACCAGGGGTGGTC
CGGGCGTAGGTGTTCCGGGCGTGTGCCGGGCGTGTCCGGGTGAAGGCGGTGTCCGGGCGTTGG
GCGTGCCGGGCGTCGGTGTCGACATCCCAACGACCGAAAACCTGTATTTTCAGGCCATGGTTGATAC
CTTATCAGTTATCAAACGTGATGAGCAAGGTCAGGTCGGTGATATGACAATTGCTGGTGCAACTATGGATTA
TTAAATTCTCAAACGTGATGAGCAAGGTCAGGTCAAGAGTTAGCTGGTGCAACTATGGATTGCTGATTCATC
TGGTAAACTATTAGTACATGGATTTCAGATGGACAAAGATTTCTACCTGTATCCAGGAAAATATA
CATTGTCGAAACCGCAGCACCAGACGGTTATGAGGTAGCAACTGCTATTACCTTTACAGTTAATGAGCA
AGGTCAGGTTACTGTAAATGCAAAGCAACTAAAGGTGACGCTCATATTGACGGTCCGCAAGGTATTTGG
GGTCAGCTCGAGTGGAAGAAA

FIG. 28B

Amino acid sequence of BB

MKGSSHHHHHHVDIPTTENLYFQGAMVDTLSGLSSEQQQSGDMTIEEDSATHIKFSKRDEDGKELAGATMEL
RDSSGKTISTWISDGQVKDFYLYPGKYTFVETAAPDGYEVATAITFTVNEQGQVTVNGKATKGDAHIDGPQGI
WGQLDGHGVGVPGVGVPGEGVPGVGVPGEGVPGVGVPGEGVPGVGVPGEGVPGVGVPGVGVPGVGVPG
VGVPGEGVPGVGVPGVGELYAVTGRGDSPASSAPIATSVPGVGVPGEGVPGVGVPGVGVPGVGVPGVGVPG
VGVPGEGVPGVGVPGVGVPGEGVPGVGVPGGLLDIPTTENLYFQGAMVDTLSGLSS
EQGQSGDMTIEEDSATHIKFSKRDEDGKELAGATMELRDSSGKTISTWISDGQVKDFYLYPGKYTFVETAAPD
GYEVATAITFTVNEQGQVTVNGKATKGDAHIDGPQGIWGQLEWKK

FIG. 29

| | Relevant Characteristics | SEQ ID NO: | Sources |
|---|---|---|---|
| *E. coli* Strains: | | | |
| DH5α | | | Stratagene |
| BL21 star(DE3) | | | Invitrogen |
| Plasmids: | | | |
| pQE-80L | T5-promoter-operator, N-terminal His6-tag, Amp$^r$ | | Qiagen |
| pQE-AAA | The plasmid for the expression of SpyTag-ELP-SpyTag-ELP-SpyTag | | Sun *et al., id.* |
| pQE-ACA | The plasmid for the expression of SpyTag-ELP-CarH$_C$-ELP-SpyTag | | This study |
| pQE-BCB | The plasmid for the expression of SpyCatcher-ELP-CarH$_C$-ELP-SpyCatcher | | This study |
| pET22b(+) | T7-promoter-operator, C-terminal His6-tag, Amp$^r$ | | Novagen |
| pET22b-mCherry | The plasmid for the expression of mCherry | | This study |
| pET22b-mCherry-CarH$_C$ | The plasmid for the expression of mCherry | | This study |
| Primers: | | | |
| CarH$_C$_SacI_F | GGCGAGCTCCCAGAAGATCT | SEQ ID NO: 14 | Sangon |
| CarH$_C$_SpeI_R | GACACTAGTGATTGCTTCTTTTCCGGA | SEQ ID NO: 15 | Sangon |
| mCherry_NdeI_F | ATAACATATGATGGTGAGCAAGGGCGAGG | SEQ ID NO: 16 | Sangon |
| mCherry_SacI_R | CAATGAGCTCCTTGTACAGCTCGTCCATG | SEQ ID NO: 17 | Sangon |

PHOTORESPONSIVE PROTEIN HYDROGELS AND METHODS AND USES THEREOF

SEQUENCE LISTING

The instant application contains a Sequence Listing which has been submitted electronically in ASCII format and is hereby incorporated by reference in its entirety. Said ASCII copy, created on May 4, 2018, is named Y7564-00002_SL.txt and is 65,309 bytes in size.

FIELD

The present disclosure is generally related to novel photoresponsive protein hydrogels and methods and uses thereof. More specifically, the disclosure provides composition and methods for cell encapsulation and selective release by modulating the gelation of the cellular environment using B12-dependent photoresponsive protein hydrogels.

BACKGROUND

The following includes information that may be useful in understanding various aspects and embodiments of the present disclosure. It is not an admission that any of the information provided herein is prior art, or relevant, to the presently described or claimed inventions, or that any publication or document that is specifically or implicitly referenced is prior art.

Noted for their biomimetic properties, hydrogels are used for biomedical applications, such as drug delivery, stem cell therapy and regeneration medicine and tissue engineering. Hydrogels are also favored in cell culture platforms due it their tissue-like softness and desired water content.

Traditional hydrogels made up of either synthetic polymers or natural biomolecules often serve as passive scaffolds for molecular or cellular species, which render these materials unable to fully recapitulate the dynamic signaling involved in biological processes, such as cell/tissue development. Thus, there is a need to design stimuli-responsive, dynamic hydrogels that can accommodate or mimic the complexity of biological systems.

A type of dynamically tunable hydrogel is a photoresponsive hydrogel. Photoresponsive hydrogels utilize light as a tool to control molecules or cell behavior with high spatiotemporal precision and little invasiveness. Through advancement of synthetic chemistry, progress has been made in making photoresponsive hydrogels with dynamically tunable properties. Through a combination of orthogonal click reactions and photochemistry, some of these synthetic hydrogels can be mechanically and chemically patterned in situ by light while being used for 3D cell culturing, and diverse photoactive chemical moieties have also been incorporated into synthetic hydrogels to create photoresponsive devices for controlled therapeutic release.

Assembling genetically engineered proteins into molecular networks represents an alternative strategy to make hydrogels with well-controlled properties. Although natural evolution has led to numerous functional protein domains that can sense and respond to a variety of environmental stimuli, such as light, oxidative stress, pH, small molecules, metal ions, etc., such ecological diversity has yet to be fully tapped to develop responsive biomaterials with dynamically tunable properties.

Cell culture is typically carried out by seeding a suitable medium with cells of a population to be expanded. Certain adherent cell types, such as human embryonic stem cells (hESC) and induced pluripotent cells (iPC's), are more effectively cultured by providing a surface upon which the cells can adhere to and proliferate. After adhesion and proliferation, the cultured cells need to be harvested and therefore released from the surface. Release of the cells is typically promoted by techniques such as mechanical scraping, chemical or enzymatic treatment, sonication, or a combination thereof.

The inventors have recognized that common cell release techniques can present a number of disadvantages. For example, mechanical scraping can damage the cells, and it is often not suitable for use in confined spaces such as small diameter wells or with three dimensional structures. The use of biological (e.g., protease), or thermal methods (e.g., lowering temperature below LCST) can present a few problems including inefficient release, cell damage or death and/or present a risk of introducing impurities into the cultured cells. For example, a common agent such as trypsin is known to promote deterioration of cell function. Furthermore, certain cells can be particularly adherent to a given substrate and need to be subjected to forcing conditions to promote their release, the effect of which results in a degree of cell damage.

As stated above, hydrogels, such as protein hydrogels, are used in cell culture platforms since they closely mimic native extracellular matrix, which is not only due to their identical nature of the chemical compositions (poly-(amino acid)), but also due to their similar built-in functional moieties (e.g., RGD cell adhesion site and matrix metalloproteinase cleavage site) that assist in cell adhesion or migration. As a result, cell growth, proliferation and differentiation can be controlled on such cell culture platforms including hydrogels.

However, even with the use of present hydrogels in cell culture platforms, there is still a need to improve cell release techniques to maximize harvesting cultured cells in an efficient manner while minimizing damage to and/or loss of the cultured cells.

Additionally, there is a need to improve synthesis techniques for stimuli-responsive "smart" protein-based hydrogels since it is a major challenge to assemble complex globular proteins into supramolecular architectures efficiently while preserving their function.

SUMMARY OF THE INVENTION

In light of the above, the present invention is based on the surprising discovery of novel light-responsive protein hydrogels made of recombinant proteins that can be used as substrates for at least the dual purposes of cell culture and cell release.

For example, in one aspect, a light-responsive hydrogel biopolymer matrix comprising a plurality of adenosylcobalamin (AdoB$_{12}$)-dependent photoreceptor C-terminal adenosylcobalamin binding domain (CarHc or CarH$_c$) proteins, wherein each CarHc protein is covalently stitched with another CarHc protein using genetically encoded SpyTag-SpyCatcher chemistry. The resulting light-responsive hydrogel biopolymer matrix comprises a plurality of physically self-assembled CarHc polymers that exhibit a rapid gel-sol transition (gelation or change from a liquid state to a gel state) on light exposure, which enabled the facile release/recovery of cells from 3D cultures while maintaining their viability. The light-responsive hydrogel biopolymer matrix can establish an elastic network with "solid" like properties (where the Young's Modulus is greater than zero) or a hydrogel in the presence of adenosylcobalamin in the dark, and the elastic molecular network disassembles or undergoes solid-to-liquid (so-lq) transition under a light condition with wavelength ranging from about 300 nm to about 600 nm. The light-responsive hydrogel biopolymer matrix can further comprise one or more chromophore (such as cobalamin derivatives like cyanocobalamin, hydroxocobalamin, methylcobalamin, and/or any other chemically modified cobalamin) and/or one or more a chromophore-hosting protein that comprises a part of CarH with a chromophore. The light-responsive hydrogel biopolymer matrix can also encapsulate and release bulky globular proteins, such as mCherry, in a light-dependent manner. Such direct assembly of stimuli-responsive proteins into a light-responsive hydrogel biopolymer matrix represents a versatile strategy for designing dynamically tunable materials.

One of the technological advantages of the light-responsive hydrogel biopolymer matrix and hydrogels comprising a light-responsive hydrogel biopolymer matrix is that it requires no chemical modification to achieve light-responsiveness. This is a grand departure from existing synthetic polymer-based hydrogels that rely on synthetic light-responsive moieties and chemical modification, as well as existing protein hydrogels that have no light-responsiveness function. Further, the cell culture and release platform generated by the light-responsive hydrogel biopolymer matrix enables facile cell release with non-invasive protocol-based on light while preserving the advantages of extracellular matrix (ECM) protein-based platform, including similarities in chemical and biological compositions.

In some aspects, this disclosure relates to a light-responsive hydrogel biopolymer matrix which can comprise:
  (a) one or a plurality of light-responsive gelation initiator complexes connected to one or a plurality of a first extracellular matrix protein fragments, and
  (b) two or more cross-linkable proteins connected to one or a plurality of a second extracellular matrix protein fragments.

In some aspects, this disclosure relates to a light-responsive hydrogel biopolymer matrix where the light-responsive gelation initiator complex can comprise a protein photoreceptor.

In some aspects, this disclosure relates to a light-responsive hydrogel biopolymer matrix which can comprise one or a plurality of light-responsive gelation initiator complexes comprising a protein photoreceptor CarHc and a multi-dentate ligand adenosylcobalamin, connected to one or a plurality of a first extracellular matrix protein fragments, and two or more cross-linkable proteins connected to one or a plurality of a second extracellular matrix protein fragments, where the first extracellular matrix protein fragments and second extracellular matrix protein fragments are independently selected from elastin fragments which comprise a repeating polypeptide having the sequence of $(VPGXG)_n$ (SEQ ID NO: 18), wherein X represents valine or glutamate, the ratio of valine to glutamate ranges from 100:1 to 1:100, n is an integer selected from 1 to 50, the two or more cross-linkable proteins are SpyTag and SpyCatcher, and the matrix is responsive to light comprising a wavelength from about 300 nm to about 600 nm.

In some aspects, the light-responsive hydrogel biopolymer matrix further comprises a first telechelic biopolymer which can comprise a first light-responsive gelation initiator complex covalently bound to the first extracellular matrix protein fragments which are covalently bound to a first two or more cross-linkable proteins, and a second telechelic biopolymer which comprises a second light-responsive gelation initiator complex covalently bound to the second extracellular matrix protein fragments which are covalently bound to a second two or more cross-linkable proteins.

In some aspects, said first telechelic biopolymer can be a recombinant protein encoding for the first light-responsive gelation initiator complex covalently bound to the first extracellular matrix protein fragments which are covalently bound to a first two or more cross-linkable proteins, and said second telechelic biopolymer can be a recombinant protein encoding for the second light-responsive gelation initiator complex covalently bound to the second extracellular matrix protein fragments which are covalently bound to a second two or more cross-linkable proteins.

In some aspects, the protein photoreceptor can be selected from: CarHc, light oxygen voltage sensing domain (LOV), photoactive yellow protein (PYP), phytochrome, and cytochrome. In some aspects, the protein photoreceptor is CarHc.

In some aspects, the light-responsive gelation initiator complex can further comprise a multi-dentate ligand. The multi-dentate ligand can include or exclude: adenosylcobalamin, cyanocobalamin, methylcobalamin, hydroxocobalamin, flavin, biliverdin, and streptavidin. In some aspects, the multi-dentate ligand can be adenosylcobalamin.

In some aspects, the first extracellular matrix protein fragments and second extracellular matrix protein fragments can be independently selected from fragments of: collagen, fibronectin, gelatin, elastin, immunoglobulin G-binding protein G (GB1), procollagen, and combinations thereof. In some aspects, the first extracellular matrix protein fragments and second extracellular matrix protein fragments are independently selected from fragments of elastin. The elastin fragments can comprise a repeating polypeptide having the sequence of $(VPGXG)_n$ (SEQ ID NO: 19), wherein X represents valine or glutamate, the ratio of valine to glutamate ranges from 100:1 to 1:100, and n is an integer between 1 to 100. In some aspects, the ratio of valine to glutamate can range from 10:1 to 1:10. In some aspects, the ratio of valine to glutamate is 4:1. In some aspects, n is an integer between 1 to 10. In some aspects, n is 15.

In some aspects, the two or more cross-linkable proteins can be selected from: SpyTag and SpyCatcher, SnoopTag and SnoopCatcher, SdyTag and SdyCatcher, Pilin-C and Pilin-N, Cpe0147-A and Cpe0147-B, CL7 and Im7, and Strep-Tag and Streptavidin. In some aspects, the two or more cross-linkable proteins are SpyTag and SpyCatcher.

In some aspects, the matrix can be responsive to light with a wavelength from about 300 nm to about 600 nm. In some aspects, the matrix can be responsive to light with a wavelength of about 520 nm. In some aspects, the matrix can exhibit a phase transition from gel to solution upon exposure to light including but not limited to near-ultraviolet (<300 nm), visible (300-800 nm) and/or near-infrared light (>800 nm). In some aspects, the light-responsive gelation initiator complex can comprise the protein photoreceptor CarHc, the light-responsive gelation initiator complex further comprises the multi-dentate ligand adenosylcobalamin, the first extracellular matrix protein fragments and second extracellular matrix protein fragments are independently selected from elastin fragments which comprise a repeating polypeptide having the sequence of $(VPGXG)_n$ (SEQ ID NO: 20), wherein X represents valine or glutamate, the ratio of valine to glutamate is 4:1, and n is 15, the two or more cross-linkable proteins are SpyTag and SpyCatcher, and the matrix is responsive to light with a wavelength from about 300 nm to about 600 nm.

In some aspects, a first telechelic biopolymer can comprise a first light-responsive gelation initiator complex covalently bound to the first extracellular matrix protein fragments which are covalently bound to a first two or more cross-linkable proteins, and a second telechelic biopolymer can comprise a second light-responsive gelation initiator complex covalently bound to the second extracellular matrix protein fragments which are covalently bound to a second two or more cross-linkable proteins.

In some aspects, the first telechelic biopolymer can be a recombinant protein encoding for the first light-responsive gelation initiator complex covalently bound to the first extracellular matrix protein fragments which are covalently bound to a first two or more cross-linkable proteins, and the second telechelic biopolymer can be a recombinant protein encoding for the second light-responsive gelation initiator complex covalently bound to the second extracellular matrix protein fragments which are covalently bound to a second two or more cross-linkable proteins.

In some aspects, the first telechelic biopolymer and second telechelic biopolymer independently can have the linkage structure selected from: CarHc-elastin-CarHc or CarHc-elastin-CarHc-elastin-CarHc. In some aspects, the first telechelic biopolymer and second telechelic biopolymer independently can have the linkage structure selected from: SpyTag-CarHc-SpyTag, SpyCatcher-CarHc-SpyCatcher, SpyTag-CarHc-SpyCatcher, Spy-Tag-CarHc, SpyCatcher-CarHc, and CarHc-CL7.

In some aspects, the first telechelic biopolymer and second telechelic biopolymer independently can have the linkage structure selected from: SpyTag-elastin-CarHc-elastin-SpyTag, SpyCatcher-elastin-CarHc-elastin-SpyCatcher, SpyTag-elastin-CarHc-elastin-SpyCatcher, SpyTag-elastin-CarHc, SpyCatcher-elastin-CarHc, CarH$_c$-ELP-RGD-ELP-CarH$_c$, and CarHc-elastin-CL7.

In some aspects, the light-responsive hydrogel biopolymer matrix can further comprise a cell. In some aspects, the cell can be a mammalian cell. In some aspects, the mammalian cell can be a fibroblast or a stem cell. The stem cell can be a mesenchymal stem cell (hMSC).

In some aspects, the light-responsive hydrogel biopolymer matrix can further comprise an non-covalently bound protein. The non-covalently bound protein can be selected from therapeutic protein, cytokine, or a fluorescent protein. In some aspects, the fluorescent protein can be mCherry, GFP, RFP, YFP, CFP and/or any other genetically encoded fluorescent molecule. In some aspects, the therapeutic protein can be an antibody.

In some aspects, the light-responsive hydrogel biopolymer matrix can further comprise water. The water content of the hydrogel can be in the range from 70% to 99.5% (w/w). In some aspects, the protein photoreceptor content of the hydrogel can be in the range from 0.001% to 0.5% (w/w).

In some aspects, this disclosure relates to an oligonucleotide sequence which can encode a linkage structure selected from: CarHc-elastin-CarHc, CarHc-elastin-CarHc-elastin-CarHc, SpyTag-CarHc-SpyTag, SpyCatcher-CarHc-SpyCatcher, SpyTag-CarHc-SpyCatcher, SpyTag-CarHc, SpyCatcher-CarHc, CarHc-CL7, SpyTag-elastin-CarHc-elastin-SpyTag, SpyCatcher-elastin-CarHc-elastin-SpyCatcher, SpyTag-elastin-CarHc-elastin-SpyCatcher, SpyTag-elastin-CarHc, SpyCatcher-elastin-CarHc, and CarHc-elastin-CL7.

In some aspects, the oligonucleotide can comprise a sequence selected from SEQ ID NO:1, or SEQ ID NO: 2. In some aspects, the oligonucleotide sequence can have higher than 80%, 90%, 95%, 96%, 97%, 97.5%, 98%, or 99% homology to either that of SEQ ID NO:1 or SEQ ID NO: 2.

In some aspects, this disclosure relates to a vector which can comprise one or more oligonucleotide sequences which encode a linkage structure selected from: CarHc-elastin-CarHc, CarHc-elastin-CarHc-elastin-CarHc, SpyTag-CarHc-SpyTag, SpyCatcher-CarHc-SpyCatcher, SpyTag-CarHc-SpyCatcher, SpyTag-CarHc, SpyCatcher-CarHc, CarHc-CL7, SpyTag-elastin-CarHc-elastin-SpyTag, SpyCatcher-elastin-CarHc-elastin-SpyCatcher, SpyTag-elastin-CarHc-elastin-SpyCatcher, SpyTag-elastin-CarHc, SpyCatcher-elastin-CarHc, and CarHc-elastin-CL7. In some aspects, this disclosure relates to a plasmid comprising said vector.

In some aspects, this disclosure relates to a method for producing a light-responsive hydrogel biopolymer matrix, where the method can comprise dissolving one or a plurality of light-responsive gelation initiator complexes connected to one or a plurality of a first extracellular matrix protein fragments and two or more cross-linkable proteins connected to one or a plurality of a second extracellular matrix protein fragments in an aqueous solution to form a gelation mixture wider light which does not comprise a wavelength of less than about 600 nm, where the light-responsive gelation initiator complex comprises the protein photoreceptor CarHc, the light-responsive gelation initiator complex further comprises the multi-dentate ligand adenosylcobalamin, the first extracellular matrix protein fragments and second extracellular matrix protein fragments are independently selected from elastin fragments which comprise a repeating polypeptide having the sequence of $(VPGXG)_n$, (SEQ ID NO: 20), wherein X represents valine or glutamate, the ratio of valine to glutamate is 4:1, and n is 15, and the two or more cross-linkable proteins are SpyTag and SpyCatcher.

In some aspects, this disclosure relates to a method of encapsulating cells in a photoresponsive hydrogel matrix, where the method can comprise the steps of: (a) dissolving one or more cells in an aqueous solution, (b) dissolving one or a plurality of light-responsive gelation initiator complexes connected to one or a plurality of a first extracellular matrix protein fragments and two or more cross-linkable proteins connected to one or a plurality of a second extracellular matrix protein fragments in the aqueous solution comprising one or more cells to form a gelation mixture under light which does not comprise a wavelength of less than about 600 nm, where the light-responsive gelation initiator complex comprises the protein photoreceptor CarHc, the light-responsive gelation initiator complex further comprises the multi-dentate ligand adenosylcobalamin, the first extracellular matrix protein fragments and second extracellular matrix protein fragments are independently selected from elastin fragments which comprise a repeating polypeptide having the sequence of $(VPGXG)_n$ (SEQ ID NO: 20), wherein X represents valine or glutamate, the ratio of valine to glutamate is 4:1, and n is 15, and the two or more cross-linkable proteins are SpyTag and SpyCatcher. In some aspects, the method can further comprise the steps of: (c) contacting the gelation mixture with cell growth media to form a gelation growth media, and (d) incubating the gelation growth media to form incubated gelation growth media. In some aspects, the method can further comprise the step of: (e) irradiating the incubated gelation growth media with light comprising a wavelength between about 300 nm and about 600 nm to transform the hydrogel into a liquid.

Altogether the present study provides evidence for culturing cells in vitro using light-sensitive protein hydrogels of this disclosure.

BRIEF DESCRIPTION OF DRAWINGS

The patent or application file contains at least one drawing executed in color. Copies of this patent or patent application publication with color drawing(s) will be provided by the U.S. Patent and Trademark Office upon request and payment of the necessary fee.

FIG. 1A shows the synthesis of photoresponsive CarHc hydrogel, where light exposure dissembles tetrameric CarHc accompanied by the degradation of AdoB12, the release of 4',5'-anhydroadenosine, and the coordination of His132 to the metal center. Tetrameric CarHc is Protein Data Bank ID code 5C8A. Telechelic biopolymer is CarHc (Protein Data Bank ID code 5C8F).

FIG. 1B shows the two telechelic recombinant proteins, ACA and BCB, which are co-polymerized through SpyTag-SpyCatcher chemistry. The resulting polymers can further be assembled into a molecular network through AdoB12-induced CarHc tetramerization in the dark and dissembled on light exposure. ApoCarHc is the CarHc protein without AdoB12.

FIG. 2A shows AdoB12-dependent photoresponsiveness of CarHc hydrogels of the present disclosure, including where evolution of the storage modulus G' and loss modulus G" of ACA+BCB in the presence and absence of AdoB12 at room temperature (25° C.) in the dark (without light from a wavelength between about 300 nm and about 600 nm) as a function of time.

FIG. 2B shows the gel-sol (hydrogel to aqueous solution) phase transition induced by light having a wavelength between about 300 nm and about 600 nm. Upon white light exposure (at an intensity of 30 klux), the G' and G" of the CarHc hydrogel were monitored at a fixed shear frequency of 1 rad/sec and strain of 5%.

FIG. 2C shows the gel-sol transition rates of the CarHc hydrogels are affected by light intensity. The normalized storage modulus $(G'/G'_o)$ of the materials exposed to the 30- and 90-klux lights is compared. The G' values corresponding to the 30-klux light exposure were from the same measurement show in FIG. 2B.

FIG. 2D shows the response of the CarHc hydrogel toward pulsed light (90 klux). Exponential decay cure fitting was used.

FIG. 14A shows the time-sweep measurements performed in the dark with the strain fixed at 5% on the physically self-assembled light-sensitive protein hydrogels comprising CarHc composed of the linkage structure AAA+BCB+AdoB12 at room temperature in the dark.

FIG. 14B shows the frequency-sweep measurements performed in the dark with the frequency fixed at 1 rad/sec on the physically self-assembled light-sensitive protein hydrogels comprising CarHc composed of the linkage structure AAA+BCB+AdoB12 at room temperature.

FIG. 14C shows the strain-sweep measurements performed in the dark with the strain fixed at 5% on the physically self-assembled light-sensitive protein hydrogels comprising CarHc composed of the linkage structure ACA+BCB+AdoB12 at room temperature.

FIG. 18 shows the stability of the covalently cross-linked light-sensitive polymer hydrogel comprising CarHc comprised of the linkage structure AAA+BCB+AdoB12, toward the TEV protease under dark and bright (white LED light comprising a wavelength between about 300 nm and about 600 nm) at 90 klux. The hydrogels (8.6% (w/w), 20 uL) were treated with TEV (2.5 mg/mL, 120 uL in PBS) at room temperature for 12 h. The hydrogels were resistant toward TEV digestion under both dark (no wavelength between about 300 nm and about 600 nm) and bright light (with a wavelength between about 300 nm and about 600 nm) conditions. The hydrogel in the tube exposed to light (with wavelength between about 300 nm and about 600 nm) is not observable even after adjusting contrast and brightness. Error bars show SDs from three independent experiments.

FIG. 19A shows the polynucleotide sequence information of the linkage structure BCB (SEQ ID NO: 1).

FIG. 19B shows the polypeptide sequence information of the linkage structure BCB (SEQ ID NO: 2). The segments in red and green are SpyCatcher and CarHc, respectively. The underlined segments are TEV protease cutting sites.

FIG. 20A shows polynucleotide the sequence information of the linkage structure ACA (SEQ ID NO: 3).

FIG. 20B shows the polypeptide sequence information of the linkage structure ACA (SEQ ID NO: 4). The segments in red and green are SpyTag and CarHc, respectively.

FIG. 21A shows the polynucleotide sequence information of the linkage structure mCherry-CarHc (SEQ ID NO: 5).

FIG. 24A shows the live/dead stain of cells released once.

FIG. 24B shows the live/dead stain of cells further encapsulated in a new piece of hydrogel then released again.

FIG. 25A shows the linkage construct of another embodiment of the present disclosure, where CarHc serves as both a photo-crosslinkable protein and a light-sensitive gelation initiator in the presence of AdoB12.

FIG. 25B shows the frequency- and strain-sweep tests on the physically self-assembled photosensitive protein hydrogels comprising a linkage construct of $CarH_C$-Elp-RGD-Elp-$CarH_C$ in the presence of $AdoB_{12}$ in the dark (no light between about 300 nm and about 600 nm), indicating gelation formation.

FIG. 25C shows the frequency- and strain-sweep tests on the hydrogel in the presence of light comprising a wavelength from about 300 nm and about 600 nm at an intensity of 90 klux, indicating the gel-to-sol liquid phase transition.

FIG. 26A shows the linkage construct of the nucleotide sequence of AA (SpyTag-Elastin Protein-SpyTag) (SEQ ID NO: 7).

FIG. 26B shows the linkage construct of the polypeptide sequence of AA (SEQ ID NO: 8).

FIG. 27A shows the linkage construct of the nucleotide sequence of AAA (SpyTag-Elastin Protein-SpyTag-Elastin Protein-SpyTag) (SEQ NO: 9).

FIG. 27B shows the linkage construct of the polypeptide sequence of AAA (SEQ ID NO: 10).

FIG. 28A shows the linkage construct of the nucleotide sequence of BB (SpyCatcher-Elastin Protein-SpyCatcher) (SEQ ID NO: 11).

FIG. 28B shows the linkage construct of the polypeptide sequence of BB (SEQ ID NO: 12).

FIG. 29 shows the summary of the plasmid constructs, primers, and sources of manufacture of the polynucleotides used in this study. "His6" is disclosed as SEQ ID NO: 25.

DETAILED DESCRIPTION

Figure 3B:
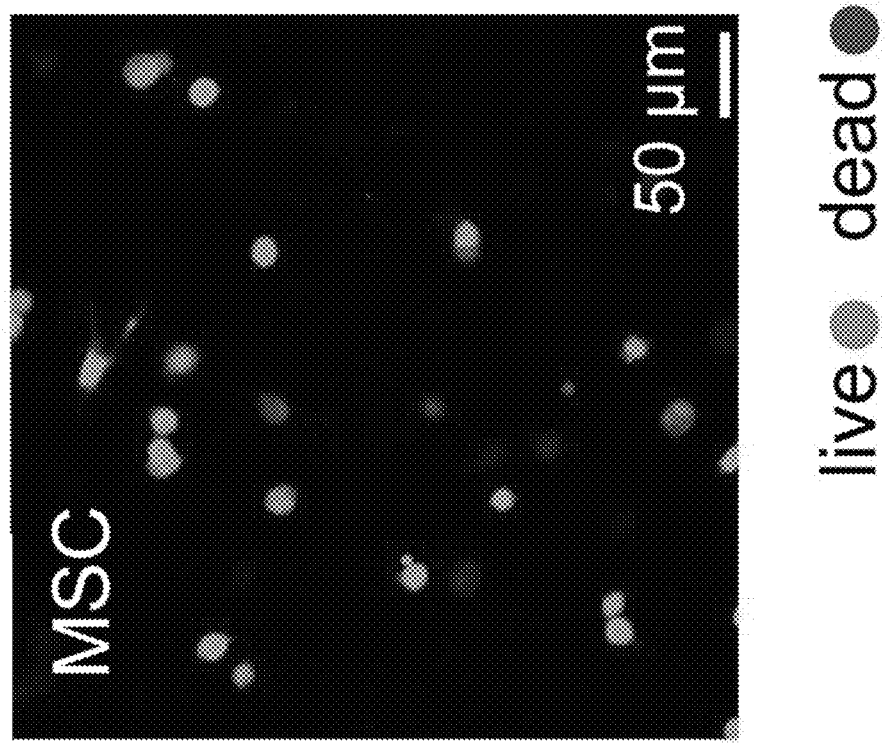
FIG. 3B shows the encapsulation of MSCs by the same motif mentioned above. Representative confocal fluorescence z-slice micrographs of live (green; calcein AM) and dead (red; ethidium homodimer) cells.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The practice of the present disclosure will employ, unless otherwise indicated, conventional techniques of molecular biology, microbiology, recombinant DNA, and immunology, which are within the skill of the art. Such techniques are explained fully in the literature. See, e.g., Molecular Cloning A Laboratory Manual, 2nd Ed., ed. by Sambrook, Fritsch and Martians (Cold Spring Harbor Laboratory Press, 1989); DNA Cloning, Volumes I and II (D. N. Glover ed., 1985);

Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods in Enzymology, Vols. 154 and 155 (Wu et al. eds), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

Conventional release media used in cell culture often lack versatility in that a given medium, such as a substrate suitable for cell culture, and therefore will often not be a suitable medium for use in other applications such as confined protein release.

The present invention provides for light-sensitive protein hydrogels made of recombinant proteins that can be used as substrates for cell culture and cell release. The present invention also demonstrates the successful polymerization of the elastin-like polypeptide (ELP)-fusion $CarH_C$ protein using SpyTag-SpyCatcher chemistry. $CarH_C$ tetramerization in the presence of AdoB12 in the dark eventually led to the formation of a hydrogel that can undergo a rapid gel-sol transition on light exposure. The $CarH_C$ domains tetramerize when binding to adenosylcobalamin (AdoB12) in the dark and can readily dissociate into monomers accompanied with a drastic protein conformational change caused by the cleavage of the C—Co bond on exposure to green (522 nm) or white light (FIG. 1A.). This result illustrates a versatile strategy for developing stimuli-responsive protein materials for biomedical applications, such as controlled therapeutic release and cell recovery, from 3D cultures.

Definitions

As used herein, the term "composition" refers to a product comprising one or more ingredients.

As used herein, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As will be appreciated, a "fragment" of a protein may be a form of the protein truncated at the amino terminus, the carboxy terminus, and/or internally (such as by natural splicing), and may also be variant and/or derivative. A "domain" of a protein is also a fragment, and comprises the amino acid residues of the protein required to confer biochemical activity corresponding to naturally occurring protein. Truncated molecules that are linear biological polymers such as nucleic acid molecules or polypeptides may have one or more of a deletion from either terminus of the molecule and/or one or more deletions from a non-terminal region of the molecule, where such deletions may be deletions of from about 1-1500 contiguous nucleotide or amino acid residues, preferably about 1-500 contiguous nucleotide or amino acid residues and more preferably about 1-300 contiguous nucleotide or amino acid residues, including deletions of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41-50, 51-74, 75-100, 101-150, 151-200, 201-250 or 251-299 contiguous nucleotide or amino acid residues.

As used herein, the term "vector" refers to a nucleic acid molecule amplification, replication, and/or expression vehicle in the form of a plasmid, phage, viral, or other system (be it naturally occurring or synthetic) for the delivery of nucleic acids to cells where the plasmid, phage, or virus may be functional with bacterial, yeast, invertebrate, and/or mammalian host cells. The vector may remain independent of host cell genomic DNA or may integrate in Whole or in part with the genomic DNA. The vector will generally but need not contain all necessary elements so as to be functional in any host cell it is compatible with. An "expression vector" is a vector capable of directing the expression of an exogenous polynucleotide, for example, a polynucleotide encoding a binding domain fusion protein, under appropriate conditions.

As used herein, the term "percent (%) homology" refers to the percentage of sequence similarity found in a comparison of two or more sequences. Percent identity can be determined, electronically using any suitable software.

As described herein, the term "homology" includes polynucleotides that may be a homologue of sequence in the oligonucleotide encoding for the described linkage structures (e.g. DNA), Such polynucleotides typically have at least about 70% homology, preferably at least about 70%, 75%, 80%, 85%, 86%, 87%, 88%, 89%, 90%, 91%, 922/6, 93%, 94%, 95%, 96%, 97%, 97.5%, 98%, 99% or higher homology with the relevant sequence, for example over a region of at least about 15, 20, 30, 40, 50, 100 more contiguous nucleotides (of the homologous sequence).

Homology may be calculated based on any method in the art. For example the UWGCG Package provides the BEST-FIT program which can be used to calculate homology (for example used on its default settings) (Devereux et al. (1984) Nucleic Acids Research 12, p 387-395). The PILEUP and BLAST algorithms can be used to calculate homology or line up sequences (typically on their default settings), for example as described in Altschul S. F. (1993); J Mol Evol 36: 290-300; Altschul, S. F. et al.; (1990); J Mol Biol 215: 403-10. Software for performing BLAST analyses is publicly available through the National Center for Biotechnology Information (http://www.ncbi.nlm.nih.gov/L). This algorithm involves first identifying high scoring sequence pair by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence is less than about 1, preferably less than about 0.1, more preferably less than about 0.01, and most preferably less than about 0.001.

The homologous sequence typically differs from the relevant sequence by at least (or by no more than) about 1, 2, 5, 10, 15, 20 or more mutations (which may be substitutions, deletions or insertions). These mutations may be measured across any of the regions mentioned above in relation to calculating homology. The homologous sequence typically hybridizes selectively to the original sequence at a level significantly above background.

As used herein, the term "cell" refers to any living cell suitable for the desired application. Cells include eukaryotic and prokaryotic cells.

In some embodiments of the methods and combinations described herein, the eukaryotic cells are mammalian cells. In some embodiments, the eukaryotic cells are human cells. In other embodiments, the eukaryotic cells are non-mammalian cells, which can include or exclude insect or yeast cells.

Mammalian cells that may be captured, cultured, or released by the methods or compositions described herein can include or exclude the following cell types: cells of the integumentary system: keratinizing epithelial cells, epidermal, epidermal basal cell, keratinocyte of fingernails and toenails, nail bed basal cell, medullary hair shaft cell, cortical hair shaft cell, cuticular hair shaft cell, cuticular hair root sheath cell, hair root sheath cell of huxley's layer, hair root sheath cell of Henle's layer, external hair root sheath cell, and hair matrix cell; wet stratified barrier epithelial cells: surface epithelial cell of stratified squamous epithelium of cornea, tongue, oral cavity, esophagus, anal canal, distal urethra and vagina; basal cell of epithelia of cornea, tongue, oral cavity, esophagus, anal canal, distal urethra and vagina; urinary epithelium cell; gland cells: exocrine secretory epithelial cells: salivary gland mucous cell, salivary gland serous cell, von Ebner's gland cell in tongue, mammary gland cell, lacrimal gland cell, ceruminous gland cell in ear, eccrine sweat gland dark cell, eccrine sweat gland clear cell, apocrine sweat gland cell, gland of moll cell in eyelid, sebaceous gland cell, Bowman's gland cell in nose, Brunner's gland cell in duodenum, seminal vesicle cell, prostate gland cell, bulbourethral gland cell, Bartholin's gland cell, gland of hare cell, uterus endometrium cell, isolated goblet cell of respiratory and digestive tracts, stomach lining mucous cell, gastric gland zymogenic cell, gastric gland oxyntic cell, parietal cell, enterochromaffin like (ecl) cells, pancreatic acinar cell, paneth cell of small intestine, type ii pneumocyte of lung, and clara cell of lung; hormone secreting cells: anterior pituitary cells: somatotropes, lactotropes, thyrotropes, gonadotropes, corticotropes, intermediate pituitary cell, secreting melanocyte-stimulating hormone, magnocellular neurosecretory cells, secreting oxytocin, secreting vasopressin, and gut and respiratory tract cells; cells included in islets of langerhans: alpha cell, beta cells, delta cells, pp cells (produce pancreatic polypeptide), epsilon cells, thyroid gland cells, thyroid epithelial cell, parafollicular cell, parathyroid gland cells, parathyroid chief cell, oxyphil cell, adrenal gland cells, chromaffin cells, Leydig cell of testes, theca interna cell of ovarian follicle, corpus luteum cell of ruptured ovarian follicle, granulosa lutein cells, Theca lutein cells, juxtaglomerular cell, macula densa cell of kidney, peripolar cell of kidney, and mesangial cell of kidney; metabolism and storage cells: hepatocyte (liver cell), white fat cell (adipocytes/blasts), brown fat cell, and liver lipocyte cells; barrier function cells (lung, gut, exocrine glands and urogenital tract); kidney cells: kidney glomerulus parietal cell, kidney glomerulus podocyte, kidney proximal tubule brush border cell, loop of henle thin segment cell, kidney distal tubule cell, and kidney collecting duct cell; other barrier function cell types: type i pneumocyte, pancreatic duct cell (centroacinar cell), nonstriated duct cell, principal cell, intercalated cell, duct cell, intestinal brush border cell (with microvilli), exocrine gland striated duct cell, gall bladder epithelial cell, ductulus efferens nominated cell, epididymal principal cell, and epididymal basal cell; epithelial cells lining closed internal body cavities: microvascular endothelial cells, blood vessel and lymphatic vascular endothelial fenestrated cell, blood vessel and lymphatic vascular endothelial continuous cell, blood vessel and lymphatic vascular endothelial splenic cell, synovial cell, serosal cell, squamous cell columnar cell of endolymphatic sac with microvilli, columnar cell of endolymphatic sac without microvilli, dark cell (lining endolymphatic space of ear), vestibular membrane cell (lining endolymphatic space of ear), stria vascularis basal cell (lining endolymphatic space of ear), stria vascularis marginal cell (lining endolymphatic space of ear), cell of claudius (lining endolymphatic space of ear), cell of Boettcher (lining endolymphatic space of ear), choroid plexus cell, pia-arachnoid squamous cell, pigmented ciliary epithelium cell of eye, nonpigmented ciliary epithelium cell of eye, corneal endothelial cell, and peg cell (of fallopian tube); ciliated cells with propulsive function: respiratory tract ciliated cell, oviduct ciliated cell, uterine endometrial ciliated cell, rete testis ciliated cell, ductulus efferens ciliated cell, and ciliated ependymal cell of central nervous system; extracellular matrix secretion cells: ameloblast epithelial cell, planum semilunatum epithelial cell of vestibular apparatus of ear, organ of corn interdental epithelial cell, loose connective tissue fibroblasts, corneal fibroblasts (corneal keratocytes), tendon fibroblasts, bone marrow reticular tissue fibroblasts, pericyte, nucleus pulposus cell of intervertebral disc, ementoblast/cementocyte, odontoblast/odontocyte, hyaline cartilage chondrocyte, fibrocartilage chondrocyte, elastic cartilage chondrocyte, osteoblast/osteocyte, osteoprogenitor cell (stem cell of osteoblasts), hyalocyte of vitreous body of eye, stellate cell of perilymphatic space of ear, hepatic stellate cell (Ito cell), and pancreatic stellate cell; contractile cells: skeletal muscle cells, red skeletal muscle cell (slow), white skeletal muscle cell (fast), intermediate skeletal muscle cell, nuclear bag cell of muscle spindle, nuclear chain cell of muscle spindle, satellite cell, heart muscle cells, ordinary heart muscle cell, nodal heart muscle cell, purkinje fiber cell, smooth muscle cell, myoepithelial cell of iris, and myoepithelial cell of exocrine glands; blood and immune system cells: megakaryocyte (platelet precursor), monocyte, connective tissue macrophage, epidermal langerhans cell, osteoclast (in bone), dendritic cell, microglial cell (in central nervous system), neutrophil granulocyte, eosinophil granulocyte, basophil granulocyte, mast cell, helper T cell, suppressor T cell, cytotoxic T cell, natural killer T cell, B cell, natural killer cell, reticulocyte, megakaryocyte, and myeloblast; cells of the nervous system: sensory transducer cells: auditory inner hair cell of organ of corti, auditory outer hair cell of organ of corti, basal cell of olfactory epithelium, cold-sensitive primary sensory neurons, heat-sensitive primary sensory neurons, merkel cell of epidermis, olfactory receptor neuron, pain-sensitive primary sensory neurons, photoreceptor cells of retina in eye: photoreceptor rod cells, photoreceptor blue-sensitive cone cell of eye, photoreceptor green-sensitive cone cell of eye, and photoreceptor red-sensitive cone cell of eye; proprioceptive primary sensory neurons, touch-sensitive primary sensory neurons, type I carotid body cell, type II carotid body cell, type I hair cell of vestibular apparatus of ear, type II hair cell of vestibular apparatus of ear, and type I taste bud cell; autonomic neuron cells: cholinergic neural cell, adrenergic neural cell, and peptidergic neural cell; sense organ and peripheral neuron supporting cells: inner pillar cell of organ of corti, outer pillar cell of organ of corti, inner phalangeal cell of organ of corti, outer phalangeal cell of organ of corti, border cell of organ of corti, Hensen cell of organ of corti, vestibular apparatus supporting cell, taste bud supporting cell, olfactory epithelium supporting cell, Schwann cell, andenteric glial cell; central nervous system neurons and glial cells: astrocyte, neuron cells, oligodendrocyte, spindle neuron, and pineocyte; lens cells: anterior lens epithelial cell, crystallin-containing lens fiber cell, pigment cells, melanocyte, retinal pigmented epithelial cell, germ cells, oogoniurriloocyte, spermatid, spermatocyte, spermatogonium cell, spermatozoon, nurse cells, ovarian follicle cell, sertoli cell, and thymus epithelial cell; stem cells and progenitor cells: embryonic stem cells, adult stem cells (including hematopoietic stem cells, endothelial stem cells, epithelial stem cells, neural stem cells, mesenchymal stem cells), progenitor cells (neural progenitor cells, lymphoid progenitor cells, satellite cells, endothelial progenitor cells, periosteal progenitor, pancreatic progenitor cells, satellite cells in muscles, hematopoietic progenitor cells), amniotic stem cells (multipotent and can differentiate to cells of adipogenic, osteogenic, myogenic, endothelial, hepatic and also neuronal lines), and induced pluripotent stem cells.

As used herein, the term "stem cells" has its ordinary meaning in the art and includes embryonic stems cells and induced pluripotent stem cells. As used herein, embryonic stem cells are pluripotent cells isolated from the inner cell mass of blastocysts and can be propagated in vitro. These cells can differentiate into any cell type in the body. Embryonic stem cells described herein therefore have been isolated from their natural environment. Embryonic stem cells described herein have been physically separated from the blastocyst. In some embodiments, the embryonic stem cells are untransfected. In certain embodiments, the embryonic stem cells are human embryonic stem cells.

As used herein, the term "cross-linkable proteins" refers to two separate proteins which form an association. In some embodiments, the association is a covalent bond. In some embodiments, the association is a non-covalent bond. In some embodiments, the non-covalent bond has a dissociation constant of less than 100 micromolar. In some embodiments, the non-covalent bond has a dissociation constant of less than 50 micromolar. In some embodiments, the non-covalent bond has a dissociation constant of less than 40 micromolar. In some embodiments, the non-covalent bond has a dissociation constant of less than 30 micromolar. In some embodiments, the non-covalent bond has a dissociation constant of less than 20 micromolar. In some embodiments, the non-covalent bond has a dissociation constant of less than 10 micromolar. In some embodiments, the cross-linkable proteins are selected from a recombinant protein encoding a linkage motif and a separate protein attached to the correspond ligand for the linkage motif. In some embodiments, the cross-linkable protein includes or excludes: SpyCatcher and SpyTag, CL7 and Im7, SnoopTag and SnoopCatcher (the engineered adhesin RrgA from *Streptococcus pneumonia*), SdyTag and SdyCatcher (the engineered pair from a related fibronectin-binding Cna protein B-type (CnaB) domain in *Streptococcus dysgalactiae*), Pilin-C and Pilin-N (engineered pilin subunits from human *Streptococcus pyogenes*), Cpe0147-A and Cpe0147-B (engineered putative MSCRAMM from the Gram-positive pathogen *Clostridium perfringens*), CarHc and CarHc in the presence of a photosensitive protein, Strep-tag and Streptavidin, Strep-tag and Strep-tactin™, SNAP and SNAP-tag, FLAG and FLAG-tag, CLIP and CLIP-tag, HALO, and HALO-tag, ACP, MCP, LUMIO, c-Myc, CBP (calmodulin-binding peptide), and combinations thereof.

SpyCatcher and SpyTag are formed by splitting the second immunoglobulinlike collagen adhesin domain (CnaB2) of the fibronectin-binding protein (FbaB) of *Streptococcus pyogenes* (Zakeri, etas., Proc. Natl. Acad. Sci. USA, E690-E697, (2012)). SpyTag-SpyCatcher chemistry forms a specific isopeptide bond between Asp-117 of SpyTag and Lys-31 of SpyCatcher on protein binding under mild physiological conditions (Sun, et al, Proc. Natl. Acad. Sci. USA, 111:11269-11274 (2014)). The SpyCatcher-SpyTag chemistry is highly efficient and modular, where each of the distinct protein parts, SpyCatcher, and SpyTag, can be incorporated into separate polypeptides for binding the two polypeptides together.

Mutated Colicin E7 DNase (CL7) and its inhibitor, Immunity protein 7 (Im7) are two polypeptide pairs with high mutual affinity (Kd=$10^{-14}$ to $10^{-17}$ M). The mutated CL7 tag retains the full binding affinity to Im7 but is inactivated as a DNase (Marina, et al., Proc. Natl. Acad. Sci., 114 (26) E5138-E5147 (2017)), Each of the distinct polypeptide parts, CL7, and Im7, can be recombinantly incorporated into separate polypeptides for binding the two polypeptides together.

Strep-tag (IBA Life Sciences) and Streptavidin, or Strep-tag and Strep-tactin™ (IBA Life Sciences), are two sets of protein pairs with mutual affinity. Strep-tag is a polypeptide consisting of eight amino acids in the sequence of: Trp-Ser-His-Pro-Gln-Phe-Glu-Lys (SEQ ID NO: 21). Each of the distinct polypeptide parts, Strep-tag, and Streptavidin or Step-tactin, can be reombinamly incorporated into separate polypeptides for binding the two polypeptides together. Streptavidin is a multi-dentate ligand, where it can bind to one to four moieties, albeit with decreasing affinity constants. In some embodiments, Strep-tag can be incorporated into separate terminae of separate telechelic polypeptides, and the two polypeptides joined through their mutual binding to Streptavidin.

In some embodiments, CarHc and CarHc can be cross-linked together in the presence of $AdoB_{12}$ or other photosensitive protein. In some embodiments, two different CarHc moieties are on separate telechelic biopolymer polypeptides which are to be crosslinked. In some embodiments, the linkage construct is $CarH_C$-ELP-RGD-ELP-$CarH_C$. This photosensitive protein hydrogel construct has the advantage of having the fewest functional components because the CarHc moieties act as both cross-linkable proteins and light-responsive gelation initiators. FIGS. 25B & 25C show the frequency and strain-sweep tests on the physically self-assembled protein hydrogel comprising linkage constructs of CarH$_C$-ELP-RGD-ELP-CarH$_C$ in the presence of AdoB$_{12}$ under both conditions of light comprising a wavelength between about 300 nm and 600 nm, and under dark (where no wavelength of light between about 300 nm and 600 nm is present). The results demonstrate that the CarHc moieties can be used as both the cross-linkable proteins and the light-responsive gelation initiators.

As used herein, the term "light-responsive gelation initiators" refers to a tetrameric complex comprising a protein photoreceptor and a multi-dentate ligand. In some embodiments, the multi-dentate ligand can include or exclude: adenosylcobalamin (AdoB$_{12}$), flavin, biliverdin, and methylcobalamin. In some embodiments, the multi-dentate ligand can include or exclude a cobalamin derivative. In some embodiments, the cobalamin derivative comprises a cobalamin moiety conjugated to a fluorophore. In some embodiments, the cobalamin derivative comprising a fluorophore is selected from Cbl1, Cbl2, Cbl3, Cbl4, Cbl5, Cbl6, Cbl-Bod, and coenzyme B$_{12}$ conjugates thereof.

In some embodiments, the C-terminal adenosylcobalmin binding domain of the CarH protein (CarH$_c$) tetramerize when binding to adenosylcobalamin (AdoB$_{12}$) in the dark and can readily dissociate into monomers accompanied with a drastic protein conformational change caused by the cleavage of the C—Co bond on exposure to green (522 nm) or white light (FIG. 1A). When the CarHc domains are covalently connected to cross-linkable proteins of telechelic polypeptides which are cross-linked, the secondary cross-linking of CarHc domains from separate telechelic polypeptides results in a cross-linked biopolymer. The recombinant proteins comprising a light-responsive photoreceptor, protein photoreceptor, and optionally protein cross-linkers, do not form a hydrogel when mixed in aqueous solution, and thus need cross-linking to a multi-dentate ligand. The cross-linking of the proteins can be realized by designing genetic expression cassettes (or vectors, or plasmids) where the proteins are assembled in a selected order in the form of encoding nucleotides, expressing in hosts harboring the cassettes, following with and purification from the expression system.

Without being bound by theory, the use of a light-responsive gelation initiator described herein enables the polymer strands to form a gel according to the classical statistical analysis of Carothers (Carothers, Trans. Faraday Soc. 32, 39 (1936)). The Carothers Equation states that a gel point is reached when the critical extent of reaction, $p_c$, of a monomer set having an average functionality (number of functional groups per monomer), $f_{avg}$, is $p_c = 2/f_{avg}$. As the number of functional groups per monomer increases, the critical extent of reaction to reach gelation decreases. The telechelic biopolymers having the linkage structure Spy[Tag or Catcher]-elastin-Spy[Tag or Catcher] described herein would comprise two functional groups when no CarHc moiety is present. The telechelic biopolymers having the linkage structure Spy[Tag or Catcher]-elastin-CarHc-elastin-Spy[Tag or Catcher] described herein would have three functional groups. A reaction comprising the latter telechelic biopolymer linkage structure would therefore gel at a lower extent of polymerization. Thus, not all of the cross-linking polymers need to react to form a hydrogel. In some embodiments, the light-sensitive protein hydrogels can comprise a mono-functional biopolymer, where only one terminae is functionalized with a cross-functional polymer. In some embodiments, the mono-functional biopolymer can have the linkage structure Spy[Tag or Catcher]-elastin-CarHc. Polymers with fewer cross-linking sites have larger pore sizes. In some embodiments, increasing the number of cross-linking sites in the hydrogel will result in small pore sizes, and decreasing the number of cross-linking sites in the hydrogel will result in larger pore sizes. Thus, including a mono-functional biopolymer in a reaction with one or more telechelic biopolymers would enable a higher gel point critical extent of reaction, which may be desired to capture larger cell sizes. Conversely, including a multi-functional telechelic biopolymer in a reaction would enable a lower gel point critical extent of reaction, which may be desired to capture smaller cell sizes or smaller protein sizes. In some embodiments, the telechelic biopolymers can have the linkage structure Spy[Tag or Catcher]-(elastin-CarHc)$_y$-elastin-Spy[Tag or Catcher], where y is 2 to 20 or higher, which would increase the average functionality of the reaction system resulting in a lower gel point critical extent of reaction.

As used herein, the term "protein photoreceptor" refers to a light-sensitive protein which reacts to light via photoisomerization or photoreduction, thus initiating a change of the receptor protein which triggers a functional effect upon irradiation with light of a selected wavelength. Protein photoreceptors can include or exclude: CarH, LOV (light oxygen voltage sensing domain), PYP (photoactive yellow protein), phytochrome, cytochrome, melanopsin, photopsin, rhodopsin, protein kinase C, OPN5, UVR8, cryptochrome, and phototropin. In some embodiments, the protein photoreceptor is CarH.

As used herein, the term "multi-dentate ligand" refers to a moiety with two or more attachment sites. In some embodiments, the multi-dentate ligand can include or exclude: any substituted corrin ring comprising a Cobalt atom (including adenosylcobalamin (AdoB$_{12}$) (also referred to as "5'-deoxyadenosylcobalamin"), cobalamin, aquocobalamin chloride, Co$_\beta$-Chloro-O5R-succinylcobalamin, Co$_\beta$-cyano-O5R-succinylcobalamin, Co$_\beta$-cyano-O5R-[3-(methoxycarbonyl)propionyl]cobalamin, Co$_\beta$-cyano-O5R-[3-(benzylcarboxamido)propionyl]cobalamin, Co$_\beta$-aquo-O5'-succinylcobalamin chloride, and Co$_\beta$-cyano-O5R-acetylcobalamin. In some embodiments, the multi-dentate ligand can include or exclude streptavidin. In some embodiments, the multi-dentate ligand interacts with two or more protein photoreceptors, where the protein photoreceptors are a component of a telechelic biopolymer, resulting in a light-sensitive cross-linking site (FIG. 1B).

As used herein, the term "linkage structure" refers to a linear polypeptide structure of a series of different functional moieties. The linkage structures described herein are recombinant proteins formed from the design of linked oligonucleotides encoding for each of the different functional moieties, where the expressed protein product is the linear polypeptide. In some embodiments, the linkage structure can comprise one or a plurality of cross-linking proteins at the terminae of the linkage structure. In some embodiments, the linkage structure can comprise one or a plurality of protein photoreceptors. In some embodiments, the linkage structure can comprise one or a plurality of extracellular matrix protein fragments. In some embodiments, the linkage structure can have a form selected from following linkage structures: CarHc-elastin-CarHc, CarHc-elastin-CarHc-elastin-CarHc, SpyTag-CarHc-SpyTag, SpyCatcher-CarHc-SpyCatcher, SpyTag-CarHc-SpyCatcher, SpyTag-CarHc, SpyCatcher-CarHc, CarHc-CL7, CarHc-Im7, SpyTag-elastin-CarHc-elastin-SpyTag, SpyCatcher-elastin-CarHc-elastin-SpyCatcher, SpyTag-elastin-CarHc-elastin-SpyCatcher, SpyTag-elastin-CarHc, SpyCatcher-elastin-CarHc, CarH$_C$-ELP-RGD-ELP-CarH$_C$, CarHc-elastin-CL7, SpyTag-elastin, SpyCatcher-elastin, SpyTag-elastin-SpyTag, SpyCatcher-elastin-SpyCatcher, SpyTag-elastin-SpyCatcher, SpyTag-(elastin-CarHc)$_y$-elastin-SpyTag, SpyCatcher-(elastin-CarHc)$_y$-elastin-SpyCatcher, and SpyTag-(elastin-CarHc)$_y$-elastin-SpyCatcher where y is an integer from 1 to 100.

As used herein, the terms "extracellular matrix protein fragment," and "extracellular matrix protein fragments" refers to one or more hydrophilic linker proteins which impart solubility and linear structure to the entity comprising the extracellular matrix protein fragment. In some embodiments, the extracellular matrix protein fragment is a fragment of laminin, collagen, fibronectin, gelatin, elastin, GB1 (immunoglobulin G-binding protein G), or procollagen. In some embodiments, the extracellular matrix protein fragment is a fragment of elastin. In some embodiments, the elastin extracellular matrix protein fragment comprises the polypeptide (VPGXG)$_n$, where X represents valine or glutamate. In some embodiments, the ratio of valine to glutamate ranges from 100:1 to 1:100. In some embodiments, the ratio of valine to glutamate ranges from 10:1 to 1:10. In some embodiments, the ratio of valine to glutamate is 4:1. In some embodiments, n is an integer between 1 to 100, In some embodiments, n is an integer between 1 to 50. In some embodiments, n is an integer between 1 to 40. In some embodiments, n is an integer between 1 to 30. In some embodiments, n is an integer between 1 to 20. In some embodiments, n is an integer between 5 to 20. In some embodiments, n is an integer between 10 to 20. In some aspects, n is 15.

As used herein, the terms "telechelic biopolymer," "telechelic recombinant protein," "telechelic polypeptide," and "telechelic protein" refers to a polypeptide where the N- and C-terminae are functionalized with one or more functional group moieties which can interact with another telechelic biopolymer. In some embodiments, the functional group moieties can be small molecule functional groups. In some embodiments, the small molecule functional groups can include an azido group and an alkynyl group (click chemistry), which can be cross-reacted via a catalysis, in some examples, a divalent cation (including Cu(II)), or a strained cyclic cyclooctynyl moiety. In some embodiments, the small molecule functional groups can include an ester functionalized triarylphosine and an azido moiety to form iminophophoranes (aza-ylides) with loss of nitrogen (Prescher, J. A.; Bertozzi, C. R. *Nat. Chem. Biol.* 1, 13 (2005)). In some embodiments, the functional group moieties can be polypeptides moieties. In some embodiments, the polypeptide moieties can be cross-linkable proteins as described herein.

As used herein, the term "recombinant" refers to a polynucleotide synthesized or otherwise manipulated in vitro (for example, "recombinant polynucleotide"), to methods of using recombinant polynucleotides to produce gene products in cells or other biological systems, or to a polypeptide ("recombinant protein") encoded by a recombinant polynucleotide. Thus, a "recombinant" polynucleotide is defined either by its method of production or its structure. In reference to its method of production, the process refers to use of recombinant nucleic acid techniques, for example, involving human intervention in the nucleotide sequence, typically selection or production. Alternatively, it can be a polynucleotide made by generating a sequence comprising a fusion of two or more fragments that are not naturally contiguous to each other. Thus, for example, products made by transforming cells with any non-naturally occurring vector is encompassed, as are polynucleotides comprising sequence derived using any synthetic oligonucleotide process. Similarly, a "recombinant" polypeptide is one expressed from a recombinant polynucleotide.

As used herein, the term "recombinant host cell" refers to a cell that contains a vector, for example, a cloning vector or an expression vector, or a cell that has otherwise been manipulated by recombinant techniques to express a protein of interest.

As used herein, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As will be appreciated, a "fragment" of a protein may be a form of the protein truncated at the amino terminus, the carboxy terminus, and/or internally (such as by natural splicing), and may also be variant and/or derivative. A "domain" of a protein is also a fragment, and comprises the amino acid residues of the protein required to confer biochemical activity corresponding to naturally occurring protein. Truncated molecules that are linear biological polymers such as nucleic acid molecules or polypeptides may have one or more of a deletion from either terminus of the molecule and/or one or more deletions from a non-terminal region of the molecule, where such deletions may be deletions of from about 1-1500 contiguous nucleotide or amino acid residues, preferably about 1-500 contiguous nucleotide or amino acid residues and more preferably about 1-300 contiguous nucleotide or amino acid residues, including deletions of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41-50, 51-74, 75-100, 101-150, 151-200, 201-250 or 251-299 contiguous nucleotide or amino acid residues.

As used herein, the term "gene product" refers to an RNA molecule transcribed from a gene, or a polypeptide encoded by the gene or translated from the RNA.

As used herein, the term "subject" refers to an animal that is the object of treatment, observation or experiment. "Animal" includes cold- and warm-blooded vertebrates and invertebrates, such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, the term "swelling ratio" is the calculated ratio of the swollen gel weight to the dry protein weight.

As used herein, the term "preventing" or "protecting" refers to preventing in whole or in part, or ameliorating, or controlling.

As used herein, the term "treating" refers to its ordinary meaning in the art and can include or exclude therapeutic treatment, prophylactic, or preventative, measures, or administering an agent suspected of having therapeutic potential. The term can include or exclude preventative (e.g., prophylactic) and palliative treatment.

As used herein, the term "protein drug" refers to a polypeptide which exhibits therapeutic potential. In some embodiments, the protein drug can be an antibody, therapeutic protein, insulin, growth hormone, or cytokine.

As used herein the term "antibody" (Ab) includes monoclonal antibodies, polyclonal antibodies, multispecific antibodies (e.g., bispecific antibodies), and antibody fragments, so long as they exhibit the desired biological activity.

As used herein the term "human antibody" refers to an antibody containing only sequences present in an antibody naturally produced by a human, a functional fragment thereof, or a humanized antibody, i.e., a genetically engineered antibody a portion of which (e.g., a frame region or the Fe region) derives from a naturally-occurring human antibody. A "humanized antibody" is generally considered to be a human antibody that has one or more amino acid residues introduced into it from a source that is non-human. As recognized in the art, antibody humanization is performed following the method of Winter and co-workers (Jones et al., Nature, 321:522-525 (1986): Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567, herein incorporated by reference in its entirety) wherein substantially less than an intact human variable domain has been substituted by the corresponding sequence from a non-human species.

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. The monoclonal antibodies included in this disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991).

In some embodiments, the antibody is a humanized antibody. In some embodiments, the humanized antibody is a humanized monoclonal antibody.

Humanized monoclonal antibodies can include or exclude the following: alemtuzumab, apolizumab, aselizumab, atlizumab, bapineuzutnab, bevacizutnab, bivatuzumab mertansine, eantuzumab mertansine, cedelizumab, certolizurnab pegol, cidfusituzumab, cidtuzumab, daclizumab, eculizumab, efalizumab, epratuzumab, erlizumab, etanercept (Enbrel), felxizumab, fontolizumab, gemtuzumab ozogamicin, infliximab (Remicade), inotuzumab, ozogamicin, ipilimumab, labetuzumab, lintuzumab, matuzumab, mepolizumab, motavizumab, motovizumab, natalizumab, nimotuzumab, nolovizumab, numavizumab, oerelizumab, omalizumab, palivizumab, pascolizumab, pecfusituzumab, pectuzumab, pertuzumab, pexelizumab, ralivizumab, ranibizumab, reslivizumab, reslizumab, rituximab (Rituxan), resyvizumab, rovelizumab, ruplizumab, sibroluzumab, siplizurnab, sontuzumab, taeatuzurnab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

In some embodiments, the therapeutic protein can include or exclude the following: C1 esterase inhibitor (Ruconest), Human glucocerebrosidase (Elelyso), Humanized anti-CD20 monoclonal antibody (Gazyva), Fc fusion VEGFR Fc-fusion (Eylea), CTLA-4 Fc-fusion (Nulojix), Glucagon-like peptide-1 receptor agonist Fe-fusion (Trulicity), VEGFR Fc-fusion (Zaltrap), Recombinant factor IX Fe fusion (Alprolix), Recombinant factor VIII Fe-fusion (Eloctate). Albumin fusion GLP-1 receptor agonist-albumin fusion (Tanzeum), Recombinant factor IX albumin fusion (Idelvion), PEGylated IFNβ-1a (Plegridy), Recombinant factor VIII PEGylated (Adynovate), Humanized anti-HER2/neu conjugated to emtansine (Kadcyla), Mouse/human chimeric anti-CD30 (Adcetris), Anti-human epidermal growth factor receptor 2 (HER2) (Perjeta), Anti-HER2/neu conjugated to emtansine (Kadcyla), Anti-IL-6 receptor (Actemra), Anti-CD20 (obinutuzumab; Gazyva), Anti-integrin a4b7 (LPAM-1) (Enty vio), belimumab (Benlysta) ipilimumab (Yervoy), belatacept (Nulojix), brentuximab vedotin (Adcetris), afilbercept (Eylea), asparaginase Erwinia chrysanthemi (Erwinaze), glucarpidase (Voraxaze), taliglucerase alfa (Elelyso), pertuzumab (Perjeta), ziv-afilbercept (Zaltrap), tbo-filgrastim (Granix), ocriplasmin (Jetrea), raxibacumab, ado-trastuzumab emtansine (Kadcyla), golimumab injection for IV use (Simponi Aria), tocilizutnab (Actemra), obinutuzumab (Gazyva), elosulfase alfa (Vimizim), metreleptin (Nlyalept), albiglutide (Tanzeum), raniucirumab (Cyrarnza), siltuximab (Sylvant), vedolizurnab (Entyvio), peginterferon beta-1a pembrolizumab (Keytruda), dulaglutide (Trulicity), blintumomab (Blincyto), nivolumab (Opdivo), secukinumab (Cosentyx), parathyroid hormone (Natpara), filgrastim-sndz (Zarxio), dinutuximab (Unituxin), alirocumab (Praluent), evolocumab (Repatha), idarucizumab (Praxbind), asfotase-alfa (Strensiq), Nlepolizurnab (Nucala), daratumumab (Darzalex), necitumumab (Portrazza), elotuzumab (Empliciti), sebelipase alfa (Kanwna), obiltoxaximab (Anthim), ixekizumab (Taltz), reslizumab (Cingair), infliximab-dyyb (Inflectra), atezolizumab (Tecentriq), daclizumab (Zinbrvta), etanercept-szzs (Ereizi), Rixubis, Novoeight, Tretten, Alprolix, Eloctate, Ruconest, Obizur, Ninny, Nuwiq, Adynovate, Vonvendi, Idelvion, Kovaltry, Afstyla, Abatacept, Abciximab, Adalimumab, Aflibercept, Agalsidase beta, Albiglutide, Aldesleukin, Alefacept, Alemtuzumab, Alglucerase, Alglucosidase alfa, Alirocumab, Aliskiren, Alpha-1-proteinase inhibitor, Alteplase, Anakinra, Ancestim, Anistreplase, Anthrax immune globulin human, Antihemophilic Factor, Anti-inhibitor coagulant complex, Antithrombin Alfa, Antithrombin III human, Antithymocyte globulin, Anti-thymocyte Globulin (Equine), Anti-thymocyte Globulin (Rabbit), Aprotinin, Arcitumomab, Asfotase Alfa, Asparaginase, Asparaginase *Erwinia chrysanthemi*, Atezolizumab, Autologous cultured chondrocytes, Basiliximah, Becaplermin, Belatacept, Belimumab, Beractant, Bevacizumab, Bivalirudin, Blinatumornab, Botulinum Toxin Type A, Botulinum Toxin Type B, Brentuximab vedotin, Brodalumab, Buserelin, C1 Esterase Inhibitor (Human), C1 Esterase Inhibitor (Recombinant) Canakinumab, Capromab, Certolizumab pegol, Cetuximab, Choriogonadotropin alfa, Chorionic Gonadotropin (Human), Chorionic Gonadotropin (Recombinant), Coagulation factor ix, Coagulation factor VIIa, Coagulation factor X human, Coagulation Factor XIII A-Subunit (Recombinant), Collagenase, Conestat alfa, Corticotropin, Cosyntropin, Daclizumab, Daptomycin, Daratumumab, Darbepoetin alfa, Delibrotide, Denileukin diftitox, Denosurnab, Desirudin, Digoxin Immune Fab (Ovine), Dinutuximab, Dornase alfa, Drotrecogin alfa, Dulaglutide, Eculizumab, Efalizumab, Efmoroctocog alfa, Elosulfase alfa, Elotuzumab, Enfuvirtide, Epoetin alfa, Epoetin zeta, Eptifibatide, Etanercept, Evolocutnab, Exenatide, Factor IX Complex (Human), Fibrinogen Concentrate (Human), Fibrinolysin aka plasmin, Filgrastim, Filgrastim-sndz, Follitropin alpha, Follitropin beta, Galsulfase, Gastric intrinsic factor, Gemtuzumab ozogamicin, Glatiramer acetate, Glucagon recombinant, Glucarpidase, Golitnumab, Gramicidin D, Hepatitis A Vaccine, Hepatitis B immune globulin, Human calcitonin, Human *Clostridium tetani* toxoid immune globulin, Human rabies virus immune globulin, Human Rho(D) immune globulin, Human Serum Albumin, Human Varicella-Zoster Immune Globulin, Hyaluronidase, Hyaluronidase (Human Recombinant), Ibritumomab, Ibritumomab tiuxetan, Idarucizumab, Idursulfase, Imiglucerase, Immune Globulin Human, Infliximab, Insulin, Insulin Degludec, Insulin detemir, Insulin Glargine, Insulin glulisine, lnsulin Lispro, Insulin, isophane, Interferon Alfa-2a, Recombinant, interferon alfa-2b, Interferon alfacon-1, Interferon alfa-n1, Interferon alfa-n3, Interferon beta-1a, Interferon beta-1b, Interferon gamma-1b, Intravenous immunoglobulin, ipilimumab, Ixekizumab, Laronidase, Lenograstim, Lepirudin, Leuprolide, Liraglutide, Lucinactant, Lutropin alfa, Mecasermin, Menotropins, Mepolizumab, Methoxy polyethylene glycol-epoetin beta, Metreleptin, Muromonab, Natalizumab, Natural alpha interferon, Multiferon, Necitumumab, Nesiritide, Nivolumab, Obiltoxaximab, Obinutuzumab, Ocriplasmin, Ofatumumab, Omalizumab, Oprelvekin, OspA lipoprotein, Oxytocin, Palifermin, Palivizumab, Pancrelipase, Panitumumab, Pegademase bovine, Pegaptanib, Pegaspargase, Pegfilgrastim, Peginterferon alfa-2a, Peginterferon alfa-2b, Peginterferon beta-1a, Pegloticase, Pegvisomant, Pembrolizumab, Pertuzumab, Poractant alfa, Pramlintide, Preotact, Protamine sulfate, Protein S human, Ramucirumab, Ranibizumab, Rasburicase, Raxibacumab, Reteplase, Rilonacept, Rituximab, Romiplostim, Sacrosidase, Sargramostim, Salumomab Pendetide, Sebelipase alfa, Secukinumab, Sermorelin, Serum albumin, Serum albumin iodonated, Siltuximab, Simoctocog Alfa, Sipuleucel-T, Somatotropin Recombinant, Somatropin recombinant, Streptokinase, Sulodexide, Susoctocog alfa, Taliglucerase alfa, Teduglutide, Teicoplanin, Tenecteplase, Teriparatide, Tesarnorelin, Thrombomodulin Alfa, Thymalfasin, Thyroglobulin, Thyrotropin Alfa, Tocilizumab, Tositumomab, Trastuzumab, Tuberculin, Turoctocog alfa, Urofollitropin, Urokinase, Ustekinumab, Vasopressin, Vedolizumab, and Velaglucerase alfa.

As used herein, the term "fluorescent protein" refers to a protein capable of emitting light upon irradiation of light of a lower wavelength. In some embodiments, the fluorescent protein includes or excludes the following fluorescent proteins: TagBFP, mTagBFP2, Azurite, EBFP2, mKalama1, Sirius, Sapphire, T-Sapphire, ECFP, Cerulean, SCFP3A, mTurquoise, mTurquoise2, telechelic biopolymeric Midoriishi-Cyan, TagCFP, mTFP1, EGFP, Emerald, Superfolder GFP, Telechelic biopolymeric Azami Green, TagGFP2, mUKG, mWasabi, Clover, mNeonGreen, EYFP, Citrine, Venus, SYFP2, TagYFP, Telechelic biopolymeric Kusabira-Orange, mKOK, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, NirFP, TagRFP657, IFP1.4, iRFP, mKeima Red, LSS-mKate1, LSS-mKate2, mBeRFP, PA-GFP, PAmCherry1, PATagRFP, Kaede (green), Kaede (red), KikGR1 (green), KikGR1, (red), PS-CFP2, PS-CFP2, mEos2 (green), mEos2 (red), mEos3.2 (green), mEos3.2 (red), PSmOrange, PSmOrange, and Dronpa.

METHODS

Photo-Patterned Selective Cell Release

In some embodiments, a light-sensitive protein hydrogel is prepared under conditions where no light with wavelengths between 300 nm and 600 nm are present to form a hydrogel film. The film can be pressure applied, compressed, spin-cast, or dip-coated. Patterned light, x-rays, electrons or other electromagnetic radiation can be passed through a mask by photolithography; alternatively, the radiation can be applied in the form of a focused beam, as in stereolithography, to control where on the light-sensitive protein hydrogel film the cells are released. Photolithography can be used with the light-sensitive protein hydrogels of this disclosure via the release of a photoliable group or via a secondary light-sensitive compound to promote cross-linking or breaking of the polymer chains so that the surface areas of the photomask that are exposed to light are rendered either soluble or insoluble to a developing solution that is then applied to the light-sensitive protein hydrogel to leave only the desired pattern intact.

Examples of photo-cross-linking processes that can be utilized include (a) ultra-violet photo-cross-linking of proteins to RNA [as described in A. Paleologue, et al., "Photo-Induced Protein Cross-Linking to 5S RNA and 28-5.8S RNA within Rat-Liver 60S Ribosomal Subunits," Eur. J. Biochem. 149, 525-529 (1985)]; (b) protein photo-cross-linking in mammalian cells by site-specific incorporation of a photoreactive amino acid [as described in N. Hino, et al., "Protein Photo-Cross-Linking in Mammalian Cells by Site-Specific Incorporation of a Photoreactive Amino Acid," Nature Methods 2, 201-206 (2005)]; (c) use of ruthenium bipyridyls or palladium porphyrins as photo-activatable crosslinking agents for proteins [as described in U.S. Pat. No. 6,613,582 (Kodadek et al.)]; and (d) photocrosslinking of heparin to bound proteins via the cross-linking reagent, 2-(4-azidophenylamino)-4-(1-ammonio-4-azabicyclo[2,2,2] oct-1-yl)-6-morpho-lino-1,3,5-triazine chloride [as described in Y. Suda, et al., "Novel Photo Affinity Cross-Linking Resin for the Isolation of Heparin Binding Proteins," Journal of Bioactive and Compatible Polymers 15, 468-477 (2000)].

In another aspect, the invention includes methods of treating a subject (e.g. patient) by administering light-sensitive protein hydrogels of this disclosure to the subject. Generally, these methods include methods for tissue engineering and methods for treating skin disorders.

Skin Regeneration

Scaffold-guided tissue regeneration involves seeding highly porous biodegradable scaffolds with donor cells and/or growth factors, then culturing and implanting the scaffolds to induce and direct the growth of new tissue. The goal is for the cells to attach to the scaffold, then replicate, differentiate (i.e., transform from a non-specific state into a cell exhibiting the functions of the target tissue), and organize into normal healthy tissue as the scaffold degrades.

Methods of Treatment with Light-Sensitive Protein Hydrogels

The light-sensitive protein hydrogels of this disclosure can be used to treat skin disorders, including burns, skin cancer, actinic keratosis, rosacea, carbuncle, eczema, psoriasis, cellulitis, measles, basal cell carcinoma, squamous cell carcinoma, melanoma, lupus, contact dermatitis, vitiligo, seborrheic dermatitis, keratosis pilaris, melisma, and impetigo. In some embodiments, the protein hydrogel comprising captured cells and/or one or more types of therapeutic protein is formed in the absence of light of a wavelength between 300 and 600 nm, then topically applied under a reduced light environment to the skin of a subject in need thereof. The reduced light environment can be affected by the use of a filter, mask, sealant, or other means. In some embodiments, the reduced light environment can be converted to a full White light or 522 nm laser light environment by irradiating the applied protein hydrogel composition with the appropriate light source. As the hydrogel changes phase to a liquid state, the captured cells and/or therapeutic proteins are released at the local point of application. In some embodiments, the captured cells include stem cells. In some embodiments, the captured stem cells include embryonic stems cells, induced pluripotent stem cells, or mixtures thereof.

AdoB12 is responsive to a broad range of visible light (<600 nm), thus making $CarH_C$ hydrogels if this disclosure responsive to visible light of the same wavelength range. The inventors have recognized that chemical modification on AdoB12 (or AdoCbl) extends its responsive wavelength range. In some embodiments, AdoCbl-4 (AdoCbl modified with Dylight800) can be photolyzed by light of certain wavelengths including 546 nm, 730 nm, and 780 nm, resulting in photolyzed products like adenosine and B12-Dylight800. The inventors have recognized that Co—C bond cleavage (photolysis) causes $CarH_C$-AdoB12 complex's light responsiveness. The inventors have recognized that photoresponsive protein hydrogels, including the $CarH_C$ hydrogel complexed with modified AdoB12 of this disclosure, can exhibit solid-to-liquid phase transition with extended light conditions. The photosensitive protein hydrogel can exhibit extended light responsiveness in the range of 500-1000 nm when the multidentate ligand (which can include or exclude AdoB12) is modified with a photosensitizer. In some embodiments, the photosensitizer can include or exclude: TAMRA, SulfoCy5, Atto725, Dylight800, Malachite green, QSY 7 (Quasar 7), QSY 9, QSY 21, Rhodamine Red-X, Lissamine rhodamine B. rhodamine 6G, Texas red (and Texas red dyes in general, including Texas Red-X, Texas red C2-dichlorotriazine), naphthofluorescein, carboxyrhodamine 6G, and ROX. In some embodiments, the photosensitizer is conjugated to the multi-dentate ligand. In some embodiments, the photosensitizer conjugated to the multi-dentate ligand is selected from: Cbl1, Cbl2, Cbl3, Cbl4, Cbl5, Cbl6, and Cbl-Bod.

The inventors have recognized that the photosensitizer can enable two-photon excitation to irradiate the light-sensitive protein hydrogels with a wavelength of light higher than 600 nm from a ultrafast pulsed laser light source. The inventors have recognized that tissue has an optical window from about 600 nm to about 900 nm, but the light-sensitive protein hydrogels are less sensitive to light comprising a wavelength higher than 600 nm. The inventors have recognized that two-photon excitation can be used to irradiate the light-sensitive protein hydrogels through the tissue optical window from about 600 nm to about 900 nm, when the light-sensitive protein hydrogels further comprises a photosensitizer and the photosensitizer converts the incident light comprising a wavelength from about 600 nm to about 900 nm into a wavelength of light between about 300 nm to about 600 nm. The inventors have recognized that the Co—C bond on AdoB12 can absorb two photons (900 nm) simultaneously when exposed to a two photon pulsed laser, which is effectively equivalent to one photon of 450 nm. The two photon photosensitizer method extends the responsive range of the photosensitive protein hydrogels. The inventors have recognized that this described mechanism can be used to irradiate light-sensitive protein hydrogels which are subdermal or deeper in the tissue of a subject, to enable the release of therapeutic proteins or cells within the tissue of a subject.

Another embodiment of this invention includes a composition of this invention for use in the treatment of the diseases or conditions described herein in a subject, e.g., a human, suffering from such disease or condition. Also provided is the use of a compound of this invention in the preparation of a medicament for the treatment of the diseases and conditions described herein in a warm-blooded animal, such as a mammal, e.g. a human, suffering from such disorder.

In some embodiments, a dose is administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. In some embodiments, for orally administered doses, the pill, capsule, or tablet is ingested daily or less frequently for a specified period of time. In some embodiments, to regimen is repeated for a number of cycles of therapy.

Pharmaceutical Formulation/Compositions and Uses

In order to use a light-sensitive protein hydrogel compositions of this disclosure for the therapeutic treatment (including prophylactic treatment) of mammals including humans, in some embodiments the compound is formulated in accordance with standard pharmaceutical practice as a pharmaceutical composition. According to this embodiment of the invention, there is provided a pharmaceutical composition comprising a light-sensitive protein hydrogel compositions of this disclosure in association with a pharmaceutically acceptable diluent or carrier.

In some embodiments, the pharmaceutical light-sensitive protein hydrogel compositions of this disclosure (or formulation) for application is packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In some embodiments, pharmaceutical formulations of the light-sensitive protein hydrogel compositions of this disclosure are prepared for various routes and types of administration. In some embodiments, a light-sensitive protein hydrogel composition of this disclosure having the desired degree of purity is mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. In some embodiments, formulation is conducted by mixing at ambient temperature at the appropriate pH, and at the desired degree of purity, with physiologically acceptable carriers. i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

In some embodiments, the pharmaceutical compositions of the invention comprising light-sensitive protein hydrogel compositions of this disclosure are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In addition to the light-sensitive protein hydrogel compositions of this disclosure, the invention includes pharmaceutical compositions, including tablets, capsules, solutions, and suspensions for parenteral and oral delivery forms and formulations, comprising a pharmaceutically acceptable carrier and therapeutically effective amounts of the compositions described herein.

In human and animal therapy for the treatment of skin disorders, for example, the compositions of this disclosure can be administered alone, but will generally be administered in admixture with a pharmaceutical carrier selected with regard to the intended route of administration and standard pharmaceutical practice. Preferably, they are administered by parenteral administration, and are best used in the form of a sterile aqueous solution which may contain other substances, for example enough salts or monosaccharides to make the solution isotonic with blood.

In some embodiments, for treatment of the eye or other external tissues, e.g., mouth and skin, the formulations are applied as described herein comprising the active ingredient(s) in an amount of, e.g., 0.001 to 0.5% w/w.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

When applied topically, the light-sensitive protein hydrogel comprising cells and/or therapeutic proteins in the compositions of this disclosure is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition.

Examples of suitable vehicles include ointments, creams, gels, or suspensions, with, or without, purified collagen. In some embodiments, the compositions are impregnated into articles which can include or exclude transdermal patches, plasters, and bandages, preferably in liquid or semi-liquid form.

Acceptable diluents, carriers, excipients and stabilizers are nontoxic to recipients at the dosages and concentrations employed, and include saline and/or buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN™, PLURONICS™ or polyethylene glycol (PEG).

Articles of Manufacture/Kits

In another embodiment of the invention, an article of manufacture, or "kit," containing materials useful for the treatment of the diseases and disorders described above is provided. The kit contains a composition comprising light-sensitive protein hydrogels of this disclosure. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic. The label or package insert also indicates that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution (including Ringer's lactate solution), Tyrode's solution, Hellmann's solution, and dextrose solution. In some embodiments, the article of manufacture includes or excludes other buffers, diluents, filters, needles, and syringes.

The term "buffer," as used herein, denotes a pharmaceutically acceptable excipient, which stabilizes the pH of a pharmaceutical preparation. Pharmaceutically acceptable buffers include, but are not limited to, histidine-buffers, citrate-buffers, succinate-buffers, acetate-buffers, phosphate-buffers, arginine-buffers, or mixtures thereof. The abovementioned buffers are generally used in an amount of about 1 mM to about 100 mM, of about 5 mM to about 50 mM and of about 10-20 mM, in some embodiments, the pH of the buffered solution is at least 4.0, at least 4.5, at least 5.0, at least 5.5 or at least 6.0. In some embodiments, the pH of the buffered solution is less than 7.5, less than 7.0, or less than 6.5. In some embodiments, the pH of the buffered solution is about 4.0 to about 7.5, about 5.5 to about 7.5, about 5.0 to about 6.5, and about 5.5 to about 6.5 with an acid or a base described herein, e.g. hydrochloric acid, acetic acid, phosphoric acid, sulfuric acid and citric acid, sodium hydroxide and potassium hydroxide. As used herein when describing pH, "about" means plus or minus 0.2 pH units.

As used herein, the term "surfactant" can include a pharmaceutically acceptable excipient which is used to protect therapeutic protein and/or cell formulations against mechanical stresses, like agitation and shearing. Examples of pharmaceutically acceptable surfactants include polyoxyethyiensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulphate (SDS). Suitable surfactants include polyoxyethylenesorbitan-fatty acid esters such as polysorbate 20, (sold under the trademark Tween 20®) and polysorbate 80 (sold under the trademark Tween 80®). Suitable polyethylene-polypropylene copolymers are those sold under the names Pluronic® F68 or Poloxamer 188®. Suitable Polyoxyethylene alkyl ethers are those sold under the trademark Brij®. Suitable alkylphenolpolyoxyethylene esters are sold under the tradename Triton-X. When polysorbate 20 (Tween 20®) and polysorbate 80 (Tween 80®) are used, they are generally used in a concentration range of about 0.001 to about 1%, of about 0.005 to about 0.2% and of about 0.01% to about 0.1% w/v (weight/volume).

In some embodiments, this disclosure relates to:

A1. A light-responsive hydrogel biopolymer matrix comprising:
   (a) one or a plurality of light-responsive gelation initiator complexes connected to one or a plurality of a first extracellular matrix protein fragments, and
   (b) two or more cross-linkable proteins connected to one or a plurality of a second extracellular matrix protein fragments.

A2. The light-responsive hydrogel biopolymer matrix of A1, wherein the light-responsive gelation initiator complex comprises a protein photoreceptor.

A1.1 A light-responsive hydrogel biopolymer matrix comprising:
   one or a plurality of light-responsive gelation initiator complexes comprising a protein photoreceptor CarHc and a multi-dentate ligand adenosylcobalamin, connected to one or a plurality of a first extracellular matrix protein fragments, and
   two or more cross-linkable proteins connected to one or a plurality of a second extracellular matrix protein fragments,
   wherein the first extracellular matrix protein fragments and second extracellular matrix protein fragments are independently selected from elastin fragments which comprise a repeating polypeptide having the sequence of (VPGXG)$_n$ (SEQ ID NO: 23), wherein X represents valine or glutamate, the ratio of valine to glutamate ranges from 10:1 to 1:10, n is an integer selected from 2 to 25, the two or more cross-linkable proteins are SpyTag and SpyCatcher, and
   the matrix is responsive to light comprising a wavelength from about 300 nm to about 600 nm.

A1.2 The light-responsive hydrogel biopolymer matrix of A1.1,
   wherein a first telechelic biopolymer comprises a first light-responsive gelation initiator complex covalently hound to the first extracellular matrix protein fragments which are covalently bound to a first two or more cross-linkable proteins, and a second telechelic biopolymer comprises a second light-responsive gelation initiator complex covalently bound to the second extracellular matrix protein fragments which are covalently bound to a second two or more cross-linkable proteins.

A1.3 The light-responsive hydrogel biopolymer matrix of A1.2,
   wherein said first telechelic biopolymer is a recombinant protein encoding for the first light-responsive gelation initiator complex covalently bound to the first extracellular matrix protein fragments which are covalently bound to a first two or more cross-linkable proteins, and said second telechelic biopolymer is a recombinant protein encoding for the second light-responsive gelation initiator complex covalently bound to the second extracellular matrix protein fragments which are covalently bound to a second two or more cross-linkable proteins.

A3. The light-responsive hydrogel biopolymer matrix of A2, wherein the protein photoreceptor is selected from: CarHc, LOV, PYP, phytochrome, and cytochrome.

A4. The light-responsive hydrogel biopolymer matrix of A3, wherein the protein photoreceptor is CarHc.

A5. The light-responsive hydrogel biopolymer matrix of A1, wherein the light-responsive gelation initiator complex further comprises a multi-dentate ligand.

A6. The light-responsive hydrogel biopolymer matrix of 45, wherein the multi-dentate ligand is selected from: adenosylcobalamin, cyanocobalamin, methylcobalamin, hydroxocobalamin, flavin, biliverdin, and streptavidin.

A7. The light-responsive hydrogel biopolymer matrix of A6, wherein the multi-dentate ligand is adenosylcobalamin.

A8. The light-responsive hydrogel biopolymer matrix of A1, wherein the first extracellular matrix protein fragments and second extracellular matrix protein fragments are independently selected from fragments of: collagen, fibronectin, gelatin, elastin, GB1 (immunoglobulin G-binding protein G), procollagen, and combinations thereof.

A9. The light-responsive hydrogel biopolymer matrix of A9, wherein the first extracellular matrix protein fragments and second extracellular matrix protein fragments are independently selected from fragments of elastin.

A10. The light-responsive hydrogel biopolymer matrix of A9, wherein the elastin fragments comprise a repeating polypeptide having the sequence of (VPGXG)$_n$ (SEQ ID NO: 19), wherein X represents valine or glutamate, the ratio of valine to glutamate ranges from 100:1 to 1:100, and n is an integer between 1 to 100.

A11. The light-responsive hydrogel biopolymer matrix of A10, wherein the ratio of valine to glutamate ranges from 10:1 to 1:10.

A12. The light-responsive hydrogel biopolymer matrix of A11, wherein the ratio of valine to glutamate is 4:1

A13. The light-responsive hydrogel biopolymer matrix of A10, wherein n is an integer between 1 to 10.

A14. The light-responsive hydrogel biopolymer matrix of A10, wherein n is 15.

A15. The light-responsive hydrogel biopolymer matrix of A1, wherein the two or more cross-linkable proteins are selected from: CarHc and CarHc in the presence of AdoB$_{12}$ or other photosensitive protein, SpyTag and SpyCatcher, CL7 and Im7, and Strep-tag and Streptavidin.

A16. The light-responsive hydrogel biopolymer matrix of A15, wherein the two or more cross-linkable proteins are SpyTag and SpyCatcher.

A17. The light-responsive hydrogel biopolymer matrix of A1, wherein the matrix is responsive to light with a wavelength from about 300 nm to about 600 nm.

A18. The light-responsive hydrogel biopolymer matrix of A17, wherein the matrix is responsive to light with a wavelength of about 520 nm.

A19. The light-responsive hydrogel biopolymer matrix of A17, wherein the matrix exhibits a phase transition from gel to solution upon exposure to light.

A20. The light-responsive hydrogel biopolymer matrix of A1,
wherein the light-responsive gelation initiator complex comprises the protein photoreceptor CarHc,
the light-responsive gelation initiator complex further comprises the multi-dentate ligand adenosylcobalamin,
the first extracellular matrix protein fragments and second extracellular matrix protein fragments are independently selected from elastin fragments which comprise a repeating polypeptide having the sequence of (VPGXG)$_n$ (SEQ ID NO:20), wherein X represents valine or glutamate, the ratio of valine to glutamate is 4:1, and n is 15,
the two or more cross-linkable proteins are SpyTag and SpyCatcher, and
the matrix is responsive to light with a wavelength from about 300 nm to about 600 nm.

A21. The light-responsive hydrogel biopolymer matrix of A20,
wherein a first telechelic biopolymer comprises a first light-responsive gelation initiator complex covalently bound to the first extracellular matrix protein fragments which are covalently bound to a first two or more cross-linkable proteins, and a second telechelic biopolymer comprises a second light-responsive gelation initiator complex covalently hound to the second extracellular matrix protein fragments which are covalently bound to a second two or more cross-linkable proteins.

A22. The light-responsive hydrogel biopolymer matrix of A21,
wherein said first telechelic biopolymer is a recombinant protein encoding for the first light-responsive gelation initiator complex covalently bound to the first extracellular matrix protein fragments which are covalently bound to a first two or more cross-linkable proteins, and said second telechelic biopolymer is a recombinant protein encoding for the second light-responsive gelation initiator complex covalently bound to the second extracellular matrix protein fragments which are covalently bound to a second two or more cross-linkable proteins.

A23. The light-responsive hydrogel biopolymer matrix of A22,
wherein the first telechelic biopolymer and second telechelic biopolymer independently have the linkage structure selected from: CarHc-elastin-CarHc or CarHc-elastin-CarHc-elastin-CarHc.

A24. The light-responsive hydrogel biopolymer matrix of A22,
wherein the first telechelic biopolymer and second telechelic biopolymer independently have the linkage structure selected from: SpyTag-CarHc-SpyTag, SpyCatcher-CarHc-SpyCatcher, SpyTag-CarHc-SpyCatcher, SpyTag-CarHc, SpyCatcher-CarHc, and CarHc-CL7.

A25. The light-responsive hydrogel biopolymer matrix of A22,
wherein the first telechelic biopolymer and second telechelic biopolymer independently have the linkage structure selected from: SpyTag-elastin-CarHc-elastin-SpyTag, SpyCatcher-elastin-CarHc-elastin-SpyCatcher, SpyTag-elastin-CarHc-elastin-SpyCatcher, SpyTag-elastin-CarHc, SpyCatcher-elastin-CarHc, and CarHc-elastin-CL7.

A26. The light-responsive hydrogel biopolymer matrix of A1,
wherein upon exposure to light with a wavelength from about 300 nm to about 600 nm, the matrix exhibits a phase transition from gel to solution upon exposure to light.

A27. The light-responsive hydrogel biopolymer matrix of A1 further comprising a cell.

A28. The light-responsive biopolymer matrix of A27, wherein the cell is a mammalian cell.

A29. The light-responsive hydrogel biopolymer matrix of A28, wherein the mammalian cell is a fibroblast or a stem cell.

A30. The light-responsive hydrogel biopolymer matrix of A29, wherein the mammalian cell is a mesenchymal stem cell (hMSCs).

A31. The light-responsive hydrogel biopolymer matrix of A1 further comprising an non-covalently bound protein.

A32. The light-responsive hydrogel biopolymer matrix of A31, wherein the non-covalently bound protein is selected from therapeutic protein, cytokine, or a fluorescent protein.

A33. The light-responsive hydrogel biopolymer matrix of A32, wherein the fluorescent protein is mCherry.

A34. The light-responsive hydrogel biopolymer matrix of A32, wherein the therapeutic protein is an antibody.

A35. The light-responsive hydrogel biopolymer matrix of A1, further comprising water.

A36. The light-responsive hydrogel biopolymer matrix of A35, rein the water content of the hydrogel is in the range from 70% to 99.5% (w/w).

A37. The light-responsive hydrogel biopolymer matrix of A2, wherein the protein photoreceptor content of the hydrogel is in the range from 0.001% to 0.5% (w/w).

A38. An oligonucleotide sequence encoding the linkage structure of A25.

A39. The oligonucleotide sequence of A38, comprising a sequence selected from SEQ ID NO:1 or SEQ ID NO: 2.

A40. The oligonucleotide sequence of A38, comprising a sequence having higher than 80% homology to that of SEQ ID NO:1 or SEQ ID NO: 2.

A41. The oligonucleotide sequence of A40, comprising a sequence having higher than 90% homology to that of SEQ ID NO:1 or SEQ ID NO: 2.

A42. The oligonucleotide sequence of A41, comprising a sequence having higher than 95% homology to that of SEQ ID NO:1 or SEQ ID NO: 2.

A43. The oligonucleotide sequence of A42, comprising a sequence having higher than 97.5% homology to that of SEQ ID NO:1 or SEQ ID NO: 2.

A43.5 A vector comprising the oligonucleotide sequences of A38 to A43.

A43.6 A plasmid comprising the vector of A43.5.

A44. A method for producing a light-responsive hydrogel biopolymer matrix, the method comprising dissolving one or a plurality of light-responsive gelation initiator complexes connected to one or a plurality of a first extracellular matrix protein fragments and two or more cross-linkable proteins connected to one or a plurality of a second extracellular matrix protein fragments in an aqueous solution to form a gelation mixture under light which does not comprise a wavelength of less than about 600 nm,
  wherein the light-responsive gelation initiator complex comprises the protein photoreceptor CarHc;
  wherein the light-responsive gelation initiator complex further comprises the multi-dentate ligand adenosylcobalamin;
  wherein the first extracellular matrix protein fragments and second extracellular matrix protein fragments are independently selected from elastin fragments which comprise a repeating polypeptide having the sequence of (VPGXG)$_n$ (SEQ ID NO: 20), wherein X represents valine or glutamate, the ratio of valine to glutamate is 4:1, and n is 15, and
  the two or more cross-linkable proteins are SpyTag and SpyCatcher.

A45. A method of capturing cells in a photoresponsive hydrogel matrix, the method comprising the steps of:
  dissolving one or more cells in an aqueous solution,
  dissolving one or a plurality of light-responsive gelation initiator complexes connected to one or a plurality of a first extracellular matrix protein fragments and two or more cross-linkable proteins connected to one or a plurality of a second extracellular matrix protein fragments in the aqueous solution comprising one or more cells to form a gelation mixture under light which does not comprise a wavelength of less than about 600 nm,
  wherein the light-responsive gelation initiator complex comprises the protein photoreceptor CarHc;
  wherein the light-responsive gelation initiator complex further comprises the multi-dentate ligand adenosylcobalamin;
  wherein the first extracellular matrix protein fragments and second extracellular matrix protein fragments are independently selected from elastin fragments which comprise a repeating poly peptide having the sequence of (VPGXG)$_n$ (SEQ ID NO: 20), wherein X represents valine or glutamate, the ratio of valine to glutamate is 4:1, and n is 15, and
  the two or more cross-linkable proteins are SpyTag and SpyCatcher.

A46. The method of A45, further comprising the steps of:
  (c) contacting the gelation mixture with cell growth media to form a gelation growth media, and
  (d) incubate the gelation growth media to form incubated gelation growth media.

A47. The method of A46, further comprising the step of:
  (e) irradiate the incubated gelation growth media with light comprising a wavelength between about 300 nm and about 600 nm to transform the hydrogel into a liquid.

S48. The light-responsive hydrogel biopolymer matrix of A1 can further comprise one or more chromophore (such as cobalamin derivative) and/or one or more a chromophore-hosting protein that comprises a part of CarH with a chromophore.

EXAMPLES

The invention is now described with reference to the following Examples. These Examples are provided for the purpose of illustration only, and the invention is not limited to these Examples, but rather encompasses all variations that are evident as a result of the teaching provided herein.

The Examples described herein demonstrate that light-sensitive protein hydrogels can be created and used for light-selective release of cells and/or proteins. Aspects and embodiments of the instant disclosure stem from the unexpected discovery that certain light-sensitive protein hydrogel formulations have surprising, and unexpected, utility and efficacy when used to selectively release cells and/or proteins under selected light conditions.

The therapeutically effective light-sensitive protein hydrogels of this disclosure are prepared according to the synthetic scheme outlined above. However, the invention is not limited to those methods. The compositions may also be prepared as described herein for structurally related proteins and/or cells.

Figure 22:
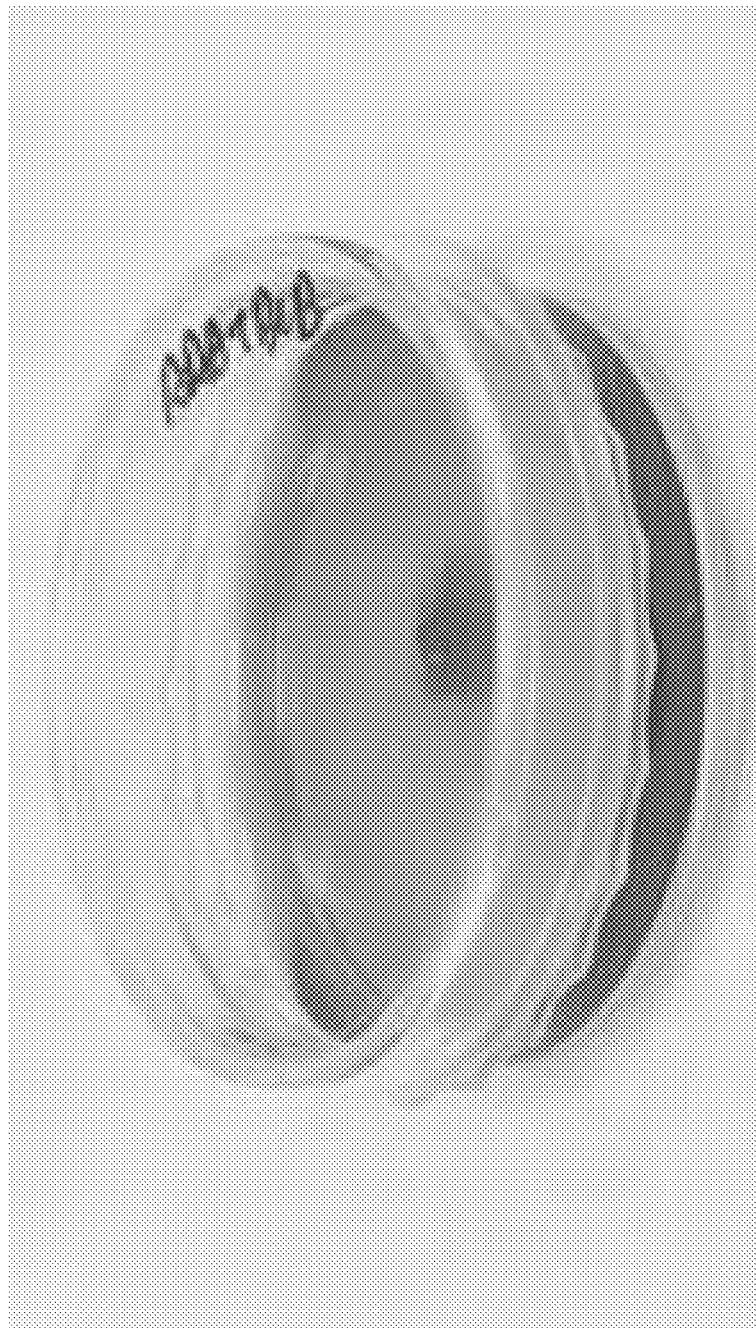
FIG. 22 shows a photograph of cell-laden light-sensitive protein hydrogel (ACA+BCB+AdoB12) in a cell culture dish soaked in media.

In some embodiments, this disclosure relates to a method for mammalian cell culturing. The cells can be mixed with the protein hydrogel in aqueous solutions which comprise cell growth media, before addition of the multi-dentate ligand. The cells form part of the hydrogel after introduction of the multi-dentate ligand (AdoB12) in the dark (FIG. 22) before soaked in media. Alternatively, cells can be plated on the protein hydrogel surface before soaked in media.

In some embodiments, the aqueous solution can be selected from PBS, water, DMEM, Hanks' BSS, Earle's salts, DPBS, HBSS, EBSS, MEM, GMEM, PRMI 1640, Isoves DMEM Leibovitz L-15, CHO, HEK293, Ham F10, Ham F12, and combinations thereof.

In some embodiments, the aqueous solution can comprise one or more of: glucose, growth factors, and Bicarbonate/HEPES buffer, a pH indicator, oxygen, carbon dioxide, vitamins, amino acids and other nutrients.

In some embodiments, the time b mixing and soaking can range from hour.

In another aspect, the invention provides a method for releasing cells cultured in or on the protein-based light-responsive hydrogel. When exposed in effective light conditions, the hydrogels are characterized by undergoing solid-to-liquid transition, and releasing the cells imbedded or attached to it.

In all embodiments, the time required for cell release can vary from several seconds to tens of minutes depending on gel geometry, formulation, and light spectral characteristics and intensity, in some embodiments, gentle shaking further accelerates cell release.

Experimental Procedures

Gene Construction and Protein Expression

Plasmids, such as pQE801::SpyTag-ELP-RGD-ELP-SpyTag (AA), pQE801::Spy Tag-ELP-SpTag-ELP-SpyTag (AAA), CarH$_C$-ELP-RGD-ELP-CarH$_C$, and pQE801::SpyCatcher-ELP-SpyCatcher (BB), were constructed as described previously (Katz, Macromol. Biosci. 10: 339-348 (2010)). The carH$_C$ gene was purchased as a gBlocks gene fragment from Integrated DNA Technologies, pQE801::SpyTag-ELP-carHC-ELP-SpyTag (ACA) and pQE801:SpyCatcher-ELP-carH$_C$-ELP-SpyCatcher(BCB) were constructed by replacing the middle RGD site with carH$_C$ in pQE801::AA and pQE801::BB, respectively. pQE801 (SEQ ID NO: 13) was obtained from Qiagene. SacI and SpeI restriction sites were used. pET221)::mcherry-carH$_C$ was constructed by inserting the mCherry gene into a pET22b-derived plasmid carrying a carH$_C$ gene, and NdeI and SacI restriction sites were used. E. coli strain DH5α was used for plasmid amplification.

E. coli strain BL21 (DE3) was the bacterial host for protein expression. The bacterial cells were grown at 37° C. in LB to the midlog phase (OD at 600 nm, 0.6-0.8) followed by adding 1 mM isopropyl β-D-1-thiogalactopyranoside (Sangon Biotech) to induce protein expression at 37° C. After 4 h, cells were harvested and flash-frozen in liquid $N_2$ before protein purification. The proteins were purified on HisTrap columns (GE Healthcare, Inc.) following the column manufacturer's recommendations. The purified proteins were dialyzed against Milli-Q water (5 L×4) at 4° C. and lyophilized at −100° C. Lyophilized proteins were stored at −80° C. before use.

Table 1 (FIG. 29) summarizes the plasmid constructs, primers, and sources of manufacture of the polynucleotides used in this study.

Hydrogel Preparation

The ACA and BCB proteins were dissolved in PBS to yield 10 wt % solutions. $AdoB_{12}$ (Shaanxi Pioneer Biotech) was dissolved in PBS to a final concentration of 9.2 mM. ACA and BCB were mixed at an equimolar ratio followed by addition of a stoichiometric amount of $AdoB_{12}$ in the dark at room temperature.

Dynamic Shear Rheology

Dynamic time-, strain-, and frequency-sweep experiments were performed on a TA Instruments ARES-RFS strain-controlled rheometer with a standard steel parallel-plate geometry (8-mm diameter). Gelation of the mixture of 31 μL BCB (10 wt % in PBS). 19 μL ACA (10 wt % in PBS), and 10 μL $AdoB_{12}$ (9.2 mM in PBS) was monitored by time-sweep measurement, with strain and frequency fixed at 5% and 1 rad/s, respectively, at 25° C. for 7 h. Strain sweep was performed from 0.1 to 10% at a fixed frequency of 1 rads at 25° C. Frequency sweep was performed from 100 to 0.01 rad/s by holding the strain at 5% at the temperature indicated (16, 25, or 37° C.). All of the samples were wrapped with aluminum foil to avoid light during the rheological measurements. Photolysis was conducted by exposing the $CarH_C$-comprising hydrogel to white LED light (30 or 90 klux) comprising a wavelength of light between about 300 nm and about 600 nm, and dynamic time sweep was used to monitor the gel-sol transition.

Protein Immobilization and Light-Induced Release

The AAA and BCB proteins and the $AdoB_{12}$ cofactor were dissolved in the PBS solution containing mCherry-$CarH_C$ or mCherry (50 μM) to yield 10 wt % protein solutions for AAA and BCB and a 9.2 mM solution for $AdoB_{12}$, respectively. Hydrogels were prepared by mixing the three solutions 36 μL BCB, 7.5 μL AAA, and 7 μL $AdoB_{12}$ and cured in the dark for 24 h. To examine the effect of light on the protein release, the gels were either exposed to white LED light (90 klux) comprising a wavelength between about 300 nm and about 600 nm for 10 min or constantly kept in the dark as a control. Both groups of samples were immersed with 500 μL PBS and transferred to the dark. To determine the amounts of protein released into the supernatant, aliquots (100 μL) were taken for fluorescence measurements (excitation at 587 nm and emission at 610 nm) with a Varioskan LUX multimode microplate reader (Thermo Scientific) at different time points, and 100 μL fresh PBS was added back to keep the supernatant volume constant.

Encapsulation and Light-Induced Release of 3T3 Fibroblasts and hMSCs

NIH/3T3 mouse embryonic fibroblasts were cultured in high-glucose DMEM (Sangon Biotech) supplemented with 10% (vol/vol) FBS (Sangon Biotech), 1% (vol/vol) penicillin-streptomycin (Saigon Biotech), and 1% (vol/vol) nonessential amino acids (Sangon Biotech) in a 5% $CO_2$ atmosphere at 37° C. and passaged every 3 days. At 70-80% confluence, cells were detached with 1 mL trypsin solution (Sangon Biotech) followed by addition of 2 mL DMEM to neutralize the trypsin. Around 60,000 cells were pelleted and resuspended with 31 μL BCB in DMEM (10 wt %) and then placed on a cell culture dish with a coverslip bottom. Gelation was initiated by adding 19 μL ACA in PBS (10 wt %) and 10 μL $AdoB_{12}$ in PBS (9.2 mM). The gel was cured in the dark for 2 hrs. before being covered with the culture medium. After 24 hrs. of incubation and washing with Dulbecco's PBS (Sangon Biotech), live/dead cell viability assays (Thermo Fisher Scientific) were conducted. Fluorescence images were obtained on a Laser Scanning Confocal Microscope [LSM7 DUO (710+LIVE); Zeiss].

hMSCs were provided as a gift from Chao Wan, Chinese University of Hong Kong, Hong Kong. The cells were cultured at 37° C. with 5% $CO_2$ in MEM Alpha (Gibco) supplemented with 10% (vol/vol) FBS (Gibco), 2 mM L-glutamine, and 1% (vol/vol) penicillin-streptomycin. Cells were passaged every 5-6 days using 0.25% trypsin (Sangon Biotech) solution. The encapsulation procedure was similar to that of 3T3 fibroblasts as described above.

For cell release/recovery experiments, cell-laden gels were rinsed and immersed by PBS before exposure to white light (halogen lamp in the microscope, ~22 klux). Cell release was monitored and recorded with an optical microscope equipped with a camera (Olympus CKX41). The live/dead staining assay was performed to examine the viability of recovered cells. Quantification of cell viability was done by counting live and dead cells in the micrographs (n≥4) that were randomly chosen.

Example 1: Protein Construct Design

To polymerize polypeptides comprising $CarH_C$, two gene constructs were designed encoding the telechelic proteins SpyTag-elastin-$CarH_C$-elastin-SpyTag (ACA; 41 kDa) and SpyCatcher-elastin-$CarH_C$-SpyCatcher (BCB; 68 kDa), respectively (FIG. 1B). The ELP (elastin-like polypeptide, or extracellular matrix protein fragment) domain comprises repeating pentapeptides $(VPGXG)_{15}$ (SEQ ID NO: 20), where X represents either valine or glutamate at a ratio of 4:1, a composition that enhances the expression yield and solubility of these recombinant proteins under physiological conditions. The reaction of SpyTag and SpyCatcher was designed to covalently stitch together $CarH_C$ to form protein biopolymers, of which interchain interactions will be dominated by the $AdoB_{12}$-induced CarHc tetramerization (FIG. 1B).

Example 2: Synthesis of $CarH_C$ Hydrogels

Figure 9:
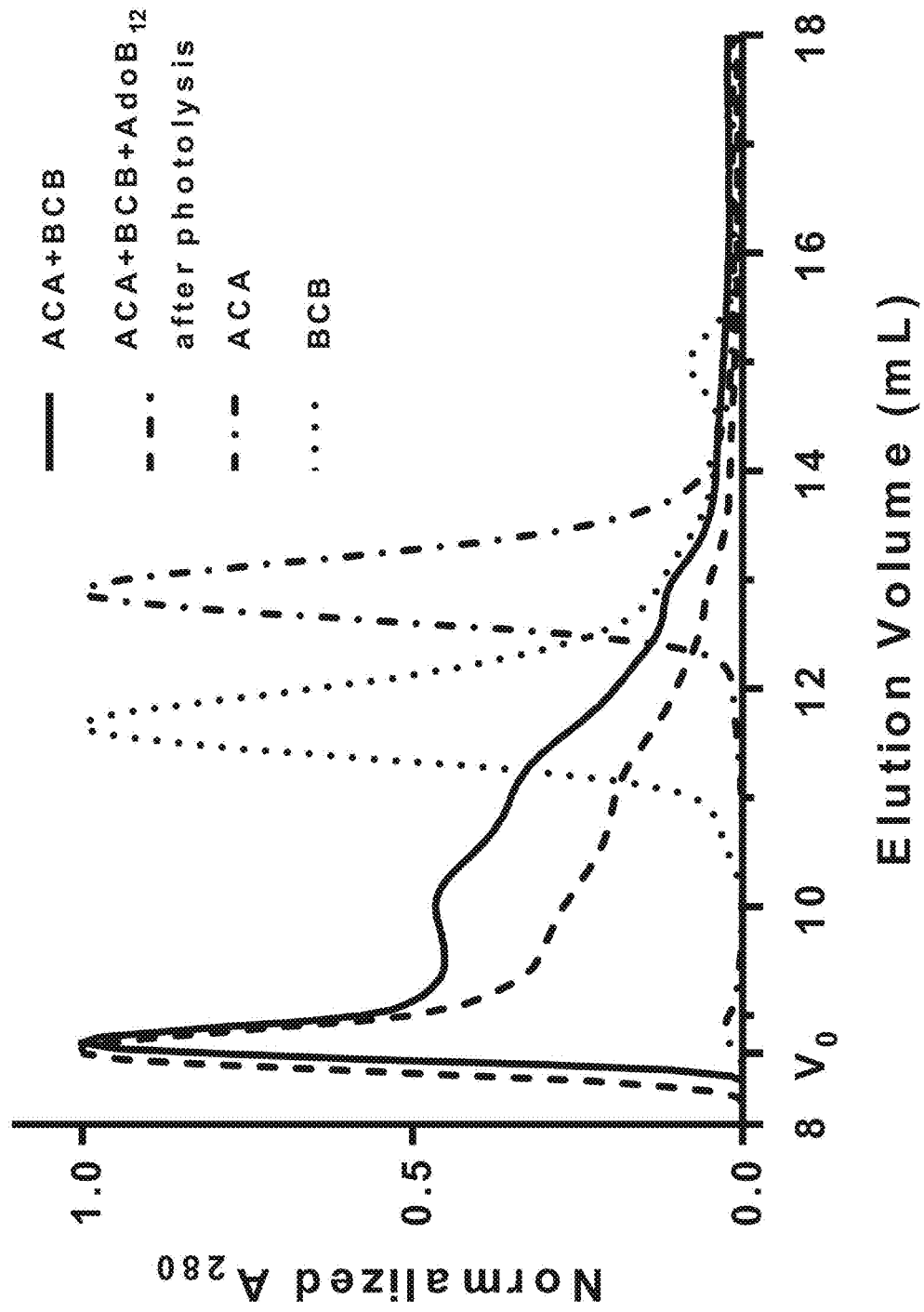
FIG. 9 shows SEC (size-exclusion chromatography) traces of the reaction product of ACA+BCB, the photolytic product of the ACA+BCB+AdoB12, ACA and BCB. The light-sensitive protein hydrogel comprising ACA+BCB AdoB12 was exposed to White light (comprising a wavelength between about 300 nm and about 600 nm) for complete degradation before the SEC analysis.

Using an *Escherichia coli* expression system, sufficient amounts of the ACA (98 mg/L) and BCB (66 mg/L) proteins with high purity (FIG. 6-9) were produced and isolated. After extensive dialysis against distilled water and lyophilization, the resulting protein powders were readily dissolved in PBS. The two protein solutions, ACA and BCB (10 wt % in PBS), were mixed at an equimolar ratio immediately followed by addition of a stoichiometric amount of $AdoB_{12}$ to initiate gelation at room temperature in the dark. A red gel-like material was formed within 5 min; the gelation typically continued for at least 7 h in the dark before any subsequent analysis. The resulting gel was sensitive to light and converted to liquid on exposure to white LED light (30 klux) within 20 min (FIG. 2B). The observed gel-sol transition can be explained by the light-induced disassembly of $CarH_C$ tetramers (FIGS. 1A & 1B). A subsequent size-exclusion chromatography (SEC) analysis showed that the major elution peak of the light-degraded products as well as that of the reaction products of ACA+BCB in the absence of AdoB$_{12}$ appeared at the void volume (V$_0$; 8.7 mL), corresponding to a molecular weight that exceeds the exclusion limit (2×106) (FIG. 9). This SEC result further confirmed a sufficient pymerization of the CarH$_C$ proteins enabled by the SpyTag-SpyCatcher reaction during gelation.

Example 3. Physical Properties of CarH$_C$ Hydrogels (Also Referred to as "Light-Sensitive or Photosensitive Protein Hydrogels")

Figure 10A:
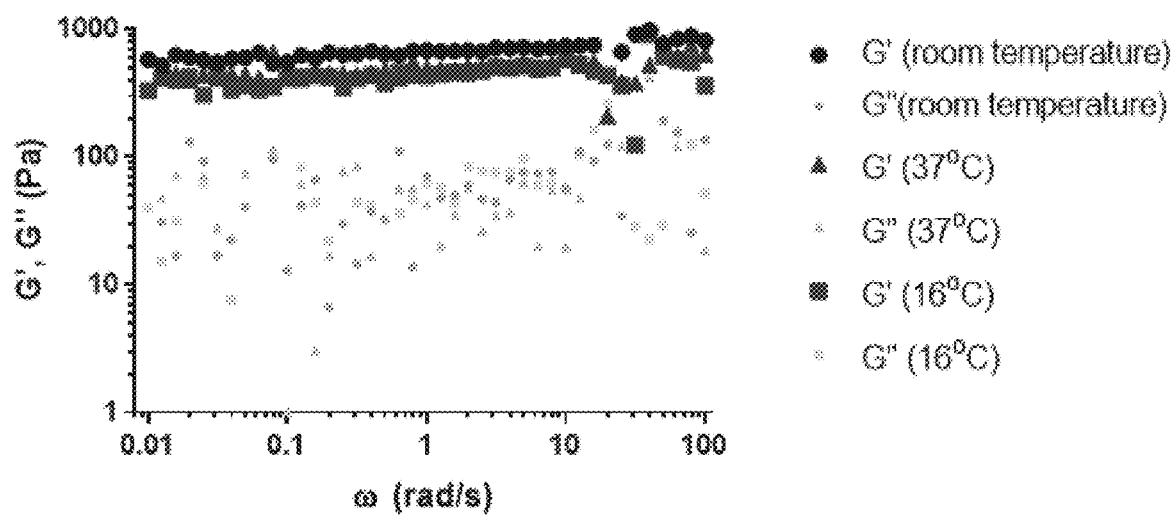
FIG. 10A shows the frequency sweep measurements performed in the dark with the strain fixed at 5% on the physically self-assembled light-sensitive protein hydrogels comprising CarHc composed of the linkage structure ACA+BCB+AdoB12 at different temperatures including room temperature (25, 37, and 16° C.).
Figure 10B:
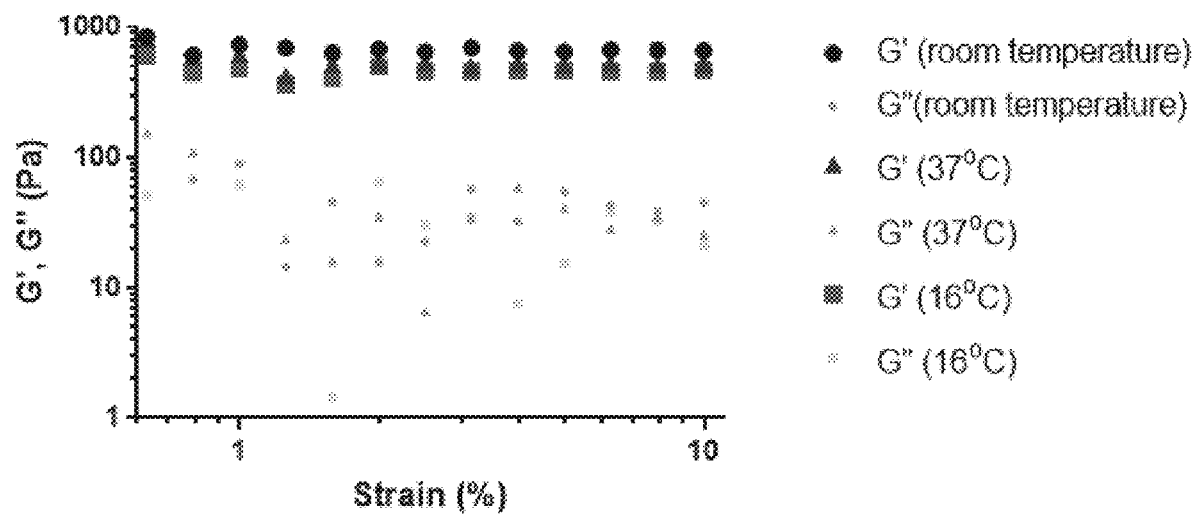
FIG. 10B shows the strain sweep measured performed in the dark with the frequency fixed at 1 rad/sec on the physically self-assembled light-sensitive protein hydrogels comprising CarHc composed of the linkage structure ACA+BCB+AdoB12 at different temperatures including room temperature (25, 37, and 16° C.).

Dynamic shear rheology was performed to monitor the gelation process. Simply mixing ACA and BCB in the absence of the AdoB$_{12}$ cofactor only led to a liquid-like material that exhibited a very low storage modulus G' (FIG. 2A). However, the reaction of ACA+BCB in the presence of AdoB$_{12}$ under dark conditions led to a gradually increased storage modulus G' that reached a steady value of ~0.66 kPa after 7 h and a much lower loss modulus G" (~0.04 kPa), suggesting that AdoB$_{12}$-mediated CarH$_C$ tetramerization is essential for the hydrogel formation (FIG. 2A). The G' of the hydrogel quickly dropped under constant light exposure, reflecting a typical gel-sol transition process (FIG. 2B), and the rates of the transition were affected by the light intensity (FIG. 2C). A stepwise gel-sol transition was also achieved by exposing the hydrogel to a pulsed light (FIG. 2D). Given the noncovalent nature of CarH$_C$ tetramerization, the CarH$_C$ hydrogel composed of ACA+BCB displays frequency-dependent viscoelastic properties. However, the frequency sweep test on the CarH$_C$ hydrogel at room temperature (25° C.) showed a steady storage modulus (0.58-0.81 kPa) over an angular frequency of 0.01-100 rad/s (FIG. 10A), which is indicative of static interchain interactions. One possible explanation is that the CarH$_C$ tetramers within the hydrogel network are kinetically inert, of which the disassembly or exchange takes longer than the timescale for the lowest shear frequency tested (628 s). Assuming that all of the CarHc domains form tetramers, a theoretical estimate of the G' of the CarHc hydrogel (8.3 wt %) is ~0.94 kPa based on G=ρRT/Mc, where the average molecular mass between cross-links M$_c$ is ~218 kDa (2ACA+2BCB). The observed G' matches well with the theoretical estimate, suggesting the sufficient assembly of the CarHc domains within the hydrogel network. The CarH$_C$ hydrogel also exhibited stability toward mechanical deformation (1-10% strain) as revealed by the strain-sweep test at room temperature (FIG. 10B).

The ELP (elastin-polypeptide, also referred to as "elastin") domains are known to have a unique phase transition behavior at a lower critical solution temperature (LCST). The LCST of the ELP domain that was selected was 25° C. to 30° C. To investigate the influence of temperature on these ELP-based hydrogel properties, rheology studies on the hydrogels were performed at different temperatures (16° C., 25° C., and 37° C.) and little change in their rheological behaviors was observed, suggesting that the phase transition of ELPs has negligible effects on macroscopic mechanical properties of the materials.

Figure 11:
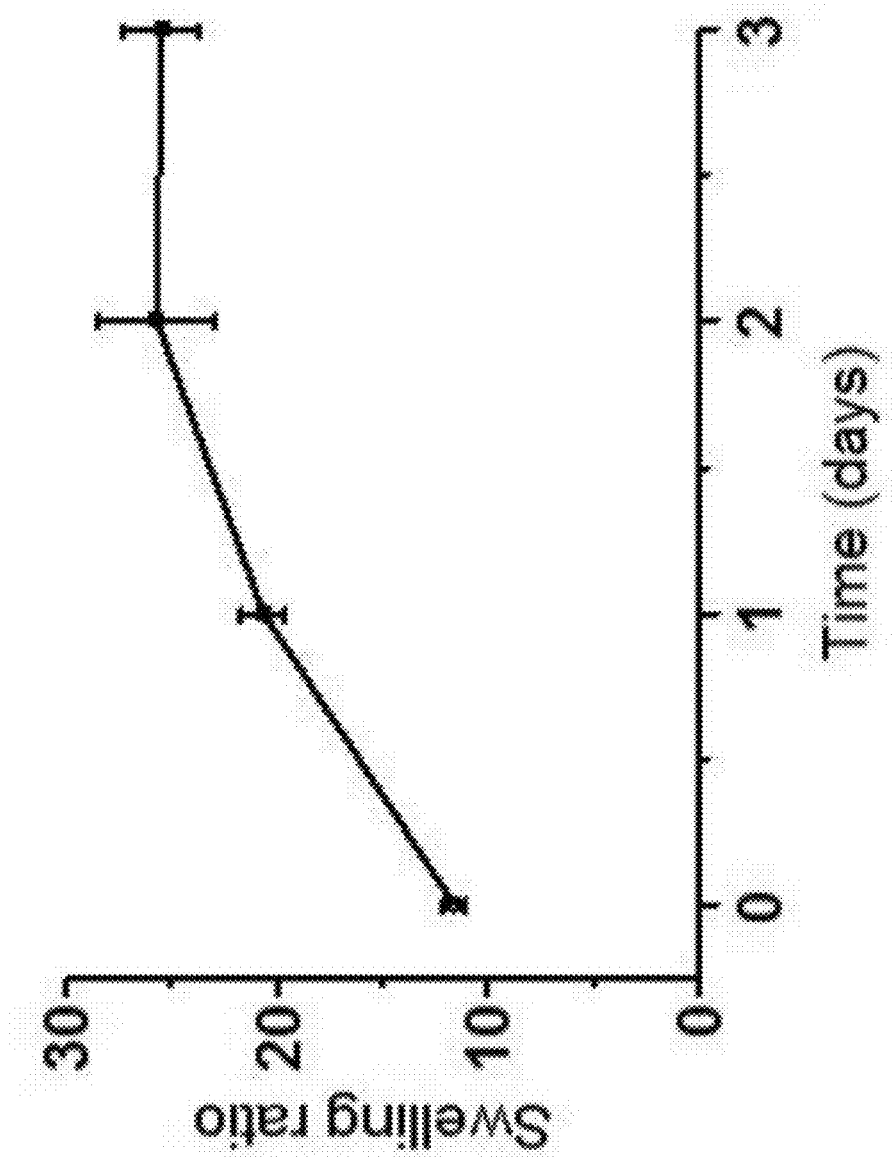
FIG. 11 shows the swelling of the physically self-assembled light-sensitive protein hydrogels comprising CarHc composed of the linkage structure ACA+BCB+AdoB12 at room temperature in the dark. Error bars indicated the standard deviations from three independent measurements.
Figure 12:
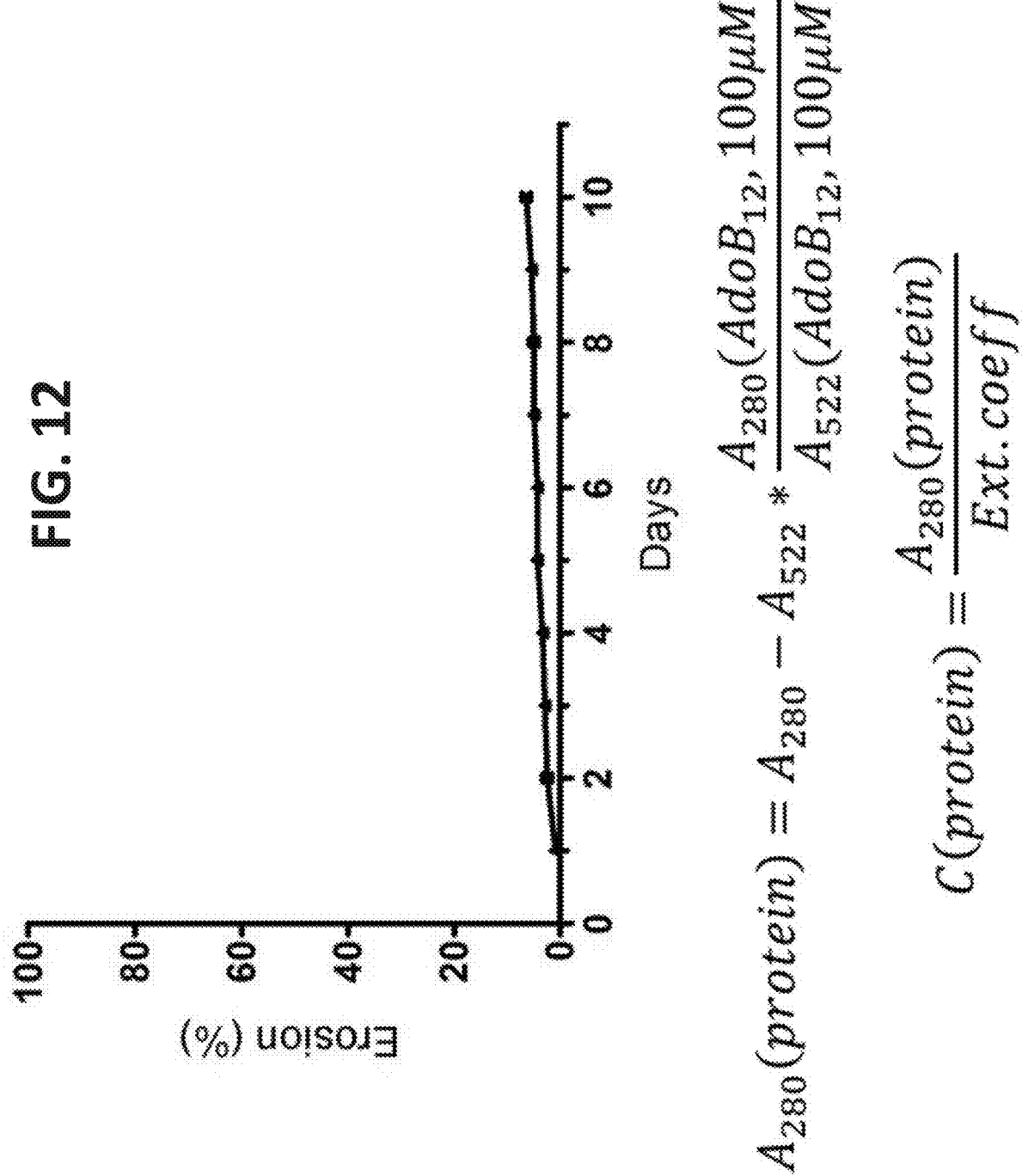
FIG. 12 shows the erosion profile of the physically self-assembled light-sensitive protein hydrogels comprising CarHc composed of the linkage structure ACA+BCB+AdoB12 at room temperature in the dark. The hydrogels were prepared by mixing 31 uL BCB (10 wt. % in PBS), 19 uL ACA (10 wt. % in PBS), and 10 uL AdoB12 (0.2 mM in PBS) and allowed to cure at room temperature in the dark for 24 h before being immersed by 1 mL PBS (day 0). From day 1, 5 uL supernatant was extracted for analysis every 24 h. The protein concentration was calculated based on the following equations: A(280)[protein]=A(280)−A(522)*{A (280)[AdoB12, 100 μM]/A(522)[AdoB12, 100 μM]}, and Conc.(protein)=A(280)[protein]/ext. coeff.

The CarH$_C$ hydrogel comprising ACA+BCB+AdoB$_{12}$ exhibited moderate swelling in PBS at room temperature, and the swelling ratio, calculated as the ratio of the wet gel weight to the city protein weight, reached maximum (~25) from an initial ratio of 12 within 3 d (FIG. 11). The hydrogel is also stable. Only ~6% of the gel was eroded in the presence of excess PBS at room temperature after 10 d (FIG. 12).

Example 4. Cell Encapsulation and Light-Induced Release/Recovery

A 3D cell culture system that allows cells to be encapsulated and readily released/recovered without resorting to complicated chemical or proteolytic degradation is important for the study of cell matrix interactions and tissue engineering applications. The CarH$_C$ hydrogel comprising the linkage structures ACA+BCB+AdoB$_{12}$ undergoes a rapid gel-sol transition on light exposure which allows for facile recovery and release of cells after 3D culturing. First, the cytocompatibility of the CarHc hydrogel using mouse 3T3 fibroblasts and human mesenchymal stem cells (hMSCs) was examined. To encapsulate the cells, the BCB solution containing the cells was mixed thoroughly with the ACA solution at a 1:1 molar ratio followed by adding a stoichiometric amount of AdoB$_{12}$ to initiate gelation in the dark. After 2 h of curing, the gels were covered with culture medium and incubated under standard conditions (37° C. at 5% CO$_2$) away from light. After 24 h, a live/dead staining was performed to examine the cell viability. Most of the embedded fibroblasts (88±3%) and mesenchymal stem cells (MSCs; 92±2%) remained viable (FIGS. 3A & 3B), indicating that the CarH$_C$ hydrogel is nontoxic to these cells.

Rapid gelation is required by cell encapsulation applications. The gelation rate of the CarH$_C$ hydrogel system depends on two events: the SpyTag-SpyCatcher reaction and AdoB$_{12}$-dependent CarH$_C$ self-assembly. The SpyTag-SpyCatcher reaction is likely to be the rate-limiting step, because its second-order rate constant is 1.4×10$^3$M$^{-1}$s$^{-1}$, which is far from the diffusion limit and substantially slower than some other biomolecular interactions, such as the streptavidin-biotin interaction. In some embodiments, the reaction kinetics of SpyTag-SpyCatcher can be optimized through directed evolution to accelerate the gelation. In some alternative embodiments, the efficiency of CarH$_C$ self-assembly can be improved through protein engineering, so that a hydrogel system solely based on the CarH$_C$ tetramerization can be developed to enable swift cell encapsulation.

Figures 4A, 4B, 4C, 4D:
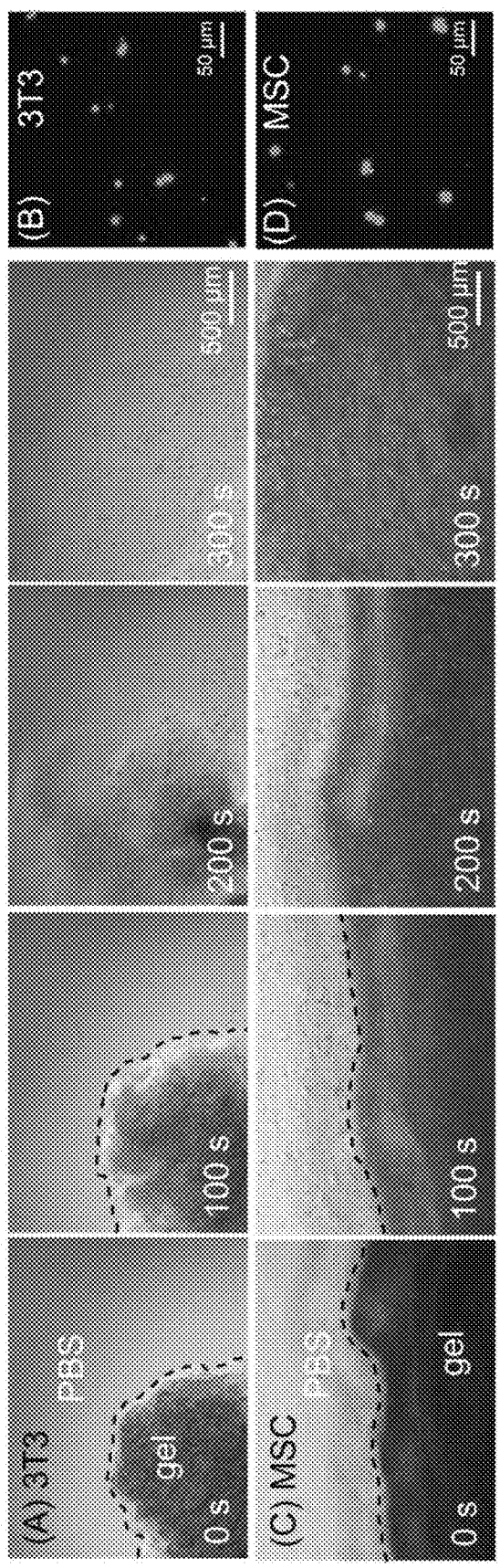
FIG. 4A shows the release of encapsulated cells by light-induced gel-sol transition, where the cells are mouse 3T3 fibroblasts.
FIG. 4B shows the live/dead staining of recovered 3T3 fibroblasts. For both FIG. 4A and FIG. 4B, the cells are encapsulated by light-sensitive protein hydrogels comprising CarHc (red) and cultured for 24 hrs. Cell release was initiated by exposing the 3D cell culture to white light (22 klux). The hydrogel is immersed in PBS buffer. Representative bright-field micrographs (0, 100, 200, and 300 seconds after light exposure) are shown. Dashed lines indicate the gel boundaries.
FIG. 4C shows the release of encapsulated cells by light-induced gel-sol transition, where the cells are hMSCs.
FIG. 4D the live/dead staining (live—green; calcein AM; dead—red; ethidium homodimer) of recovered hMSCs.

The cell-laden gels were exposed to white light comprising a wavelength between about 300 nm and about 600 nm to recover the aforementioned encapsulated cells. The cells migrated along with the melting gel, indicating that these cells were indeed encapsulated in a 3D manner (FIGS. 4A-4D). Within 5 min, the gels were completely transformed into liquid accompanied with a complete release of the cells. The live/dead staining showed that the majority of recovered cells (3T3: 90±7%; MSCs: 88±5%) remained viable, indicating that the photolysis of the CarH$_C$ hydrogels is amicable to the encapsulated cells (FIG. 4B and FIG. 4D). The photodegradation of AdoB$_{12}$ in CarH does not use a typical radical mechanists, and its photolytic product is 4',5'-anhydroadenosine instead of more common 5'-dAdo radicals, Although adenosine could lead to cytotoxicity at relatively high concentrations or after prolonged exposure, there has been no direct evidence pointing to the cytotoxicity or any other side effect of its analog 4',5'-anhydroadenosine on cell phenotypes. In addition, only trace amounts of unbound AdoB$_{12}$ (1 µM) exists in the CarH$_C$ hydrogel (8.3 wt %) given the dissociation constant K$_d$ for the AdoB$_{12}$-CarH complex (0.8 µM). Therefore, the radical species resulting from the photolysis of the free AdoB$_{12}$ is negligible and can hardly cause cytotoxicity. Both the nonradical photolysis of the AdoB$_{12}$ binding CarH$_C$ and the very low concentration of the free AdoB$_{12}$ contribute to the high viability of these cells recovered from the protein hydrogels.

Example 5. Light-Induced Protein Release

Figure 13:
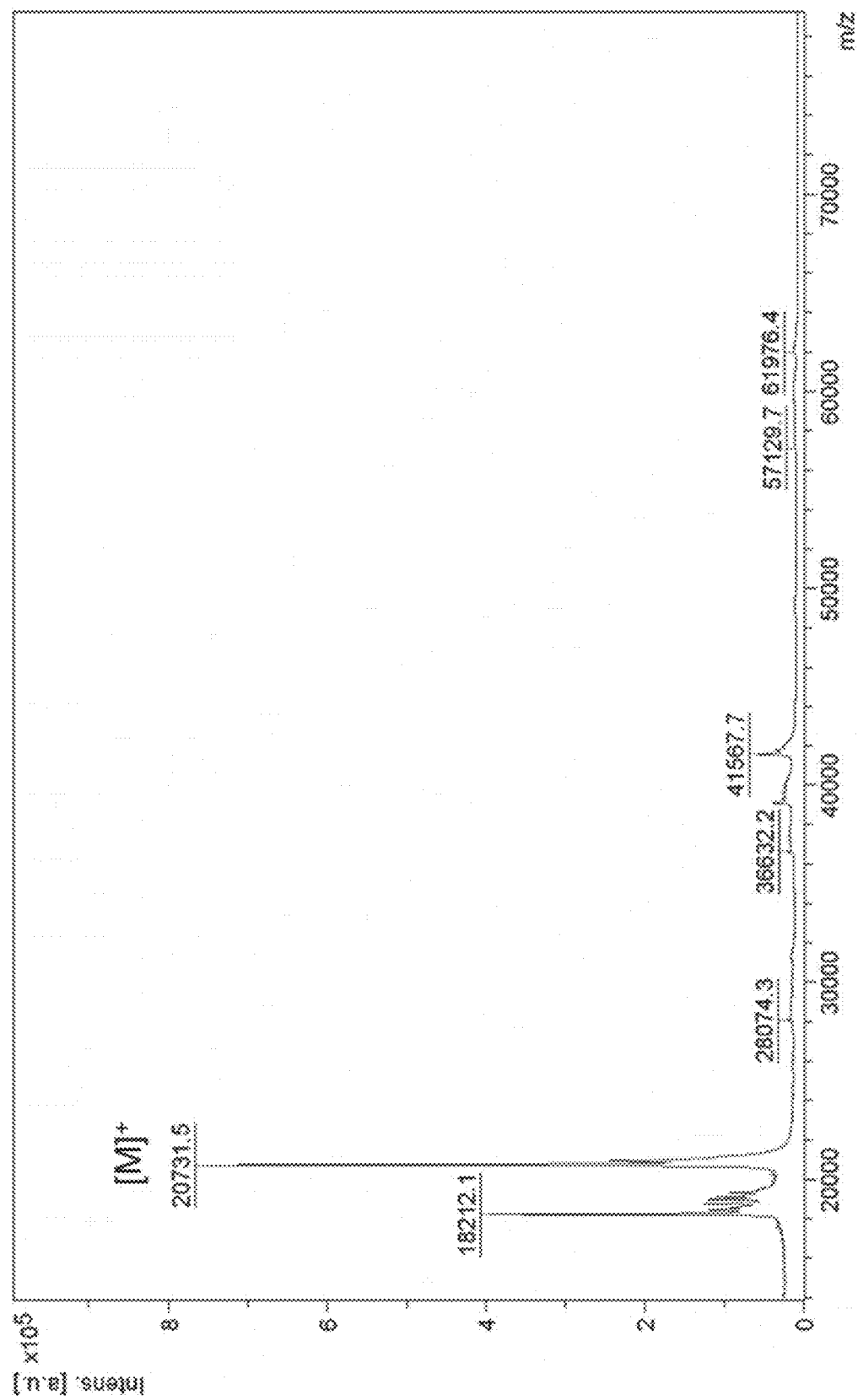
FIG. 13 shows the MALDI-TOF mass spectrum of the telechelic protein with the linkage structure of "AAA".
Figure 15:
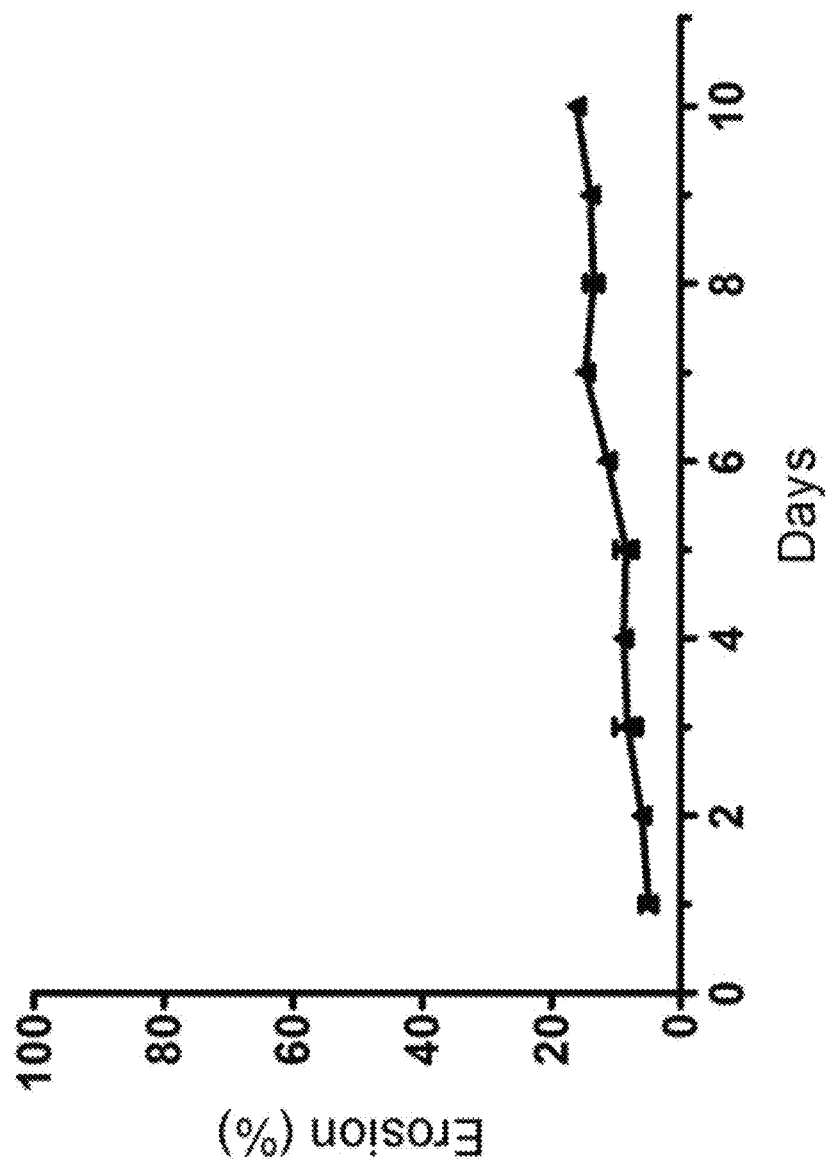
FIG. 15 shows the erosion profile of the physically self-assembled light-sensitive protein hydrogels comprising CarHc composed of the linkage structure AAA+BCB+AdoB12 at room temperature in the dark. The hydrogels were prepared by mixing 31 uL BCB (10 wt. % in PBS), 19 uL AAA (10 wt. % in PBS), and 10 uL AdoB12 (0.2 mM in PBS) and allowed to cure at room temperature in the dark for 24 h before being immersed by mL PBS (day 0). From day 1, 5 uL supernatant was extracted for analysis every 24 h.

Protein drugs, an important category of modern therapeutics, have a short half-life time inside the body because of rapid plasma clearance and proteolytic degradation, which constitutes a fundamental challenge for their delivery. The feasibility of using the photoresponsive CarH$_C$-ELP hydrogel system to encapsulate and release protein molecules in a controlled manner was investigated. Two recombinant proteins, SpyTag-elastin-like polypeptide-SpyTag-elastin-like polypeptide-SpyTag (represented by the structural linkage "AAA") (FIG. 6 and FIG. 13) and BCB, were synthesized with an elastin protein fragment to generate a covalently cross-linked ELP hydrogel. The two proteins were dissolved in PBS to make 10 wt % solutions. Gelation was initiated by mixing the two components at a 2:3 molar ratio and a stoichiometric amount of AdoB$_{12}$ in the dark. Dynamic shear rheology experiments in time-, frequency- and strain-sweep modes and erosion tests further confirmed the formation of a stable hydrogel (G'=0.96 kPa and G"=0.03 Pa) by AAA+BCB+AdoB$_{12}$ (FIGS. 14A-14C, respectively, and FIG. 15).

Figure 5A:
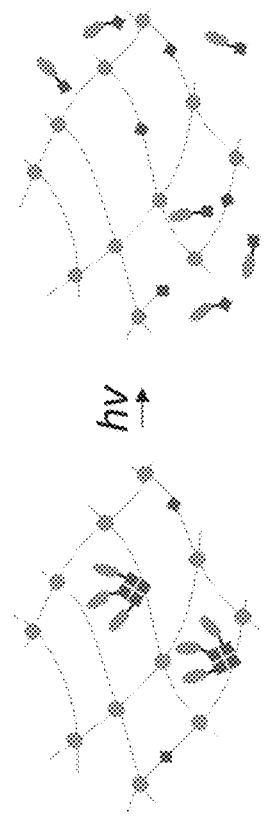
FIG. 5A shows protein immobilization and light-induced release enabled by the covalently cross-linked light-sensitive protein hydrogels comprising CarHc with a schematic showing the immobilization and release of the mCherry-CarHc protein. The hydrogel (8.6 wt %) is composed of AAA and BCB at a 2:3 molar ratio, a stoichiometric amount of AdoB12, and the fusion protein mCherry-CarHc (50 μM). CarHc tetramerization leads to the mCherry immobilization into the hydrogel in the dark. The photolysis of AdoB12 disassembles tetrameric CarHc and facilitates the release of mcherry-CarHc.
Figure 5B:
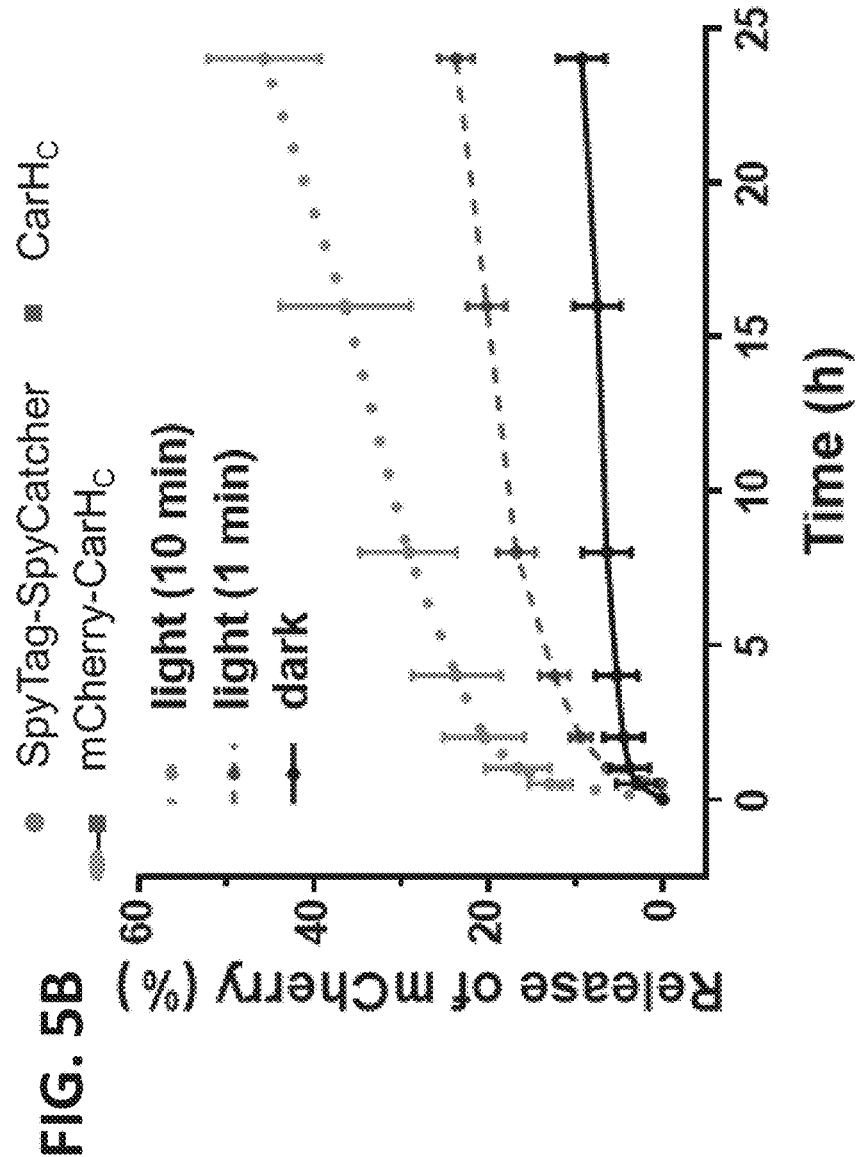
FIG. 5B shows the release profiles of mCherry-CarHc from the hydrogels that were subjected to 0, 1, and 10 min of white light exposure. The percentage release of mCherry was calculated based on the total amount of mCherry added into the gel. Error bars show SDs from three independent measurements.
Figure 6:
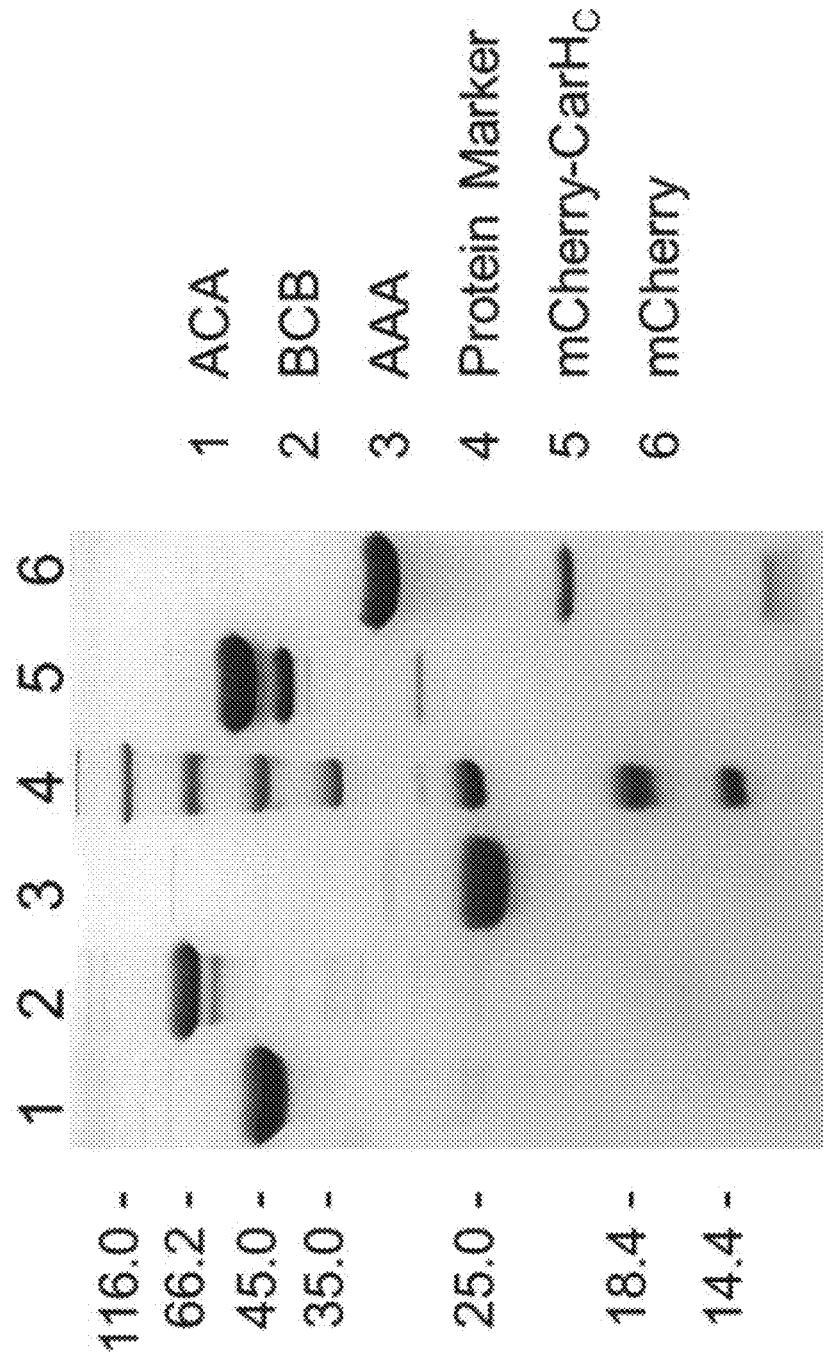
FIG. 6 shows the SDS-PAGE analysis of the expressed proteins purified by Ni-NTA chromatography.
Figure 7:
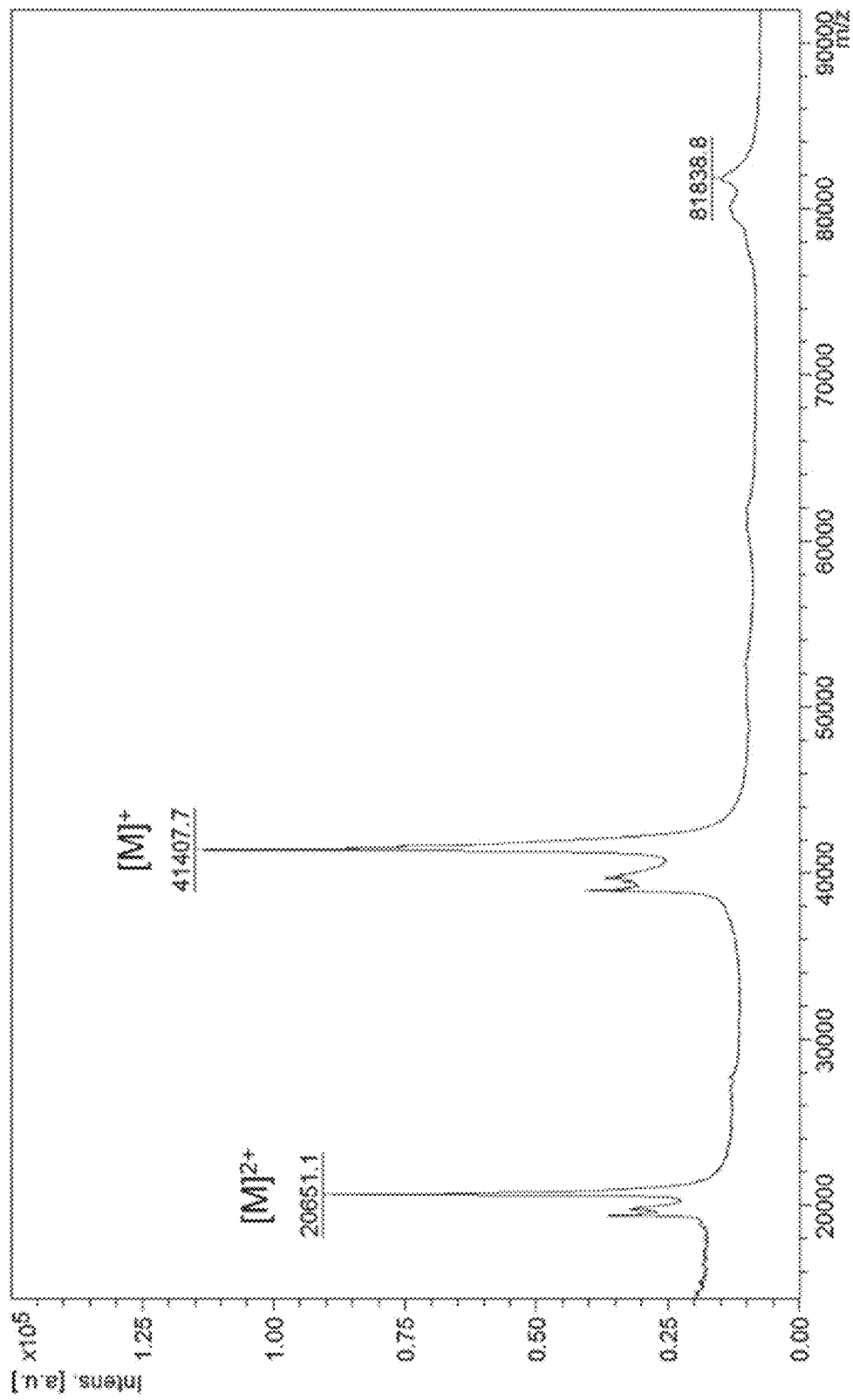
FIG. 7 shows the MALDI-TOF mass spectrum of the telechelic recombinant protein with the linkage structure of "ACA", where A is SpyTag and C is ApoCarHc.
Figure 8:
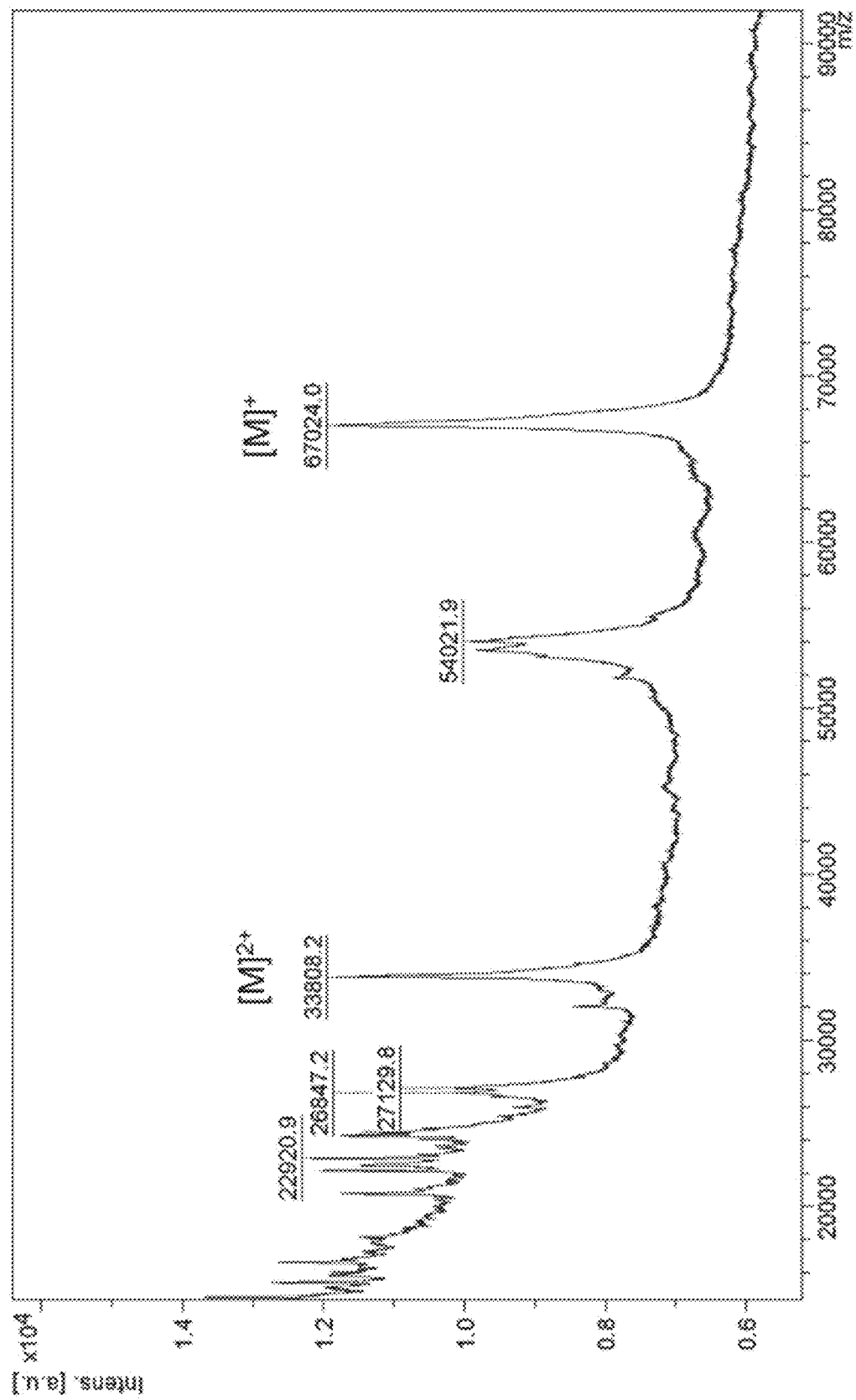
FIG. 8 shows the MALDI-TOF mass spectrum of the telechelic recombinant protein with the linkage structure of "BCB", where B is SpyCatcher and C is ApoCarHc.
Figure 16:
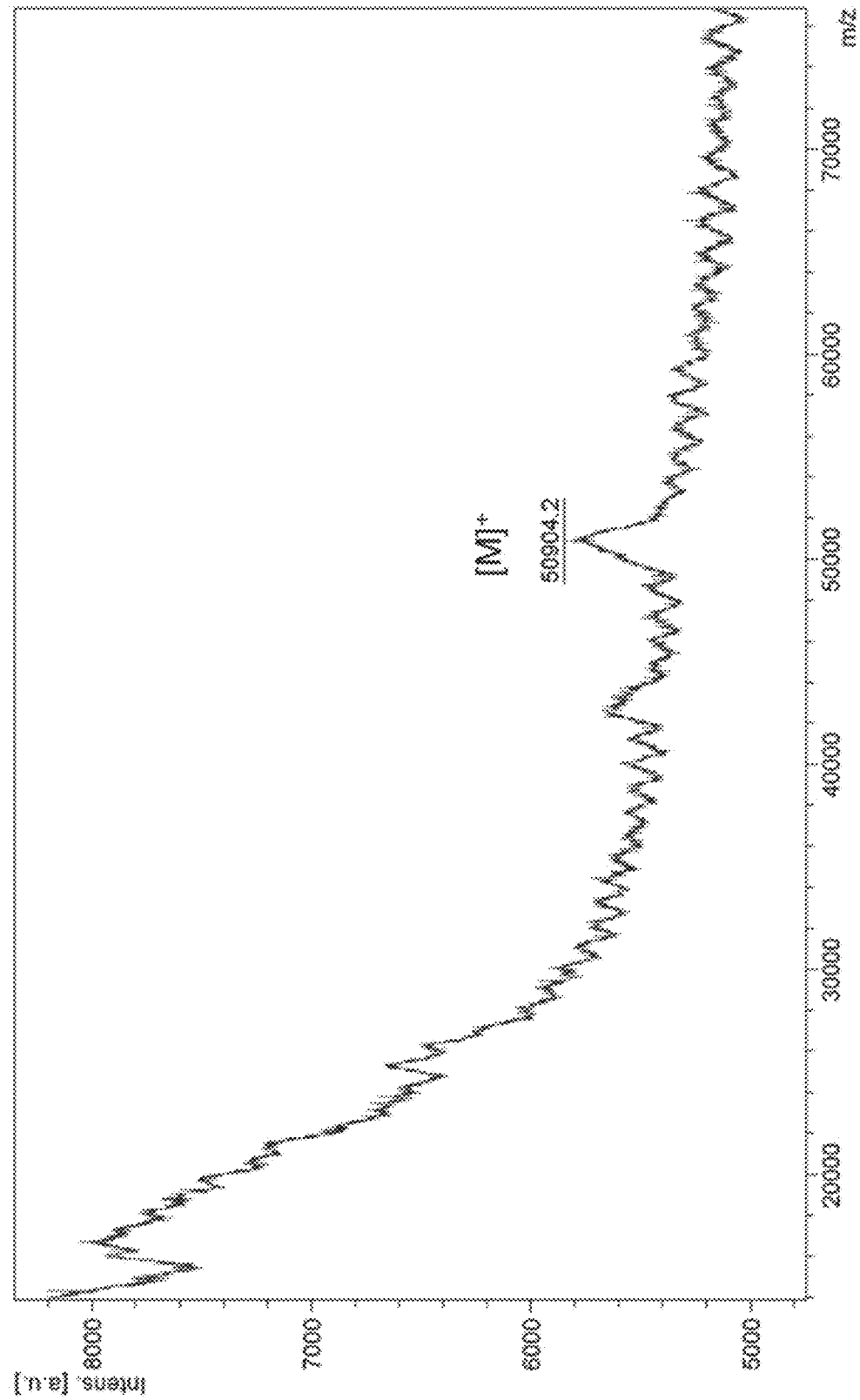
FIG. 16 shows the MALDI-TOF mass spectrum of mCherry-CarHc.
Figure 17:
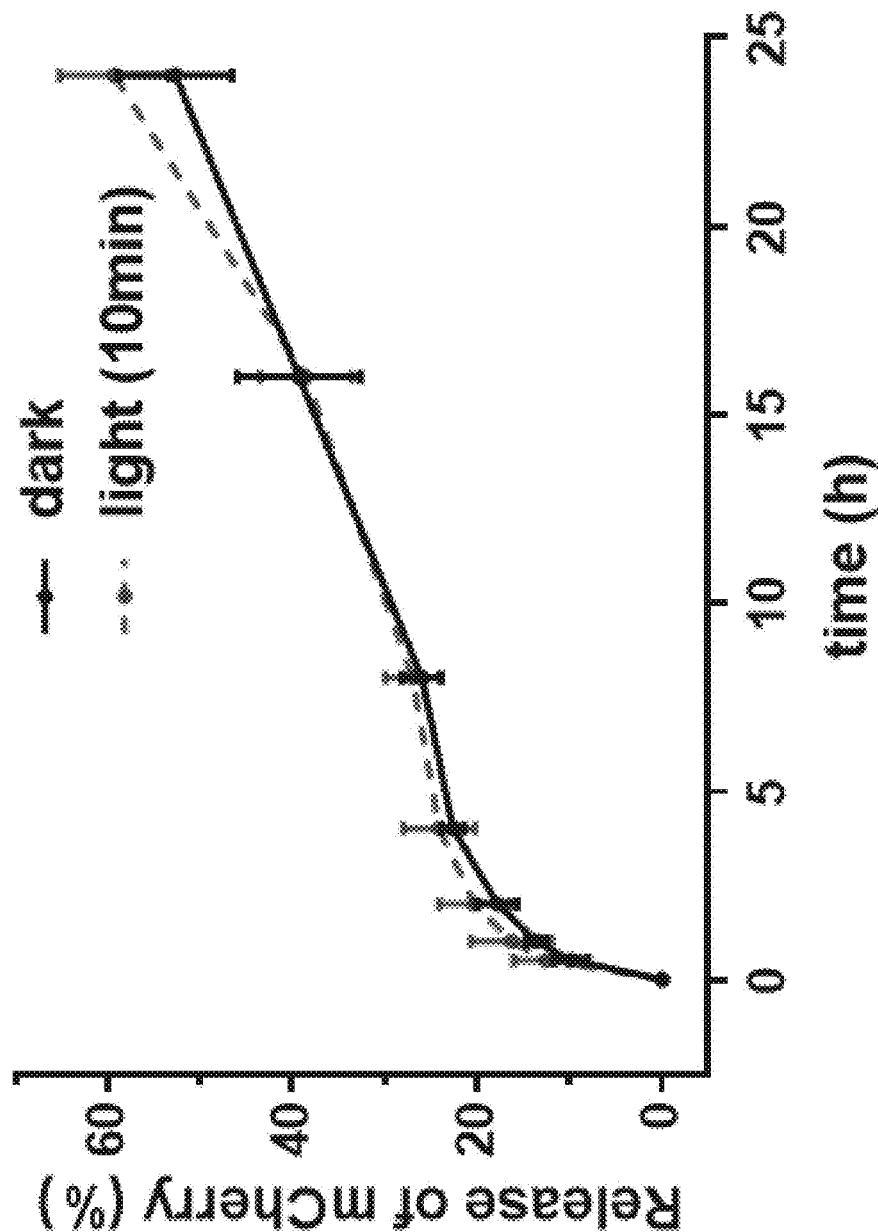
FIG. 17 shows the release of mCherry from the covalently cross-linked light-sensitive polymer hydrogel comprising CarHc comprised of the linkage structure AAA+BCB+AdoB12. The mCherry protein is physically encapsulated by the light-sensitive protein hydrogel. Light (comprising wavelength between about 300 nm and about 600 nm) for 10 min did not affect the release of mCherry in the absence of the CarHc domain. Error bars show SDs from three independent experiments.
Figure 21B:
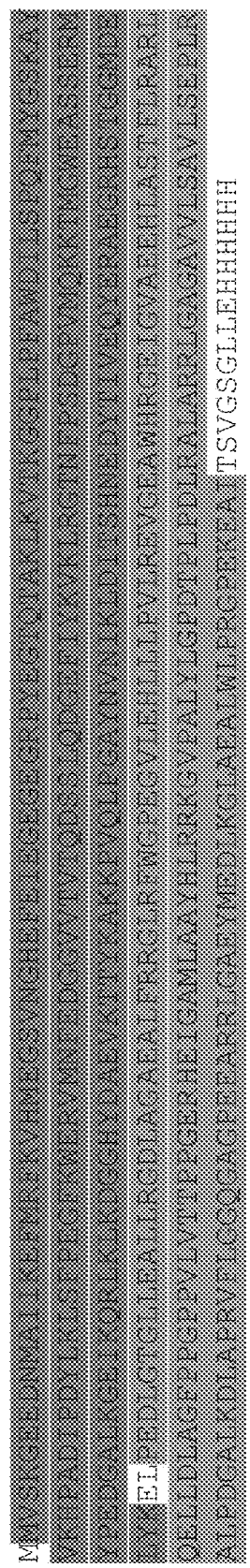
FIG. 21B shows the polypeptide sequence information of the linkage structure mCherry-CarHc (SEQ ID NO: 6). The segments in purple and green are mCherry and CarHc, respectively.

To test the feasibility of this covalently cross-linked CarH$_C$ hydrogel for controlled protein release, a recombinant CarH$_C$-fusion mCherry protein was constructed and used as a model substrate (FIG. 1 and FIG. 16). The model fusion protein complex mCherry-CarH$_C$ protein can be physically tethered to the hydrogel network through AdoB$_{12}$-dependent CarH$_C$ self-assembly in the dark and light exposure disassembles the CarH$_C$ tetramers and facilitates the release of mCherry-CarH$_C$ (FIG. 5A). Three sets of mCherry-CarH$_C$-decorated hydrogels were synthesized and immersed in PBS; two were exposed to the white LED light (90 klux) for 1 and 10 min before being moved to the dark, and the third one was kept in the dark all of the time. Aliquots of the supernatant were taken to analyze the release of mCherry over 24 h. FIG. 5B shows that about 24 and 45% of mCherry-CarH$_c$ were released from the gels that were subjected to 1- and 10-min light exposure, respectively, after 24 h, whereas the release was substantially slower in the gel always kept in the dark with less than 10% of mCherry-CarH$_C$ released. This result indicate that controlled protein release in this system can be readily achieved by adjusting the duration of the light exposure. For the mCherry protein lacking the CarH$_C$ domain, its release from the AAA+BCB hydrogel was light-independent, because similar amounts of free mCherry (~50%) were detected in the supernatants under the dark and bright conditions, further corroborating that the CarH$_C$ domain is essential for the light-controlled release (FIG. 17) It is also noteworthy that, despite two tobacco etch virus (TEV) protease cleavage sites in the BCB construct, the covalently cross-linked hydrogels composed of AAA+BCB+AdoB$_{12}$ were resistant toward TEV digestion at room temperature under both dark and bright (white LED light; 90 klux) conditions (FIG. 18). These ELP-based covalent networks served as physical barriers to protect the encapsulated proteins/peptides from proteolysis, even after photolysis. These results demonstrate the feasibility of using the photoresponsive CarH$_c$ hydrogel for controlled protein delivery/release.

This light-sensitive protein hydrogel system represents one embodiment of using AdoB$_{12}$ photochemistry to control the material properties and thus, supports a versatile strategy for creating photoresponsive materials.

Example 6: Preparation of Light-Responsive Protein-Based Hydrogel

ACA and BCB proteins were dissolved in PBS to yield 10 wt % solutions. Adenosylcobalamin was dissolved in PBS to a final concentration of 9.2 mM. ACA and BCB were mixed at an equimolar ratio followed by addition of a stoichiometric amount of adenosylcobalamin in the dark at room temperature.

Example 7: Mammalian Cell Encapsulation and Culture

Around 60,000 freshly isolated cells were pelleted and resuspended with 31 µL BCB in DMEM (10 wt %) and then placed on a cell culture dish with a coverslip bottom, Gelation was initiated by adding 19 µL ACA in PBS (10 wt %) and 10 µL AdoB12 in PBS (9.2 mM). The gel (FIG. 22) was cured in the dark for 1 hr before being covered with the culture medium, which was replaced by new medium every 3 days.

Example 8: Light-Controlled Cell Release From Hydrogel

Figure 3A:
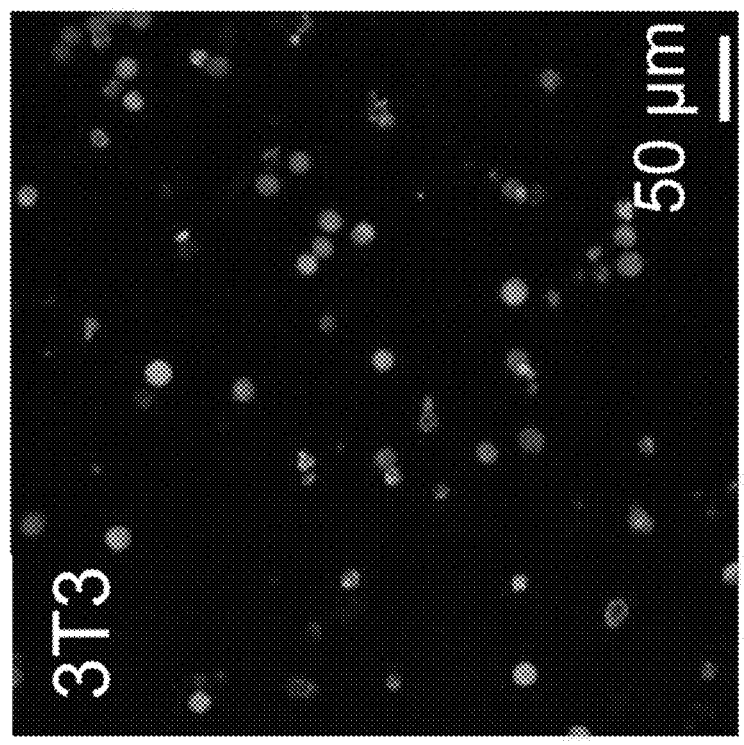
FIG. 3A shows the encapsulation of 3T3 fibroblasts by the physically assembled light-sensitive (or photosensitive) protein hydrogels comprising a plurality of CarHc, each CarHc comprising the linkage structure of ACA+BCB+AdoB12.

Cell-laden gels were rinsed and immersed by PBS before exposure to white light (halogen lamp in the microscope, 22 klux) for 5 minutes to release cells (FIGS. 4A-4D). Cells remained alive as proven by live/dead staining (FIGS. 3A & 3B).

Example 9: Mammalian Cell Subculture

Cells (3T3 fibroblasts) released from Example 8 were pelleted by centrifugation, and then resuspended in BCB following the methods described in Example 7, and further encapsulated in a new piece of hydrogel for another round of culture. FIG. 24A shows the live/dead stain of cells released once, then FIG. 24B shows further encapsulated in a new piece of hydrogel then released again. The results show the cells remain alive after multiple capture/culture/release steps.

Example 10: Cell Capture and Release of Neuronal Cells

Figure 23:
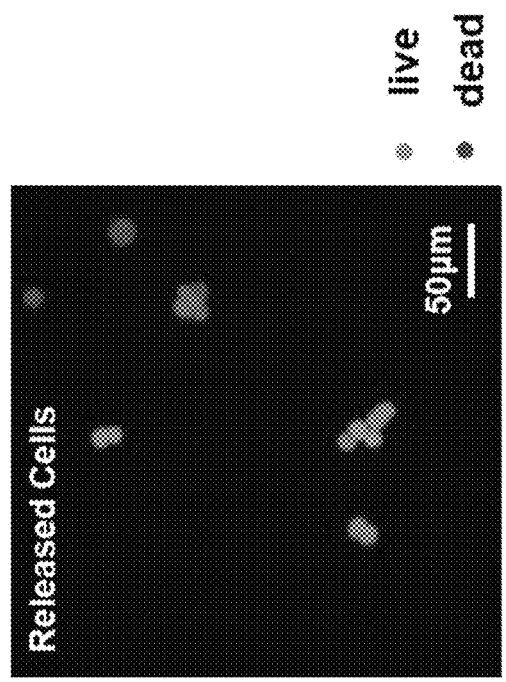
FIG. 23 shows the encapsulation of MSCs by the physically assembled light-sensitive (or photosensitive) protein hydrogels comprising a plurality of CarHc, each CarHc comprising the linkage structure of ACA+BCB+AdoB12. Representative confocal fluorescence z-slice micrographs of live (green; calcein AM) and dead (red; ethidium homodimer) cells.

PC-12 cells representing neuronal cells were captured and released as described above for Example 4. FIG. 23 shows the live/dead staining of recovered PC-12 neuronal cells, indicating that all cells remained alive after release from the protein hydrogel. This experiment demonstrates that a multitude of cell types can be captured, cultured, and release by the methods described herein.

Example 11: Post-Release Cell Content Analysis

Cells embedded in gels can be treated with drug or functional chemicals. After a selected period of time, cells can be isolated from gels using light and enabled for use in transcription analysis, protein expression analysis, cell sorting, transplantation, etc.

Example 12: Controlled Drug Release

A therapeutic protein drug model (mCherry-CarHc) was encapsulated in the hydrogel before exposure to light comprising a wavelength between about 300 nm and about 600 nm (FIG. 5A). The protein release profile can be controlled by tuning incident light exposure time (FIG. 5B).

Example 13: Potential Treatment of Skin Cancer

Subjects with skin cancer in principle can be treated by parental administration with a light-sensitive protein hydrogel comprising a therapeutic protein and/or antibody and/or cell of the Examples described herein at a dose of between 0.01 and 0.5% (w/w), with additional applications of the hydrogel composition administered as needed.

Example 14: Potential Optically Controlled Therapeutic Delivery in Deep Tissue

Photosensitive protein hydrogels comprising native AdoB12 are not responsive to white light when imbedded deep in tissue. However, a photosensitive protein hydrogel comprising AdoB12 connected to a photosensitizer, wherein the photosensitizer is a fluorophore, can make the protein responsive to infrared light which is transparent to the skin and tissue (52). Encapsulated cells in a photosensitive protein hydrogel comprising AdoB12 connected to a photosensitizer, wherein the photosensitizer is a fluorophore, can be prepared as described herein. The formulated encapsulated cells can be embedded under the tissue, then irradiated with infrared light which releases the encapsulated cells. In some embodiments, 2-photon excitation can be used to trigger the release of protein therapeutics from this type of light-responsive protein hydrogels in deep tissue.

Example 15: Synthesis of Cobalamin Derivatives

Synthesis and Characterization of Cobalamin-TAMRA Conjugate (Cbl-1)

Synthesis of β-(3-aminopropyl)cobalamin 1: β(3-aminopropyl)cobalamin 1 can be prepared from hydroxocobalamin and 3-chloropropylamine hydrochloride according to a literature procedure (C. G. Bochet, Angew. Chem. 2001, 113, 2140-2142; Angew. Chem. Int. Ed. 2001, 40, 2071-2073, herein incorporated by reference). Purification can be achieved according to literature procedure (L. T. Nguyen, N. P. Oien, N. L. Allbritton, D. S. Lawrence Angew. Chem. 2013, 125, 10120-10123) to afford an orange solid; the compound is can be characterized by ESI MS, electrospray mass spectrometry.

Synthesis of Cobalamin-TAMRA Conjugate (Cbl-1): Cbl-1 can be prepared from β-(3-aminopropyl)cobalamin 1 and 5-carboxytetramethylrhodamine (TAMPA) according to a literature procedure (C. G. Bochet, Angew. Chem. 2001, 113, 2140-2142; Angew. Chem. Int. Ed. 2001, 40, 2071-2073, herein incorporated by reference). Purification can be achieved according to literature procedure (L. T. Nguyen, N. P. Oien, N. L. Allbritton, D. S. Lawrence, Angew. Chem. 2013, 125, 10120-10123) to afford a red solid; the compound is expected to be characterized by ESI MS calcd. for C90H118N16O18PCo (M2+): m/z=900.4, expected to be found 900.5; where calcd. for (M3+): m/z=600.3, expected to be found 600.3.

Synthesis and characterization of β-(3-acetamidopropyl) cobalamin (Cbl-2). Synthesis of β-(3-acetamidopropyl)cobalamin (Cbl2): Acetic acid (0.0022 g, 38 μmol), N,N,N',N'-tetramethyl-O—(N-succinimidyl)uranium tetrafluoroborate (TSTU, 0.0242 g, 80 μmol), and DIPEA (0.0234 g, 181 μmol), can be mixed for 1 h in a 2:2:1 dimethylformamide:dioxane:water solution (250 μL), β-(3-aminopropyl)cobalamin 1 can be added and the reaction can be mixed for 18 h. The desired compound can be purified by HPLC (semiprepative C-18 column) using a linear gradient binary solvent system (solvent A: 0.1% TFA/H2O; solvent B: 0.1% TFA/CH3CN) with a ratio of A:B that can vary from 97:3 (0 min) to 10:90 (40 min), Removal of solvent by lyophilization is expected to afford an orange solid which can be characterized by ESI MS.

Synthesis and Characterization of Cobalamin-Fluorophore Conjugates (Cbl3, Cbl4, Cbl5, Cbl6, and Cbl7)

General synthesis of cobalamin-fluorophore conjugates: The N-hydroxysuccinimide ester of a fluorophore (1 eq.), β-(3-aminopropyl)cobalamin 1 (1.5 eq.), and diisopropylethylamine (6 eq.) can be mixed in dimethylformamide for 18 h. The desired compound can be purified by HPLC (semiprepative C-18 column) using a linear gradient binary solvent system (solvent A: 0.1% TFA/H2O; solvent B: 0.1% TFA/CH3CN) with a ratio of A:B that can vary from 97:3 (0 min) to 10:90 (40 min). Removal of solvent by lyophilization is expected to afford a solid.

Cobalamin-SulfoCy5 Conjugate (Cbl-3): can be characterized by ESI MS.

Cobalamin-Atto725 Conjugate (Cbl-4): can be characterized by ESI MS.

Cobalamin-Dylight800 Conjugate (Cbl-5): can be characterized by ESI MS.

Cobalamin-Alexa700 Conjugate (Cbl-6): can be characterized by ESI MS.

Cobalamin-BODIPY650 Conjugate Cbl-Bod): can be characterized by ESI MS.

Synthesis and Characterization of Coenzyme B12-TAMRA Conjugate AdoCbl-1

Synthesis of coenzyme B12-ethylenediamine conjugate 2: Coenzyme B12 (0.0209 g, 13 μmol) and 1,1'-carbonyldi-(1, 2,4-triazole) (0.0142 g, 87 μmol) can be added to an oven-dried round bottom flask. The vessel can be purged with Ar. Dry dimethylformamide (0.2 mL) can be added to the flask and the mixture can be stirred at room temperature for 1 h. Ethylenediamine (0.0270 g, 450 μmol) can be added to the reaction mixture and stirring continued for another 18 h. The desired compound can be purified by HPLC (semiprepative C-18 column) using a linear gradient binary sol vent system (solvent A: 0.1% TFA/H2O; solvent B: 0.1% TFA/CH3CN) with a ratio of A:B that can vary from 97:3 (0 min) to 10:90 (40 min). Removal of solvent by lyophilization is expected to afford an orange solid which can be characterized by ESI MS.

Synthesis of coenzyme B12-TAMRA conjugate (AdoCbl-1): N,N,N',N'-Tetramethyl-O—(N-succinimidyl)uranium tetrafluoroborate (TSTU, 0.0139 g, 46 μmol), TAMRA (0.0127 g, 30 μmol) and DIPEA (0.0230 g, 178 μmol), can be mixed for 2 h in a 2:2:1 dimethylformamide:dioxane: water solution (250 μL). Coenzyme B12-ethylenediamine conjugate 2 (0.0039 g, 2.3 μmol) can be added and the reaction can be mixed for 18 h. The desired compound can be purified by HPLC (semiprepative C-18 column) using a linear gradient binary solvent system (solvent A: 0.1% TFA/H2O; solvent B: 0.1% TFA/CH3CN) with a ratio of A:B that can vary from 97:3 (0 min) to 10:90 (40 min). Removal of solvent by lyophilization is expected to afford a red solid which can be characterized by ESI MS.

Synthesis and Characterization of Coenzyme $B_{12}$ Fluorophore Conjugates AdoCbl2, AdoCbl-3, and AdoCbl4

General synthesis of cobalamin-fluorophore conjugates: The N-hydroxysuccinimide ester of a fluorophore (1 eq.), coenzyme B12-ethylenediamine conjugate 2 (1.5 eq.), and diisopropylethylamine (6 eq.) can be mixed in dimethylformamide for 18 hrs. The desired compound can be purified by HPLC (semiprepative C-18 column) using a linear gradient binary solvent system (solvent A: 0.1% TFA/H2O; solvent B: 0.1% TFA/CH3CN) with a ratio of A:B that varied from 97:3 (0 min) to 10:90 (40 min), Removal of solvent by lyophilization is expected to afford a solid.

Coenzyme B12-SulfoCy5 Conjugate (AdoCbl-2): can be characterized by ESI MS.

Coenzyme B12-Atto725 Conjugate: blue solid (AdoCbl-3), can be characterized by ESI MS.

Coenzyme B12-Dylight800 Conjugate (AdoCbl-4): can be characterized by ESI MS.

SELECTED REFERENCES

1. Lee K Y, Mooney D J, "Hydrogels for tissue engineering," Chem Rev 101:1869-1879 (2001).
2. DeForest C A, Anseth K S, "Advances in bioactive hydrogels to probe and direct cell fate," Annu Rev Chem Biomol Eng, 3:421-444 (2012).
3. Langer R, Tirrell D A, "Designing materials for biology and medicine," Nature, 428:487-492 (2004).
4. Burdick J A, Murphy W L, "Moving from static to dynamic complexity in hydrogel design," Nat Commun, 3:1269 (2012).
5. DeForest C A, Anseth K S, "Cytocompatible click-based hydrogels with dynamically tunable properties through orthogonal photoconjugation and photocleavage reactions," Nat Chem, 3:925-931 (2011).
6. Tomatsu I, Peng K, Kros A, "Photoresponsive hydrogels for biomedical applications," Adv Drug Deliv Rev, 63:1257-1266 (2011).
7. Katz J S, Burdick J A, "Light-responsive biomaterials: Development and applications," Macromol Biosci, 10:339-348 (2010).
8. Yagai S, Kitamura A, "Recent advances in photoresponsive supramolecular self-assemblies," Chem Soc Rev, 37:1520-1529 (2008).
9. Deisseroth K, "Optogenetics," Nat Methods, 8:26-29 (2011).
10. Ercole F, Davis T P, Evans R A, "Photo-responsive systems and biomaterials: Photochromic polymers, light-triggered self-assembly, surface modification, fluorescence modulation and beyond," Polyp¡ Chem, 1:37-54 (2010).
11. Fairbanks B D, Scott T F, Kloxin C J, Anseth K S, Bowman C N, "Thiol-Yne photopolymerizations: Novel mechanism, kinetics, and step-growth formation of highly cross-linked networks," Macromolecules, 42:211-217 (2009).
12. DeForest C A, Polizzotti B D, Anseth K S, "Sequential click reactions for synthesizing and patterning three-dimensional cell microenvironments," Nat Mater, 8:659-664 (2009).
13. DeForest C A, Tirrell D A, "A photoreversible protein-patterning approach for guiding stem cell fate in three-dimensional gels," Nat Mater, 14:523-531 (2015).
14. Alvarez-Lorenzo C, Bromberg L, Concheiro A, "Light-sensitive intelligent drug delivery systems," Photochem Photohiol, 85:848-860 (2009).
15. Fairbanks B D, et al., "A versatile synthetic extracellular matrix mimic via thiol-norbornene photopolymerization," Adv Mater, 21:5005-5010 (2009).
16. Sun F, Zhang W B, Mandavi A, Arnold F H, Tirrell D A, "Synthesis of bioactive protein hydrogels by genetically encoded SpyTag-SpyCatcher chemistry," Proc Natl Acad Sci USA, 111:11269-11274 (2014).
17. Banta S, Wheeldon I R, Blenner M, "Protein engineering in the development of functional hydrogels," Annu Rev Biomed Eng, 12:167-186 (2010).
18. Gao X, Fang J, Xue B, Fu L, Li H, "Engineering protein hydrogels using SpyCatcher-SpyTag chemistry," Biomacromolecules, 17:2812-2819 (2016).
19. Fang J, et al., "Forced protein unfolding leads to highly elastic and tough protein hydrogels," Nat Commun, 4:2974 (2013).
20. Murphy W L, Dillmore W S, Modica J, Mrksich M, "Dynamic hydrogels: Translating a protein conformational change into macroscopic motion," Angew Chem Int Ed Engl, 46:3066-3069 (2007).
21. Sui Z J, King W J, Murphy W L, "Protein-based hydrogels with tunable dynamic responses," Adv Funct Mater, 18:1824-1831 (2008).
22. Kutta R J, et al., "The photochemical mechanism of a B12-dependent photoreceptor protein," Nat Commun, 6:7907 (2015).
23. Jost M, et al., "Structural basis for gene regulation by a B12-dependent photoreceptor," Nature, 526:536-541 (2015).
24. Ortiz-Guerrero J M, Polanco M C, Murillo F J, Padmanabhan S, Elias-Amanz M, "Light-dependent gene regulation by a coenzyme B12-based photoreceptor," Proc Natl Acad Sci USA, 108:7565-7570 (2011).
25. Jost M, Simpson Drennan C, "The transcription factor CarH safeguards use of adenosylcobalamin as a light sensor by altering the photolysis products," Biochemistry, 54:3231-3234 (2015).
26. Zakeri B, et al, "Peptide tag forming a rapid covalent bond to a protein, through engineering a bacterial adhesion," Proc Natl Acad Sci USA, 109:E690-E697 (2012).
27. Schoene C, Fierer J O, Bennett S P, Howarth M, "SpyTag/SpyCatcher cyclization confers resilience to boiling on a mesophilic enzyme," Angew Chem Int Ed Engl, 53:6101-6104 (2014).
28. Veggiani G, et al., "Programmable polyproteams built using twin peptide superglues," Proc Natl Acad Sci USA, 113:1202-1207 (2016).
29. Reddington S C, Howarth M, "Secrets of a covalent interaction for biomaterials and biotechnology: SpyTag and SpyCatcher," Curr Opin Chern Biol, 29:94-99 (2015).
30. Chen A Y, et al., "Synthesis and patterning of tunable multiscale materials with engineered cells," Nat Mater, 13:515-523 (2014).
31. Botvanszki Z, Tay P K R, Nguyen P Q, Nussbaumer M G, Joshi N S, "Engineered catalytic biofilms: Site-specific enzyme immobilization onto E. coli curli nanofibers," Biotechnol Bioeng, 112:2016-2024 (2015).
32. Zhang W B, Sun F, Tirrell D A, Arnold F H, "Controlling macromolecular topology with genetically encoded Spy-Tag-SpyCatcher chemistry," J Am Chem Soc, 135:13988-13997 (2013).
33. Matsunaga R, Yanaka S, Nagatoishi S, Tsumoto K, "Hyperthin nanochains composed of self-polymerizing protein shackles," Nat Comrnun, 4:2211 (2013).
34. Fairhead M, et al., "SpyAvidin hubs enable precise and ultrastable orthogonal nanoassembly," J Am Chem Soc, 136:12355-12363 (2014).
35. Liu Z D, et al., "A novel method for synthetic vaccine construction based on protein assembly," Sci Rep UK, 4:7266 (2014).
36. Bedbrook C N, et al., "Genetically encoded spy peptide fusion system to detect plasma membrane-localized proteins in vivo," Chem Biol, 22:1108-1121 (2015).
37. Urry D W, "Physical chemistry of biological free energy transduction as demonstrated by elastic protein-based polymers, "J Phys Chem B 101:11007-11028 (1997).
38. Santoro M, Tatara A M, Mikos A G, "Gelatin carriers for drug and cell delivery in tissue engineering," J Control Release, 190:210-218 (2014).

39. Vo T N, Kasper F K, Mikos A G, "Strategies for controlled delivery of growth factors and cells for bone regeneration," Adv Drug Deliv Rev, 64:1292-1309 (2012).
40. Sension R J, Harris D A, Cole A G, "Time-resolved spectroscopic studies of B12 coenzymes: Comparison of the influence of solvent on the primary photolysis mechanism and geminate recombination of methyl-, ethyl-, n-propyl-, and 5'-deoxyadenosylcobalamin," J Phys Chem B, 109:21954-21962 (2005).
41. Seetulsingh-Goorah S P, "Mechanisms of adenosine-induced cytotoxicity and their clinical and physiological implications," Biofactors, 27:213-230 (2006).
42. Tessmar J K, Göpferich A M, "Matrices and scaffolds for protein delivery in tissue engineering," Adv Drug Deliv Rev, 59:274-291 (2007).
43. Shah N J, et al., "Adaptive growth factor delivery from a polyelectrolyte coating promotes synergistic bone tissue repair and reconstruction," Prot Natl Acad Sci USA, 111:12847-12852 (2014).
44. Hu. J, Wang G, Liu X, Gao W, "Enhancing pharmacokinetics, tumor accumulation, and antitumor efficacy by elastin-like polypeptide fusion of interferon alpha," Adv Mater, 27:7320-7324 (2015).
45. Kloxin, A M, et al., "Photodegradable hydrogels for dynamic tuning of physical and chemical properties," Science, 324 (5923): 59-69 (2009).
46. Luo, Y and Shoichet M S, "A photolabile hydrogel for guided three-dimensional cell growth and migration," Nature Materials, 3(4):249-253 (2004).
47. Wirkner, M et al., "Triggered cell release from materials using bioadhesive photocleavable linkers," Advanced Materials, 23(34):3907-3910 (2011).
48. Zhou, H and Hockin H K Xu, "The fast release of stem cells from alginate-fibrin microbeads in injectable scaffolds for bone tissue engineering," Biomaterials, 32(30): 7503-7513 (2011).
49. Leslie, S K et al., "Controlled release of rat adipose-derived stem cells from alginate microbeads," Biomaterials, 34(33):8172-8184 (2017).
50. Mak, W C et al., "Thermo-theological responsive microcapsules for time-dependent controlled release of human mesenchymal stromal cells: Biomaterials Science, 5(11): 1269-1277 (2015).
51. Huebsch, N et al., "Matrix elasticity of void-forming hydrogels controls transplanted-stem-cell mediated bone formation," Nature Materials, 14(12):1269-1277 (2015).
52. Shell, T. et al. "Tunable Visible and Near-IR Photoactivation of Light-Responsive Compounds by Using Fluorophores as Light-Capturing Antennas", Angew, Chemie Int. Ed. English, 53: 875-878 (2013).

Patents, patent applications, publications, scientific articles, books, web sites, other documents and materials, and products referenced or mentioned herein are indicative of the levels of skill of those skilled in the art to which the inventions pertain. Each such referenced document, material and product is hereby incorporated by reference herein to the same extent as if it had been incorporated by reference in its entirety individually or set forth or reprinted herein in its entirety. Additionally, all claims in this application, and all priority applications (if any), including but not limited to original claims, are hereby incorporated in their entirety into, and form a part of, the written description of the invention. Applicant reserves the right to physically incorporate into this specification any and all materials and information from any such patents, applications, publications, scientific articles, web sites, electronically available information, and other referenced materials or documents. Applicant reserves the right to physically incorporate into any part of this document, including any part of the written description, and the claims referred to above, including, but not limited to, any original claims.

The inventions have been described broadly and generically herein. Each of the narrower species and subgeneric groupings falling within the generic disclosure also form part of these inventions. This includes the generic description of each invention which hereby include, including any claims thereto, a proviso or negative limitation removing, or optionally allowing the removal of, any subject matter from the genus, regardless of whether or not the excised materials, or options, were specifically recited or identified in haec verba herein, and all such variations form a part of the original written description of the inventions. In addition, where features, or aspects, of an invention are described in terms of a Markush group, the invention shall be understood thereby to be described in terms of each and every, and any, individual member or subgroup of members of the Markush group.

The inventions illustratively described and claimed herein can suitably be practiced in the absence of any element or elements, limitation or limitations, not specifically disclosed herein, or described herein, as essential. Thus, for example, the terms "comprising," "including," "containing," "for example," etc., shall be read expansively and without limitation. The term "including" means "including but not limited to." The phrase "for example" was not limited to, or by, the items that follow the phrase.

In claiming their inventions, the inventors reserve the right to substitute any transitional phrase with any other transitional phrase, and the inventions shall be understood to include such substituted transitions and form part of the original written description of the inventions. Thus, for example, the term "comprising" may be replaced with either of the transitional phrases "consisting essentially of" or "consisting of."

The methods and processes illustratively described herein may be suitably practiced in differing orders of steps. They are not necessarily restricted to the orders of steps indicated herein, or in the claims.

The terms and expressions employed herein have been used as terms of description and not of limitation, and there was no intention in the use of such terms and expressions, or any portions thereof, to exclude any equivalents now know or later developed, whether or not such equivalents are set forth or shown or described herein or whether or not such equivalents are viewed as predictable, but it was recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary of, and not intended as limitations on, the scope of the invention. Other objects, aspects, and embodiments will occur to those skilled in the art upon consideration of this specification, and are encompassed within the spirit of the invention as defined by the scope of the claims. Where examples are given, the description shall be construed to include, but not to be limited to, only those examples, it will be readily apparent to one skilled in the art that varying substitutions and modifications may be made to the invention disclosed herein, without departing from the scope and spirit of the invention, and from the description of the inventions, including those illustratively set forth herein, it was manifest that various modifications and equivalents can be used to implement the concepts of the present invention, without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

While this invention has been disclosed with reference to specific embodiments, it was apparent that other embodiments and variations of this invention can be devised by those skilled in the art, without departing from the true spirit and scope of the invention. The appended claims include all such embodiments and equivalent variations.

What is claimed is:

1. A light-responsive hydrogel biopolymer matrix comprising:
   (a) one or a plurality of light-responsive gelation initiator complexes comprising the protein photoreceptor $CarH_c$ and the multi-dentate ligand adenosylcobalamin, connected to one or a plurality of a first extracellular matrix protein fragments, and
   (b) two or more cross-linkable proteins connected to one or a plurality of a second extracellular matrix protein fragments,
   wherein the first extracellular matrix protein fragments and second extracellular matrix protein fragments are independently selected from elastin fragments which comprise a repeating polypeptide having the sequence of $(VPGXG)_n$ (SEQ ID NO: 23), wherein X represents valine or glutamate, the ratio of valine to glutamate ranges from 10:1 to 1:10, n is an integer selected from 2 to 25, the two or more cross-linkable proteins are SpyTag and SpyCatcher, and
   the matrix is responsive to light comprising a wavelength from about 300 nm to about 600 nm.

2. The light-responsive hydrogel biopolymer matrix of claim 1,
   wherein upon exposure to light with a wavelength from about 300 nm to about 600 nm, the matrix exhibits a phase transition from gel to solution.

3. The light-responsive hydrogel biopolymer matrix of claim 1 further comprising a mammalian cell.

4. The light-responsive hydrogel biopolymer matrix of claim 3, wherein the mammalian cell is a fibroblast or a stem cell.

5. The light-responsive hydrogel biopolymer matrix of claim 4, wherein the stem cell is a mesenchymal stem cell (hMSC).

6. The light-responsive hydrogel biopolymer matrix of claim 1 further comprising a non-covalently bound protein selected from a therapeutic protein, cytokine, or fluorescent protein.

7. The light-responsive hydrogel biopolymer matrix of claim 6, wherein the fluorescent protein is mCherry.

8. The light-responsive hydrogel biopolymer matrix of claim 1, further comprising water.

9. The light-responsive hydrogel biopolymer matrix of claim 8, wherein the water content of the hydrogel is in the range from 70% to 99.5% (w/w).

10. The light-responsive hydrogel biopolymer matrix of claim 1, wherein the protein photoreceptor content of the hydrogel is in the range from 0.001% to 0.5% (w/w).

11. A light-responsive hydrogel biopolymer matrix comprising:
    a first telechelic biopolymer which comprises a first light-responsive gelation initiator complex covalently bound to the first extracellular matrix protein fragments which are covalently bound to a first two or more cross-linkable proteins, and
    a second telechelic biopolymer which comprises a second light-responsive gelation initiator complex covalently bound to the second extracellular matrix protein fragments which are covalently bound to a second two or more cross-linkable proteins.

12. The light-responsive hydrogel biopolymer matrix of claim 11,
    wherein said first telechelic biopolymer is a recombinant protein encoding for the first light-responsive gelation initiator complex covalently bound to the first extracellular matrix protein fragments which are covalently bound to a first two or more cross-linkable proteins, and said second telechelic biopolymer is a recombinant protein encoding for the second light-responsive gelation initiator complex covalently bound to the second extracellular matrix protein fragments which are covalently bound to a second two or more cross-linkable proteins.

13. The light-responsive hydrogel biopolymer matrix of claim 12,
    wherein the first telechelic biopolymer and second telechelic biopolymer independently have the linkage structure selected from: SpyTag-$CarH_c$-SpyTag, SpyCatcher-$CarH_c$-SpyCatcher, SpyTag-$CarH_c$-SpyCatcher, SpyTag-$CarH_c$, SpyCatcher-$CarH_c$, and $CarH_c$-CL7.

14. The light-responsive hydrogel biopolymer matrix of claim 12, wherein the first telechelic biopolymer and second telechelic biopolymer independently have the linkage structure selected from: SpyTag-elastin-$CarH_c$-elastin-SpyTag, SpyCatcher-elastin-$CarH_c$-elastin-SpyCatcher, SpyTag-elastin-$CarH_c$-elastin-SpyCatcher, SpyTag-elastin-$CarH_c$, SpyCatcher-elastin-$CarH_c$, and $CarH_c$-elastin-CL7,
    wherein the elastin segments comprise a repeating polypeptide having the sequence of $(VPGXG)_n$ (SEQ ID NO: 23), wherein X represents valine or glutamate, the ratio of valine to glutamate ranges from 10:1 to 1:10, and n is an integer selected from 2 to 25.

15. A polypeptide corresponding to the linkage structure of claim 13, comprising the sequence of SEQ ID NO:2.

16. An oligonucleotide encoding the linkage structure of claim 14, comprising the sequence of SEQ ID NO:1.

17. A method for producing a light-responsive hydrogel biopolymer matrix, the method comprising dissolving one or a plurality of light-responsive gelation initiator complexes comprising the protein photoreceptor $CarH_c$ and the multi-dentate ligand adenosylcobalamin connected to one or a plurality of a first extracellular matrix protein fragments and two or more cross-linkable proteins connected to one or a plurality of a second extracellular matrix protein fragments in an aqueous solution to form a gelation mixture under light which does not comprise a wavelength of less than about 600 nm,
- wherein the first extracellular matrix protein fragments and second extracellular matrix protein fragments are independently selected from elastin fragments which comprise a repeating polypeptide having the sequence of $(VPGXG)_n$ (SEQ ID NO: 23), wherein X represents valine or glutamate, the ratio of valine to glutamate ranges from 10:1 to 1:10, n is an integer selected from 2 to 25, and
- the two or more cross-linkable proteins are SpyTag and SpyCatcher.

18. A method of culturing cells in a photoresponsive hydrogel matrix, the method comprising the steps of:
- (a) dissolving one or more cells in an aqueous solution,
- (b) dissolving one or a plurality of light-responsive gelation initiator complexes comprising the protein photoreceptor $CarH_c$ and the multi-dentate ligand adenosylcobalamin connected to one or a plurality of a first extracellular matrix protein fragments and two or more cross-linkable proteins connected to one or a plurality of a second extracellular matrix protein fragments in an aqueous solution comprising one or more cells to form a gelation mixture under light which does not comprise a wavelength of less than about 600 nm,
- wherein the first extracellular matrix protein fragments and second extracellular matrix protein fragments are independently selected from elastin fragments which comprise a repeating polypeptide having the sequence of $(VPGXG)_n$ (SEQ ID NO: 24), wherein X represents valine or glutamate, the ratio of valine to glutamate ranges from 10:1 to 1:10, n is an integer selected from 5 to 25, and
- the two or more cross-linkable proteins are SpyTag and SpyCatcher.

19. The method of claim 18, further comprising the steps of:
- (c) contacting the gelation mixture with cell growth media to form a gelation growth media, and
- (d) incubating the gelation growth media to form incubated gelation growth media.

20. The method of claim 19, further comprising the step of:
- (e) irradiating the incubated gelation growth media with light comprising a wavelength between about 300 nm and about 600 nm to transform the hydrogel into a liquid resulting in release of the cells from the gelation mixture.

* * * * *

SEQUENCE LISTING

<160> NUMBER OF SEQ ID NOS: 25

<210> SEQ ID NO 1
<211> LENGTH: 1989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | | |
|---|---|---|---|---|---|---|
| atgaaaggca | gcagccatca | tcatcatcat | cacgtcgaca | tcccaacgac | cgaaaacctg | 60 |
| tattttcagg | gcgccatggt | tgataccta | tcaggtttat | caagtgagca | aggtcagtcc | 120 |
| ggtgatatga | caattgaaga | agatagtgct | acccatatta | aattctcaaa | acgtgatgag | 180 |
| gacggcaaag | agttagctgg | tgcaactatg | gagttgcgtg | attcatctgg | taaaactatt | 240 |
| agtacatgga | tttcagatgg | acaagtgaaa | gatttctacc | tgtatccagg | aaaatataca | 300 |
| tttgtcgaaa | ccgcagcacc | agacggttat | gaggtagcaa | ctgctattac | ctttacagtt | 360 |
| aatgagcaag | gtcaggttac | tgtaaatggc | aaagcaacta | aaggtgacgc | tcatattgac | 420 |
| ggtccgcaag | gtatttgggg | tcagctcgag | ggccacggcg | tgggtgttcc | gggcgtcggt | 480 |
| gtgccgggtg | tgggtgtgcc | gggcgaaggt | gtgccgggcg | tcggtgtgcc | gggtgttggt | 540 |
| gttccgggcg | ttggtgtgcc | gggcgttggc | gtgccgggcg | agggtgtgcc | gggcgttggt | 600 |
| gttccgggcg | tgggtgtgcc | gggcgtgggc | gtgccgggcg | tcggtgttcc | gggcgagggt | 660 |
| gtgccgggcg | taggtgtgcc | gggcgttggt | gagctcccag | aagatctggg | caccggcctg | 720 |
| ctggaagcac | tgctgcgcgg | tgatctggcg | ggcgccgaag | ctctgtttcg | tcgtggcctg | 780 |
| cgtttctggg | gcccggaagg | cgttctggag | cacctgctgc | tgccggtgct | gcgtgaagtg | 840 |
| ggcgaagctt | ggcaccgtgg | tgaaatcggc | gttgcagaag | aacacctggc | gagcaccttc | 900 |
| ctgcgcgcgc | gtctgcagga | gctgctggac | ctggcaggtt | tcccgccggg | tccgccggtc | 960 |
| ctggtgacta | cgccgccggg | cgaacgccac | gaaatcggtc | gatgctggc | ggcgtaccat | 1020 |
| ctgcgtcgta | agggcgtccc | ggcgctgtat | ctgggcccgg | atactccgct | gccggacctg | 1080 |
| cgtgcactgg | cgccgcct | gggtgcaggc | gcggtcgtgc | tgtctgctgt | tctgagcgaa | 1140 |
| ccgctgcgt | ctctgcctga | cggtgccctg | aaagatctgg | caccgcgtgt | tttcctgggc | 1200 |
| ggccagggcg | caggcccgga | agaggcacgc | cgtctgggtg | ccgaatacat | ggaagacctg | 1260 |
| aaaggcctgc | tgaagcgct | gtggctgccg | cgcggtccgg | aaaaagaagc | aatcactagt | 1320 |
| gtgccgggcg | tcggcgtgcc | gggcgtaggt | gttccgggcg | agggtgttcc | gggcgttggt | 1380 |
| gtgccgggcg | tcggcgtgcc | gggcgtgggt | gttccgggcg | taggtgtgcc | gggcgagggt | 1440 |
| gtgccgggcg | tgggcgtgcc | gggcgtaggt | gttccgggcg | taggtgttcc | gggcgtaggt | 1500 |
| gttccgggtg | aaggcgtgcc | gggcgttggt | gtgccgggtg | tgggcgtgcc | gggcgggctg | 1560 |

-continued

```
gtcgacatcc caacgaccga aaacctgtat tttcagggcg ccatggttga taccttatca  1620
ggtttatcaa gtgagcaagg tcagtccggt gatatgacaa ttgaagaaga tagtgctacc  1680
catattaaat tctcaaaacg tgatgaggac ggcaaagagt tagctggtgc aactatggag  1740
ttgcgtgatt catctggtaa aactattagt acatggattt cagatggaca agtgaaagat  1800
ttctacctgt atccaggaaa atatacattt gtcgaaaccg cagcaccaga cggttatgag  1860
gtagcaactg ctattacctt tacagttaat gagcaaggtc aggttactgt aaatggcaaa  1920
gcaactaaag gtgacgctca tattgacggt ccgcaaggta tttggggtca gctcgagtgg  1980
aagaaataa                                                           1989
```

<210> SEQ ID NO 2
<211> LENGTH: 662
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Gly Ser Ser His His His His His His Val Asp Ile Pro Thr
1               5                   10                  15

Thr Glu Asn Leu Tyr Phe Gln Gly Ala Met Val Asp Thr Leu Ser Gly
            20                  25                  30

Leu Ser Ser Glu Gln Gly Gln Ser Gly Asp Met Thr Ile Glu Glu Asp
        35                  40                  45

Ser Ala Thr His Ile Lys Phe Ser Lys Arg Asp Glu Asp Gly Lys Glu
    50                  55                  60

Leu Ala Gly Ala Thr Met Glu Leu Arg Asp Ser Ser Gly Lys Thr Ile
65                  70                  75                  80

Ser Thr Trp Ile Ser Asp Gly Gln Val Lys Asp Phe Tyr Leu Tyr Pro
                85                  90                  95

Gly Lys Tyr Thr Phe Val Glu Thr Ala Ala Pro Asp Gly Tyr Glu Val
            100                 105                 110

Ala Thr Ala Ile Thr Phe Thr Val Asn Glu Gln Gly Gln Val Thr Val
        115                 120                 125

Asn Gly Lys Ala Thr Lys Gly Asp Ala His Ile Asp Gly Pro Gln Gly
    130                 135                 140

Ile Trp Gly Gln Leu Glu Gly His Gly Val Gly Val Pro Gly Val Gly
145                 150                 155                 160

Val Pro Gly Val Gly Val Pro Gly Glu Gly Val Pro Gly Val Gly Val
                165                 170                 175

Pro Gly Val Gly Val Pro Gly Val Gly Val Pro Gly Val Gly Val Pro
            180                 185                 190

Gly Glu Gly Val Pro Gly Val Gly Val Pro Gly Val Gly Val Pro Gly
        195                 200                 205

Val Gly Val Pro Gly Val Gly Val Pro Gly Glu Gly Val Pro Gly Val
    210                 215                 220

Gly Val Pro Gly Val Gly Glu Leu Pro Glu Asp Leu Gly Thr Gly Leu
225                 230                 235                 240

Leu Glu Ala Leu Leu Arg Gly Asp Leu Ala Gly Glu Ala Leu Phe
                245                 250                 255

Arg Arg Gly Leu Arg Phe Trp Gly Pro Glu Gly Val Leu Glu His Leu
            260                 265                 270

Leu Leu Pro Val Leu Arg Glu Val Gly Glu Ala Trp His Arg Gly Glu

```
                      275                 280                 285
    Ile Gly Val Ala Glu Glu His Leu Ala Ser Thr Phe Leu Arg Ala Arg
    290                 295                 300

Leu Gln Glu Leu Leu Asp Leu Ala Gly Phe Pro Pro Gly Pro Pro Val
305                 310                 315                 320

Leu Val Thr Thr Pro Pro Gly Glu Arg His Glu Ile Gly Ala Met Leu
                    325                 330                 335

Ala Ala Tyr His Leu Arg Arg Lys Gly Val Pro Ala Leu Tyr Leu Gly
                    340                 345                 350

Pro Asp Thr Pro Leu Pro Asp Leu Arg Ala Leu Ala Arg Arg Leu Gly
                355                 360                 365

Ala Gly Ala Val Val Leu Ser Ala Val Leu Ser Glu Pro Leu Arg Ala
                370                 375                 380

Leu Pro Asp Gly Ala Leu Lys Asp Leu Ala Pro Arg Val Phe Leu Gly
385                 390                 395                 400

Gly Gln Gly Ala Gly Pro Glu Glu Ala Arg Arg Leu Gly Ala Glu Tyr
                    405                 410                 415

Met Glu Asp Leu Lys Gly Leu Ala Glu Ala Leu Trp Leu Pro Arg Gly
                    420                 425                 430

Pro Glu Lys Glu Ala Ile Thr Ser Val Pro Gly Val Gly Val Pro Gly
                435                 440                 445

Val Gly Val Pro Gly Glu Gly Val Pro Gly Val Gly Val Pro Gly Val
    450                 455                 460

Gly Val Pro Gly Val Gly Val Pro Gly Val Gly Val Pro Gly Glu Gly
465                 470                 475                 480

Val Pro Gly Val Gly Val Pro Gly Val Gly Val Pro Gly Val Gly Val
                    485                 490                 495

Pro Gly Val Gly Val Pro Gly Glu Gly Val Pro Gly Val Gly Val Pro
                500                 505                 510

Gly Val Gly Val Pro Gly Gly Leu Val Asp Ile Pro Thr Thr Glu Asn
                515                 520                 525

Leu Tyr Phe Gln Gly Ala Met Val Asp Thr Leu Ser Gly Leu Ser Ser
    530                 535                 540

Glu Gln Gly Gln Ser Gly Asp Met Thr Ile Glu Asp Ser Ala Thr
545                 550                 555                 560

His Ile Lys Phe Ser Lys Arg Asp Glu Asp Gly Lys Glu Leu Ala Gly
                    565                 570                 575

Ala Thr Met Glu Leu Arg Asp Ser Ser Gly Lys Thr Ile Ser Thr Trp
                    580                 585                 590

Ile Ser Asp Gly Gln Val Lys Asp Phe Tyr Leu Tyr Pro Gly Lys Tyr
                    595                 600                 605

Thr Phe Val Glu Thr Ala Ala Pro Asp Gly Tyr Glu Val Ala Thr Ala
                610                 615                 620

Ile Thr Phe Thr Val Asn Glu Gln Gly Gln Val Thr Val Asn Gly Lys
    625                 630                 635                 640

Ala Thr Lys Gly Asp Ala His Ile Asp Gly Pro Gln Gly Ile Trp Gly
                    645                 650                 655

Gln Leu Glu Trp Lys Lys
                660

<210> SEQ ID NO 3
<211> LENGTH: 1257
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 3

```
atgaaaggca gcagccatca tcatcatcat cacgtcgacg cccatattgt catggttgat      60
gcatacaagc cgacgaagct cgacggccac ggcgtgggtg ttccgggcgt cggtgtgccg     120
ggtgtgggtg tgccgggcga aggtgtgccg ggcgtcggtg tgccgggtgt tggtgttccg     180
ggcgttggtg tgccgggcgt tggcgtgccg ggcgagggtg tgccgggcgt tggtgttccg     240
ggcgtgggtg tgccgggcgt gggcgtgccg ggcgtcggtg ttccgggcga gggtgtgccg     300
ggcgtaggtg tgccgggcgt tggtgagctc ccagaagatc tgggcaccgg cctgctggaa     360
gcactgctgc gcggtgatct ggcgggcgcc gaagctctgt tcgtcgtgg cctgcgtttc      420
tggggcccgg aaggcgttct ggagcacctg ctgctgccgg tgctgcgtga agtgggcgaa     480
gcttggcacc gtggtgaaat cggcgttgca gaagaacacc tggcgagcac cttcctgcgc     540
gcgcgtctgc aggagctgct ggacctgca ggtttcccgc cgggtccgcc ggtcctggtg      600
actacgccgc cgggcgaacg ccacgaaatc ggtgcgatgc tggcggcgta ccatctgcgt     660
cgtaagggcg tcccgcgct gtatctgggc ccggatactc cgctgccgga cctgcgtgca     720
ctggcgcgcc gcctgggtgc aggcgcggtc gtgctgtctg ctgttctgag cgaaccgctg     780
cgtgctctgc ctgacggtgc cctgaaagat ctggcaccgc gtgttttcct gggcggccag     840
ggcgcaggcc cggaagaggc acgccgtctg ggtgccgaat acatggaaga cctgaaaggc     900
ctggctgaag cgctgtggct gccgcgcggt ccggaaaaag aagcaatcac tagtgtgccg     960
ggcgtcggcg tgccgggcgt aggtgttccg ggcgagggtg ttccgggcgt tggtgtgccg    1020
ggcgtcggcg tgccgggcgt gggtgttccg ggcgtaggtg tgccgggcga gggtgtgccg    1080
ggcgtgggcg tgccgggcgt aggtgttccg ggcgtaggtg ttccgggcgt aggtgttccg    1140
ggtgaaggcg tgccgggcgt tggtgtgccg ggtgtgggcg tgccgggcgg gctgctcgac    1200
gcccatattg tcatggttga tgcatacaag ccgacgaagc tcgagtggaa gaaataa       1257
```

<210> SEQ ID NO 4
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Lys Gly Ser Ser His His His His His Val Asp Ala His Ile
1               5                   10                  15

Val Met Val Asp Ala Tyr Lys Pro Thr Lys Leu Asp Gly His Gly Val
                20                  25                  30

Gly Val Pro Gly Val Gly Val Pro Gly Val Gly Val Pro Gly Glu Gly
            35                  40                  45

Val Pro Gly Val Gly Val Pro Gly Val Gly Val Pro Gly Val Gly Val
        50                  55                  60

Pro Gly Val Gly Val Pro Gly Glu Gly Val Pro Gly Val Gly Val Pro
65                  70                  75                  80

Gly Val Gly Val Pro Gly Val Gly Val Pro Gly Val Gly Val Pro Gly
                85                  90                  95

Glu Gly Val Pro Gly Val Gly Val Pro Gly Val Gly Glu Leu Pro Glu
            100                 105                 110
```

Asp Leu Gly Thr Gly Leu Leu Glu Ala Leu Leu Arg Gly Asp Leu Ala
            115                 120                 125

Gly Ala Glu Ala Leu Phe Arg Arg Gly Leu Arg Phe Trp Gly Pro Glu
        130                 135                 140

Gly Val Leu Glu His Leu Leu Pro Val Leu Arg Glu Val Gly Glu
145                 150                 155                 160

Ala Trp His Arg Gly Glu Ile Gly Val Ala Glu His Leu Ala Ser
                165                 170                 175

Thr Phe Leu Arg Ala Arg Leu Gln Glu Leu Leu Asp Leu Ala Gly Phe
            180                 185                 190

Pro Pro Gly Pro Pro Val Leu Val Thr Thr Pro Gly Glu Arg His
        195                 200                 205

Glu Ile Gly Ala Met Leu Ala Ala Tyr His Leu Arg Arg Lys Gly Val
    210                 215                 220

Pro Ala Leu Tyr Leu Gly Pro Asp Thr Pro Leu Pro Asp Leu Arg Ala
225                 230                 235                 240

Leu Ala Arg Arg Leu Gly Ala Gly Ala Val Val Ser Ala Val Leu
                245                 250                 255

Ser Glu Pro Leu Arg Ala Leu Pro Asp Gly Ala Leu Lys Asp Leu Ala
            260                 265                 270

Pro Arg Val Phe Leu Gly Gly Gln Gly Ala Gly Pro Glu Glu Ala Arg
        275                 280                 285

Arg Leu Gly Ala Glu Tyr Met Glu Asp Leu Lys Gly Leu Ala Glu Ala
    290                 295                 300

Leu Trp Leu Pro Arg Gly Pro Glu Lys Glu Ala Ile Thr Ser Val Pro
305                 310                 315                 320

Gly Val Gly Val Pro Gly Val Gly Val Pro Gly Glu Gly Val Pro Gly
                325                 330                 335

Val Gly Val Pro Gly Val Gly Val Pro Gly Val Gly Val Pro Gly Val
            340                 345                 350

Gly Val Pro Gly Glu Gly Val Pro Gly Val Gly Val Pro Gly Val Gly
        355                 360                 365

Val Pro Gly Val Gly Val Pro Gly Val Gly Val Pro Gly Glu Gly Val
    370                 375                 380

Pro Gly Val Gly Val Pro Gly Val Gly Val Pro Gly Gly Leu Leu Asp
385                 390                 395                 400

Ala His Ile Val Met Val Asp Ala Tyr Lys Pro Thr Lys Leu Glu Trp
                405                 410                 415

Lys Lys

<210> SEQ ID NO 5
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgatggtga gcaagggcga ggaggataac atggccatca tcaaggagtt catgcgcttc      60
aaggtgcaca tggagggctc cgtgaacggc cacgagttcg agatcgaggg cgagggcgag     120
ggccgcccct acgagggcac ccagaccgcc aagctgaagg tgaccaaggg tggcccctg     180 cccttcgcct gggacatcct gtcccctcag ttcatgtacg gctccaaggc ctacgtgaag     240

```
caccccgccg acatccccga ctacttgaag ctgtccttcc ccgagggctt caagtgggag      300
cgcgtgatga acttcgagga cggcggcgtg gtgaccgtga cccaggactc ctccctgcag      360
gacggcgagt tcatctacaa ggtgaagctg cgcggcacca acttcccctc cgacggcccc      420
gtaatgcaga agaagaccat gggctgggag gcctcctccg agcggatgta ccccgaggac      480
ggcgccctga agggcgagat caagcagagg ctgaagctga aggacggcgg ccactacgac      540
gctgaggtca agaccaccta caaggccaag aagcccgtgc agctgcccgg cgcctacaac      600
gtcaacatca gttggacat cacctcccac aacgaggact acaccatcgt ggaacagtac       660
gaacgcgccg agggccgcca ctccaccggc ggcatggacg agctgtacaa ggagctccca      720
gaagatctgg gcaccggcct gctggaagca ctgctgcgcg tgatctggc gggcgccgaa       780
gctctgtttc gtcgtggcct gcgtttctgg ggcccggaag cgttctgga gcacctgctg       840
ctgccggtgc tgcgtgaagt gggcgaagct tggcaccgtg gtgaaatcgg cgttgcagaa      900
gaacacctgg cgagcacctt cctgcgcgcg cgtctgcagg agctgctgga cctggcaggt      960
ttcccgccgg tccgccggt cctggtgact acgccgccgg cgaacgcca cgaaatcggt       1020
gcgatgctgg cggcgtacca tctgcgtcgt aagggcgtcc cggcgctgta tctgggcccg     1080
gatactccgc tgccggacct gcgtgcactg gcgcgccgcc tgggtgcagg cgcggtcgtg     1140
ctgtctgctg ttctgagcga accgctgcgt gctctgcctg acggtgccct gaaagatctg     1200
gcaccgcgtg ttttcctggg cggccagggc caggcccgg aagaggcacg ccgtctgggt      1260
gccgaataca tggaagacct gaaaggcctg gctgaagcgc tgtggctgcc gcgcggtccg     1320
gaaaaagaag caatcactag tgtcggatcc ggtctcctcg agcaccacca ccaccaccac     1380
```

<210> SEQ ID NO 6
<211> LENGTH: 460
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 6

Met Met Val Ser Lys Gly Glu Glu Asp Asn Met Ala Ile Ile Lys Glu
1               5                   10                  15

Phe Met Arg Phe Lys Val His Met Glu Gly Ser Val Asn Gly His Glu
            20                  25                  30

Phe Glu Ile Glu Gly Glu Gly Glu Gly Arg Pro Tyr Glu Gly Thr Gln
        35                  40                  45

Thr Ala Lys Leu Lys Val Thr Lys Gly Gly Pro Leu Pro Phe Ala Trp
    50                  55                  60

Asp Ile Leu Ser Pro Gln Phe Met Tyr Gly Ser Lys Ala Tyr Val Lys
65                  70                  75                  80

His Pro Ala Asp Ile Pro Asp Tyr Leu Lys Leu Ser Phe Pro Glu Gly
                85                  90                  95

Phe Lys Trp Glu Arg Val Met Asn Phe Glu Asp Gly Gly Val Val Thr
            100                 105                 110

Val Thr Gln Asp Ser Ser Leu Gln Asp Gly Glu Phe Ile Tyr Lys Val
        115                 120                 125

Lys Leu Arg Gly Thr Asn Phe Pro Ser Asp Gly Pro Val Met Gln Lys
    130                 135                 140

Lys Thr Met Gly Trp Glu Ala Ser Ser Glu Arg Met Tyr Pro Glu Asp
145                 150                 155                 160

```
Gly Ala Leu Lys Gly Glu Ile Lys Gln Arg Leu Lys Leu Lys Asp Gly
                165                 170                 175
Gly His Tyr Asp Ala Glu Val Lys Thr Thr Tyr Lys Ala Lys Lys Pro
            180                 185                 190
Val Gln Leu Pro Gly Ala Tyr Asn Val Asn Ile Lys Leu Asp Ile Thr
        195                 200                 205
Ser His Asn Glu Asp Tyr Thr Ile Val Glu Gln Tyr Glu Arg Ala Glu
    210                 215                 220
Gly Arg His Ser Thr Gly Gly Met Asp Glu Leu Tyr Lys Glu Leu Pro
225                 230                 235                 240
Glu Asp Leu Gly Thr Gly Leu Leu Glu Ala Leu Leu Arg Gly Asp Leu
                245                 250                 255
Ala Gly Ala Glu Ala Leu Phe Arg Arg Gly Leu Arg Phe Trp Gly Pro
            260                 265                 270
Glu Gly Val Leu Glu His Leu Leu Pro Val Leu Arg Glu Val Gly
        275                 280                 285
Glu Ala Trp His Arg Gly Glu Ile Gly Val Ala Glu Glu His Leu Ala
    290                 295                 300
Ser Thr Phe Leu Arg Ala Arg Leu Gln Glu Leu Leu Asp Leu Ala Gly
305                 310                 315                 320
Phe Pro Pro Gly Pro Pro Val Leu Val Thr Thr Pro Gly Glu Arg
                325                 330                 335
His Glu Ile Gly Ala Met Leu Ala Ala Tyr His Leu Arg Arg Lys Gly
            340                 345                 350
Val Pro Ala Leu Tyr Leu Gly Pro Asp Thr Pro Leu Pro Asp Leu Arg
        355                 360                 365
Ala Leu Ala Arg Arg Leu Gly Ala Gly Ala Val Val Leu Ser Ala Val
    370                 375                 380
Leu Ser Glu Pro Leu Arg Ala Leu Pro Asp Gly Ala Leu Lys Asp Leu
385                 390                 395                 400
Ala Pro Arg Val Phe Leu Gly Gly Gln Gly Ala Gly Pro Glu Glu Ala
                405                 410                 415
Arg Arg Leu Gly Ala Glu Tyr Met Glu Asp Leu Lys Gly Leu Ala Glu
            420                 425                 430
Ala Leu Trp Leu Pro Arg Gly Pro Glu Lys Glu Ala Ile Thr Ser Val
        435                 440                 445
Gly Ser Gly Leu Leu Glu His His His His His His
    450                 455                 460
```

<210> SEQ ID NO 7
<211> LENGTH: 687
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
atgaaaggca gcagccatca tcatcatcat cacgtcgacg cccatattgt catggttgat      60
gcatacaagc cgacgaagct cgacggccac ggcgtgggtg ttccgggcgt cggtgtgccg     120
ggtgtgggtg tgccgggcga aggtgtgccg ggcgtcggtg tgccgggtgt tggtgttccg     180
ggcgttggtg tgccgggcgt tggcgtgccg ggcgagggtg tgccgggcgt tggtgttccg     240
ggcgtgggtg tgccgggcgt gggcgtgccg ggcgtcggtg ttccgggcga gggtgtgccg     300
ggcgtaggtg tgccgggcgt tggtgagctc tatgcggtta ccggccgtgg tgatagtccg     360
```

```
gccagctctg ccccgatcgc cactagtgtg ccgggcgtcg gcgtgccggg cgtaggtgtt    420
ccgggcgagg gtgttccggg cgttggtgtg ccgggcgtcg gcgtgccggg cgtgggtgtt    480
ccgggcgtag gtgtgccggg cgagggtgtg ccgggcgtgg gcgtgccggg cgtaggtgtt    540
ccgggcgtag gtgttccggg cgtaggtgtt ccgggtgaag gcgtgccggg cgttggtgtg    600
ccgggtgtgg gcgtgccggg cgggctgctc gacgcccata ttgtcatggt tgatgcatac    660
aagccgacga agctcgagtg gaagaaa                                       687
```

```
<210> SEQ ID NO 8
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Gly Ser Ser His His His His His Val Asp Ala His Ile
1               5                   10                  15

Val Met Val Asp Ala Tyr Lys Pro Thr Lys Leu Asp Gly His Gly Val
            20                  25                  30

Gly Val Pro Gly Val Gly Val Pro Gly Val Gly Val Pro Gly Glu Gly
        35                  40                  45

Val Pro Gly Val Gly Val Pro Gly Val Gly Val Pro Gly Val Gly Val
    50                  55                  60

Pro Gly Val Gly Val Pro Gly Glu Gly Val Pro Gly Val Gly Val Pro
65                  70                  75                  80

Gly Val Gly Val Pro Gly Val Gly Val Pro Gly Val Gly Val Pro Gly
                85                  90                  95

Glu Gly Val Pro Gly Val Gly Val Pro Gly Val Gly Glu Leu Tyr Ala
            100                 105                 110

Val Thr Gly Arg Gly Asp Ser Pro Ala Ser Ser Ala Pro Ile Ala Thr
        115                 120                 125

Ser Val Pro Gly Val Gly Val Pro Gly Val Gly Val Pro Gly Glu Gly
    130                 135                 140

Val Pro Gly Val Gly Val Pro Gly Val Gly Val Pro Gly Val Gly Val
145                 150                 155                 160

Pro Gly Val Gly Val Pro Gly Glu Gly Val Pro Gly Val Gly Val Pro
                165                 170                 175

Gly Val Gly Val Pro Gly Val Gly Val Pro Gly Val Gly Val Pro Gly
            180                 185                 190

Glu Gly Val Pro Gly Val Gly Val Pro Gly Val Gly Val Pro Gly Gly
        195                 200                 205

Leu Leu Asp Ala His Ile Val Met Val Asp Ala Tyr Lys Pro Thr Lys
    210                 215                 220

Leu Glu Trp Lys Lys
225
```

```
<210> SEQ ID NO 9
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
```

```
atgaaaggca gcagccatca tcatcatcat cacgtcgacg cccatattgt catggttgat    60
gcatacaagc cgacgaagct cgacggccac ggcgtgggtg ttccgggcgt cggtgtgccg   120
ggtgtgggtg tgccgggcga aggtgtgccg ggcgtcggtg tgccgggtgt tggtgttccg   180
ggcgttggtg tgccgggcgt tggcgtgccg ggcgagggtg tgccgggcgt tggtgttccg   240
ggcgtgggtg tgccgggcgt gggcgtgccg ggcgtcggtg ttccgggcga gggtgtgccg   300
ggcgtaggtg tgccgggcgt tggtgagctc gcccatattg tcatggttga tgcatacaag   360
ccgacgaaga ctagtgtgcc gggcgtcggc gtgccgggcg taggtgttcc gggcgagggt   420
gttccgggcg ttggtgtgcc gggcgtcggc gtgccgggcg tgggtgttcc gggcgtaggt   480
gtgccgggcg agggtgtgcc gggcgtgggc gtgccgggcg taggtgttcc gggcgtaggt   540
gttccgggcg taggtgttcc gggtgaaggc gtgccgggcg ttggtgtgcc gggtgtgggc   600
gtgccgggcg gctgctcga cgcccatatt gtcatggttg atgcatacaa gccgacgaag   660
ctcgagtgga agaaa                                                   675
```

<210> SEQ ID NO 10
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Gly Ser Ser His His His His His Val Asp Ala His Ile
1               5                   10                  15

Val Met Val Asp Ala Tyr Lys Pro Thr Lys Leu Asp Gly His Gly Val
            20                  25                  30

Gly Val Pro Gly Val Gly Val Pro Gly Val Gly Val Pro Gly Glu Gly
        35                  40                  45

Val Pro Gly Val Gly Val Pro Gly Val Gly Val Pro Gly Val Gly Val
    50                  55                  60

Pro Gly Val Gly Val Pro Gly Glu Gly Val Pro Gly Val Gly Val Pro
65                  70                  75                  80

Gly Val Gly Val Pro Gly Val Gly Val Pro Gly Val Gly Val Pro Gly
                85                  90                  95

Glu Gly Val Pro Gly Val Gly Val Pro Gly Val Gly Glu Leu Ala His
            100                 105                 110

Ile Val Met Val Asp Ala Tyr Lys Pro Thr Lys Thr Ser Val Pro Gly
        115                 120                 125

Val Gly Val Pro Gly Val Gly Val Pro Gly Glu Gly Val Pro Gly Val
    130                 135                 140

Gly Val Pro Gly Val Gly Val Pro Gly Val Gly Val Pro Gly Val Gly
145                 150                 155                 160

Val Pro Gly Glu Gly Val Pro Gly Val Gly Val Pro Gly Val Gly Val
                165                 170                 175

Pro Gly Val Gly Val Pro Gly Val Gly Val Pro Gly Glu Gly Val Pro
            180                 185                 190

Gly Val Gly Val Pro Gly Val Gly Val Pro Gly Gly Leu Leu Asp Ala
        195                 200                 205

His Ile Val Met Val Asp Ala Tyr Lys Pro Thr Lys Leu Glu Trp Lys
    210                 215                 220

Lys
225

<210> SEQ ID NO 11
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgaaaggca gcagccatca tcatcatcat cacgtcgaca tcccaacgac cgaaaacctg      60
tattttcagg gcgccatggt tgataccta tcaggtttat caagtgagca aggtcagtcc     120
ggtgatatga caattgaaga agatagtgct acccatatta aattctcaaa acgtgatgag     180
gacggcaaag agttagctgg tgcaactatg gagttgcgtg attcatctgg taaaactatt     240
agtacatgga tttcagatgg acaagtgaaa gatttctacc tgtatccagg aaaatataca     300
tttgtcgaaa ccgcagcacc agacggttat gaggtagcaa ctgctattac ctttacagtt     360
aatgagcaag gtcaggttac tgtaaatggc aaagcaacta aaggtgacgc tcatattgac     420
ggtccgcaag gtatttgggg tcagctcgag gccacggcg tgggtgttcc gggcgtcggt     480
gtgccgggtg tgggtgtgcc gggcgaaggt gtgccgggcg tcggtgtgcc gggtgttggt     540
gttccgggcg ttggtgtgcc gggcgttggc gtgccgggcg agggtgtgcc gggcgttggt     600
gttccgggcg tgggtgtgcc gggcgtgggc gtgccgggcg tcggtgttcc gggcgagggt     660
gtgccgggcg taggtgtgcc gggcgttggt gagctctatg cggttaccgg ccgtggtgat     720
agtccggcca gctctgcccc gatcgccact agtgtgccgg gcgtcggcgt gccgggcgta     780
ggtgttccgg gcgagggtgt ccgggcgtt ggtgtgccgg gcgtcggcgt gccgggcgtg     840
ggtgttccgg gcgtaggtgt gccgggcgag ggtgtgccgg gcgtgggcgt gccgggcgta     900
ggtgttccgg gcgtaggtgt tccgggcgta ggtgttccgg gtgaaggcgt gccgggcgtt     960
ggtgtgccgg gtgtgggcgt gccgggcggg ctggtcgaca tcccaacgac cgaaaacctg    1020
tattttcagg gcgccatggt tgataccta tcaggtttat caagtgagca aggtcagtcc    1080
ggtgatatga caattgaaga agatagtgct acccatatta aattctcaaa acgtgatgag    1140
dacggcaaag agttagctgg tgcaactatg gagttgcgtg attcatctgg taaaactatt    1200
agtacatgga tttcagatgg acaagtgaaa gatttctacc tgtatccagg aaaatataca    1260
tttgtcgaaa ccgcagcacc agacggttat gaggtagcaa ctgctattac ctttacagtt    1320
aatgagcaag gtcaggttac tgtaaatggc aaagcaacta aaggtgacgc tcatattgac    1380
ggtccgcaag gtatttgggg tcagctcgag tggaagaaa                           1419
```

<210> SEQ ID NO 12
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Lys Gly Ser Ser His His His His His Val Asp Ile Pro Thr
1               5                   10                  15

Thr Glu Asn Leu Tyr Phe Gln Gly Ala Met Val Asp Thr Leu Ser Gly
            20                  25                  30

Leu Ser Ser Glu Gln Gly Gln Ser Gly Asp Met Thr Ile Glu Glu Asp
```

```
                35                  40                  45
Ser Ala Thr His Ile Lys Phe Ser Lys Arg Asp Glu Asp Gly Lys Glu
 50                  55                  60

Leu Ala Gly Ala Thr Met Glu Leu Arg Asp Ser Ser Gly Lys Thr Ile
 65                  70                  75                  80

Ser Thr Trp Ile Ser Asp Gly Gln Val Lys Asp Phe Tyr Leu Tyr Pro
                 85                  90                  95

Gly Lys Tyr Thr Phe Val Glu Thr Ala Ala Pro Asp Gly Tyr Glu Val
                100                 105                 110

Ala Thr Ala Ile Thr Phe Thr Val Asn Glu Gln Gly Gln Val Thr Val
                115                 120                 125

Asn Gly Lys Ala Thr Lys Gly Asp Ala His Ile Asp Gly Pro Gln Gly
                130                 135                 140

Ile Trp Gly Gln Leu Asp Gly His Gly Val Gly Val Pro Gly Val Gly
145                 150                 155                 160

Val Pro Gly Val Gly Val Pro Gly Glu Gly Val Pro Gly Val Gly Val
                165                 170                 175

Pro Gly Val Gly Val Pro Gly Val Gly Val Pro Gly Val Gly Val Pro
                180                 185                 190

Gly Glu Gly Val Pro Gly Val Gly Val Pro Gly Val Gly Val Pro Gly
                195                 200                 205

Val Gly Val Pro Gly Val Gly Val Pro Gly Glu Gly Val Pro Gly Val
210                 215                 220

Gly Val Pro Gly Val Gly Glu Leu Tyr Ala Val Thr Gly Arg Gly Asp
225                 230                 235                 240

Ser Pro Ala Ser Ser Ala Pro Ile Ala Thr Ser Val Pro Gly Val Gly
                245                 250                 255

Val Pro Gly Val Gly Val Pro Gly Glu Gly Val Pro Gly Val Gly Val
                260                 265                 270

Pro Gly Val Gly Val Pro Gly Val Gly Val Pro Gly Val Gly Val Pro
                275                 280                 285

Gly Glu Gly Val Pro Gly Val Gly Val Pro Gly Val Gly Val Pro Gly
                290                 295                 300

Val Gly Val Pro Gly Val Gly Val Pro Gly Glu Gly Val Pro Gly Val
305                 310                 315                 320

Gly Val Pro Gly Val Gly Val Pro Gly Gly Leu Leu Asp Ile Pro Thr
                325                 330                 335

Thr Glu Asn Leu Tyr Phe Gln Gly Ala Met Val Asp Thr Leu Ser Gly
                340                 345                 350

Leu Ser Ser Glu Gln Gly Gln Ser Gly Asp Met Thr Ile Glu Glu Asp
                355                 360                 365

Ser Ala Thr His Ile Lys Phe Ser Lys Arg Asp Glu Asp Gly Lys Glu
                370                 375                 380

Leu Ala Gly Ala Thr Met Glu Leu Arg Asp Ser Ser Gly Lys Thr Ile
385                 390                 395                 400

Ser Thr Trp Ile Ser Asp Gly Gln Val Lys Asp Phe Tyr Leu Tyr Pro
                405                 410                 415

Gly Lys Tyr Thr Phe Val Glu Thr Ala Ala Pro Asp Gly Tyr Glu Val
                420                 425                 430

Ala Thr Ala Ile Thr Phe Thr Val Asn Glu Gln Gly Gln Val Thr Val
                435                 440                 445

Asn Gly Lys Ala Thr Lys Gly Asp Ala His Ile Asp Gly Pro Gln Gly
450                 455                 460
```

Ile Trp Gly Gln Leu Glu Trp Lys Lys
465                 470

<210> SEQ ID NO 13
<211> LENGTH: 4751
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| | | | | | |
|---|---|---|---|---|---|
| ctcgagaaat | cataaaaaat | ttatttgctt | tgtgagcgga | taacaattat | aatagattca | 60 |
| attgtgagcg | gataacaatt | tcacacagaa | ttcattaaag | aggagaaatt | aactatgaga | 120 |
| ggatcgcatc | accatcacca | tcacggatcc | gcatgcgagc | tcggtacccc | gggtcgacct | 180 |
| gcagccaagc | ttaattagct | gagcttggac | tcctgttgat | agatccagta | atgacctcag | 240 |
| aactccatct | ggatttgttc | agaacgctcg | gttgccgccg | ggcgtttttt | attggtgaga | 300 |
| atccaagcta | gcttggcgag | attttcagga | gctaaggaag | ctaaaatgga | gaaaaaaatc | 360 |
| actggatata | ccaccgttga | tatatcccaa | tggcatcgta | agaacatttt | tgaggcattt | 420 |
| cagtcagttg | ctcaatgtac | ctataaccag | accgttcagc | tggatattac | ggccttttta | 480 |
| aagaccgtaa | agaaaaataa | gcacaagttt | tatccggcct | ttattcacat | tcttgcccgc | 540 |
| ctgatgaatg | ctcatccgga | atttcgtatg | gcaatgaaag | acggtgagct | ggtgatatgg | 600 |
| gatagtgttc | acccttgtta | caccgttttc | catgagcaaa | ctgaaacgtt | ttcatcgctc | 660 |
| tggagtgaat | accacgacga | tttccggcag | tttctacaca | tatattcgca | agatgtggcg | 720 |
| tgttacggtg | aaaacctggc | ctatttccct | aaagggttta | ttgagaatat | gttttttcgtc | 780 |
| tcagccaatc | cctgggtgag | tttcaccagt | tttgatttaa | acgtggccaa | tatgacaac | 840 |
| ttcttcgccc | ccgttttcac | catgggcaaa | tattatacgc | aaggcgacaa | ggtgctgatg | 900 |
| ccgctggcga | ttcaggttca | tcatgccgtt | tgtgatggct | tccatgtcgg | cagaatgctt | 960 |
| aatgaattac | aacagtactg | cgatgagtgg | cagggcgggg | cgtaattttt | ttaaggcagt | 1020 |
| tattggtgcc | cttaaacgcc | tggggtaatg | actctctagc | ttgaggcatc | aaataaaacg | 1080 |
| aaaggctcag | tcgaaagact | gggcctttcg | ttttatctgt | tgtttgtcgg | tgaacgctct | 1140 |
| cctgagtagg | acaaatccgc | cctctagatt | acgtgcagtc | gatgataagc | tgtcaaacat | 1200 |
| gagaattgtg | cctaatgagt | gagctaactt | acattaattg | cgttgcgctc | actgcccgct | 1260 |
| ttccagtcgg | gaaacctgtc | gtgccagctg | cattaatgaa | tcggccaacg | cgcgggggaga | 1320 |
| gcggtttgc | gtattgggcg | ccagggtggt | ttttctttc | accagtgaga | cgggcaacag | 1380 |
| ctgattgccc | ttcaccgcct | ggccctgaga | gagttgcagc | aagcggtcca | cgctggtttg | 1440 |
| ccccagcagg | cgaaaatcct | gtttgatggt | ggttaacggc | gggatataac | atgagctgtc | 1500 |
| ttcggtatcg | tcgtatccca | ctaccgagat | atccgcacca | acgcgcagcc | cggactcggt | 1560 |
| aatggcgcgc | attgcgccca | gcgccatctg | atcgttggca | accagcatcg | cagtgggaac | 1620 |
| gatgccctca | ttcagcattt | gcatggtttg | ttgaaaaccg | gacatggcac | tccagtcgcc | 1680 |
| ttcccgttcc | gctatcggct | gaatttgatt | gcgagtgaga | tatttatgcc | agccagccag | 1740 |
| acgcagacgc | gccgagacag | aacttaatgg | gcccgctaac | agcgcgattt | gctggtgacc | 1800 |
| caatgcgacc | agatgctcca | cgcccagtcg | cgtaccgtct | tcatgggaga | aaataatact | 1860 |
| gttgatgggt | gtctggtcag | agacatcaag | aaataacgcc | ggaacattag | tgcaggcagc | 1920 |

```
ttccacagca atggcatcct ggtcatccag cggatagtta atgatcagcc cactgacgcg    1980
ttgcgcgaga agattgtgca ccgccgcttt acaggcttcg acgccgcttc gttctaccat    2040
cgacaccacc acgctggcac ccagttgatc ggcgcgagat ttaatcgccg cgacaatttg    2100
cgacggcgcg tgcagggcca gactggaggt ggcaacgcca atcagcaacg actgtttgcc    2160
cgccagttgt tgtgccacgc ggttgggaat gtaattcagc tccgccatcg ccgcttccac    2220
ttttccccgc gttttcgcag aaacgtggct ggcctggttc accacgcggg aaacggtctg    2280
ataagagaca ccggcatact ctgcgacatc gtataacgtt actggtttca cattcaccac    2340
cctgaattga ctctcttccg ggcgctatca tgccataccg cgaaaggttt tgcaccattc    2400
gatggtgtcg gaatttcggg cagcgttggg tcctggccac gggtgcgcat gatctagagc    2460
tgcctcgcgc gtttcggtga tgacggtgaa aacctctgac acatgcagct cccggagacg    2520
gtcacagctt gtctgtaagc ggatgccggg agcagacaag cccgtcaggg cgcgtcagcg    2580
ggtgttggcg ggtgtcgggg cgcagccatg acccagtcac gtagcgatag cggagtgtat    2640
actggcttaa ctatgcggca tcagagcaga ttgtactgag agtgcaccat atgcggtgtg    2700
aaataccgca cagatgcgta aggagaaaat accgcatcag cgctcttcc gcttcctcgc     2760
tcactgactc gctgcgctcg tcgttcggc tgcggcgagc ggtatcagct cactcaaagg      2820
cggtaatacg gttatccaca gaatcagggg ataacgcagg aaagaacatg tgagcaaaag    2880
gccagcaaaa ggccaggaac cgtaaaaagg ccgcgttgct ggcgttttc cataggctcc     2940
gcccccctga cgagcatcac aaaaatcgac gctcaagtca gaggtggcga aacccgacag    3000
gactataaag ataccaggcg tttccccctg gaagctccct cgtgcgctct cctgttccga    3060
ccctgccgct taccggatac ctgtccgcct ttctcccttc gggaagcgtg cgctttctc     3120
atagctcacg ctgtaggtat ctcagttcgg tgtaggtcgt tcgctccaag ctgggctgtg    3180
tgcacgaacc ccccgttcag cccgaccgct gcgccttatc cggtaactat cgtcttgagt    3240
ccaacccggt aagacacgac ttatcgccac tggcagcagc cactggtaac aggattagca    3300
gagcgaggta tgtaggcggt gctacagagt tcttgaagtg gtggcctaac tacggctaca    3360
ctagaaggac agtatttggt atctgcgctc tgctgaagcc agttaccttc ggaaaaagag    3420
ttggtagctc ttgatccggc aaacaaacca ccgctggtag cggtggtttt tttgtttgca    3480
agcagcagat tacgcgcaga aaaaaaggat ctcaagaaga tcctttgatc ttttctacgg    3540
ggtctgacgc tcagtggaac gaaaactcac gttaagggat tttggtcatg agattatcaa    3600
aaaggatctt cacctagatc cttttaaatt aaaaatgaag ttttaaatca atctaaagta    3660
tatatgagta aacttggtct gacagttacc aatgcttaat cagtgaggca cctatctcag    3720
cgatctgtct atttcgttca tccatagttg cctgactccc cgtcgtgtag ataactacga    3780
tacgggaggg cttaccatct ggccccagtg ctgcaatgat accgcgagac ccacgctcac    3840
cggctccaga tttatcagca ataaaccagc cagccggaag ggccgagcgc agaagtggtc    3900
ctgcaacttt atccgcctcc atccagtcta ttaattgttg ccgggaagct agagtaagta    3960
gttcgccagt taatagtttg cgcaacgttg ttgccattgc tacaggcatc gtggtgtcac    4020
gctcgtcgtt tggtatggct tcattcagct ccggttccca acgatcaagg cgagttacat    4080
gatcccccat gttgtgcaaa aaagcggtta gctccttcgg tcctccgatc gttgtcagaa    4140
gtaagttggc cgcagtgtta tcactcatgg ttatggcagc actgcataat tctcttactg    4200
tcatgccatc cgtaagatgc ttttctgtga ctggtgagta ctcaaccaag tcattctgag    4260
aatagtgtat gcggcgaccg agttgctctt gcccggcgtc aatacgggat aataccgcgc    4320
```

```
cacatagcag aactttaaaa gtgctcatca ttggaaaacg ttcttcgggg cgaaaactct    4380
caaggatctt accgctgttg agatccagtt cgatgtaacc cactcgtgca cccaactgat    4440
cttcagcatc ttttactttc accagcgttt ctgggtgagc aaaaacagga aggcaaaatg    4500
ccgcaaaaaa gggaataagg gcgacacgga aatgttgaat actcatactc ttcctttttc    4560
aatattattg aagcatttat cagggttatt gtctcatgag cggatacata tttgaatgta    4620
tttagaaaaa taaacaaata ggggttccgc gcacatttcc ccgaaaagtg ccacctgacg    4680
tctaagaaac cattattatc atgacattaa cctataaaaa taggcgtatc acgaggccct    4740
ttcgtcttca c                                                        4751

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcgagctcc cagaagatct                                                 20

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacactagtg attgcttctt tttccgga                                        28

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ataacatatg atggtgagca agggcgagg                                       29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caatgagctc cttgtacagc tcgtccatg                                       29

<210> SEQ ID NO 18
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (4)..(4)
<223> OTHER INFORMATION: Val or Glu
<220> FEATURE:
<221> NAME/KEY: MOD_RES
<222> LOCATION: (9)..(9)
<223> OTHER INFORMATION: Val or Glu
<220> FEATURE:
<221> NAME/KEY: MOD_RES
<222> LOCATION: (14)..(14)
<223> OTHER INFORMATION: Val or Glu
<220> FEATURE:
<221> NAME/KEY: MOD_RES
<222> LOCATION: (19)..(19)
<223> OTHER INFORMATION: Val or Glu
<220> FEATURE:
<221> NAME/KEY: MOD_RES
<222> LOCATION: (24)..(24)
<223> OTHER INFORMATION: Val or Glu
<220> FEATURE:
<221> NAME/KEY: MOD_RES
<222> LOCATION: (29)..(29)
<223> OTHER INFORMATION: Val or Glu
<220> FEATURE:
<221> NAME/KEY: MOD_RES
<222> LOCATION: (34)..(34)
<223> OTHER INFORMATION: Val or Glu
<220> FEATURE:
<221> NAME/KEY: MOD_RES
<222> LOCATION: (39)..(39)
<223> OTHER INFORMATION: Val or Glu
<220> FEATURE:
<221> NAME/KEY: MOD_RES
<222> LOCATION: (44)..(44)
<223> OTHER INFORMATION: Val or Glu
<220> FEATURE:
<221> NAME/KEY: MOD_RES
<222> LOCATION: (49)..(49)
<223> OTHER INFORMATION: Val or Glu
<220> FEATURE:
<221> NAME/KEY: MOD_RES
<222> LOCATION: (54)..(54)
<223> OTHER INFORMATION: Val or Glu
<220> FEATURE:
<221> NAME/KEY: MOD_RES
<222> LOCATION: (59)..(59)
<223> OTHER INFORMATION: Val or Glu
<220> FEATURE:
<221> NAME/KEY: MOD_RES
<222> LOCATION: (64)..(64)
<223> OTHER INFORMATION: Val or Glu
<220> FEATURE:
<221> NAME/KEY: MOD_RES
<222> LOCATION: (69)..(69)
<223> OTHER INFORMATION: Val or Glu
<220> FEATURE:
<221> NAME/KEY: MOD_RES
<222> LOCATION: (74)..(74)
<223> OTHER INFORMATION: Val or Glu
<220> FEATURE:
<221> NAME/KEY: MOD_RES
<222> LOCATION: (79)..(79)
<223> OTHER INFORMATION: Val or Glu
<220> FEATURE:
<221> NAME/KEY: MOD_RES
<222> LOCATION: (84)..(84)
<223> OTHER INFORMATION: Val or Glu
<220> FEATURE:
<221> NAME/KEY: MOD_RES
<222> LOCATION: (89)..(89)
<223> OTHER INFORMATION: Val or Glu
<220> FEATURE:
<221> NAME/KEY: MOD_RES
<222> LOCATION: (94)..(94)
<223> OTHER INFORMATION: Val or Glu
<220> FEATURE:
<221> NAME/KEY: MOD_RES
<222> LOCATION: (99)..(99)
<223> OTHER INFORMATION: Val or Glu
<220> FEATURE:
```

-continued

```
<221> NAME/KEY: MOD_RES
<222> LOCATION: (104)..(104)
<223> OTHER INFORMATION: Val or Glu
<220> FEATURE:
<221> NAME/KEY: MOD_RES
<222> LOCATION: (109)..(109)
<223> OTHER INFORMATION: Val or Glu
<220> FEATURE:
<221> NAME/KEY: MOD_RES
<222> LOCATION: (114)..(114)
<223> OTHER INFORMATION: Val or Glu
<220> FEATURE:
<221> NAME/KEY: MOD_RES
<222> LOCATION: (119)..(119)
<223> OTHER INFORMATION: Val or Glu
<220> FEATURE:
<221> NAME/KEY: MOD_RES
<222> LOCATION: (124)..(124)
<223> OTHER INFORMATION: Val or Glu
<220> FEATURE:
<221> NAME/KEY: MOD_RES
<222> LOCATION: (129)..(129)
<223> OTHER INFORMATION: Val or Glu
<220> FEATURE:
<221> NAME/KEY: MOD_RES
<222> LOCATION: (134)..(134)
<223> OTHER INFORMATION: Val or Glu
<220> FEATURE:
<221> NAME/KEY: MOD_RES
<222> LOCATION: (139)..(139)
<223> OTHER INFORMATION: Val or Glu
<220> FEATURE:
<221> NAME/KEY: MOD_RES
<222> LOCATION: (144)..(144)
<223> OTHER INFORMATION: Val or Glu
<220> FEATURE:
<221> NAME/KEY: MOD_RES
<222> LOCATION: (149)..(149)
<223> OTHER INFORMATION: Val or Glu
<220> FEATURE:
<221> NAME/KEY: MOD_RES
<222> LOCATION: (154)..(154)
<223> OTHER INFORMATION: Val or Glu
<220> FEATURE:
<221> NAME/KEY: MOD_RES
<222> LOCATION: (159)..(159)
<223> OTHER INFORMATION: Val or Glu
<220> FEATURE:
<221> NAME/KEY: MOD_RES
<222> LOCATION: (164)..(164)
<223> OTHER INFORMATION: Val or Glu
<220> FEATURE:
<221> NAME/KEY: MOD_RES
<222> LOCATION: (169)..(169)
<223> OTHER INFORMATION: Val or Glu
<220> FEATURE:
<221> NAME/KEY: MOD_RES
<222> LOCATION: (174)..(174)
<223> OTHER INFORMATION: Val or Glu
<220> FEATURE:
<221> NAME/KEY: MOD_RES
<222> LOCATION: (179)..(179)
<223> OTHER INFORMATION: Val or Glu
<220> FEATURE:
<221> NAME/KEY: MOD_RES
<222> LOCATION: (184)..(184)
<223> OTHER INFORMATION: Val or Glu
<220> FEATURE:
<221> NAME/KEY: MOD_RES
<222> LOCATION: (189)..(189)
<223> OTHER INFORMATION: Val or Glu
<220> FEATURE:
<221> NAME/KEY: MOD_RES
<222> LOCATION: (194)..(194)
<223> OTHER INFORMATION: Val or Glu
<220> FEATURE:
<221> NAME/KEY: MOD_RES
<222> LOCATION: (199)..(199)
<223> OTHER INFORMATION: Val or Glu
```

```
<220> FEATURE:
<221> NAME/KEY: MOD_RES
<222> LOCATION: (204)..(204)
<223> OTHER INFORMATION: Val or Glu
<220> FEATURE:
<221> NAME/KEY: MOD_RES
<222> LOCATION: (209)..(209)
<223> OTHER INFORMATION: Val or Glu
<220> FEATURE:
<221> NAME/KEY: MOD_RES
<222> LOCATION: (214)..(214)
<223> OTHER INFORMATION: Val or Glu
<220> FEATURE:
<221> NAME/KEY: MOD_RES
<222> LOCATION: (219)..(219)
<223> OTHER INFORMATION: Val or Glu
<220> FEATURE:
<221> NAME/KEY: MOD_RES
<222> LOCATION: (224)..(224)
<223> OTHER INFORMATION: Val or Glu
<220> FEATURE:
<221> NAME/KEY: MOD_RES
<222> LOCATION: (229)..(229)
<223> OTHER INFORMATION: Val or Glu
<220> FEATURE:
<221> NAME/KEY: MOD_RES
<222> LOCATION: (234)..(234)
<223> OTHER INFORMATION: Val or Glu
<220> FEATURE:
<221> NAME/KEY: MOD_RES
<222> LOCATION: (239)..(239)
<223> OTHER INFORMATION: Val or Glu
<220> FEATURE:
<221> NAME/KEY: MOD_RES
<222> LOCATION: (244)..(244)
<223> OTHER INFORMATION: Val or Glu
<220> FEATURE:
<221> NAME/KEY: MOD_RES
<222> LOCATION: (249)..(249)
<223> OTHER INFORMATION: Val or Glu
<220> FEATURE:
<221> NAME/KEY: MISC_FEATURE
<222> LOCATION: (1)..(250)
<223> OTHER INFORMATION: This sequence may encompass 1-50 "Val Pro Gly
      Xaa Gly" repeating units wherein Xaa is Val or Glu
<220> FEATURE:
<223> OTHER INFORMATION: See specification as filed for detailed
      description of substitutions and preferred embodiments

<400> SEQUENCE: 18

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
```

```
           145                 150                 155                 160
Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly
                245                 250

<210> SEQ ID NO 19
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Val or Glu
<220> FEATURE:
<221> NAME/KEY: MOD_RES
<222> LOCATION: (9)..(9)
<223> OTHER INFORMATION: Val or Glu
<220> FEATURE:
<221> NAME/KEY: MOD_RES
<222> LOCATION: (14)..(14)
<223> OTHER INFORMATION: Val or Glu
<220> FEATURE:
<221> NAME/KEY: MOD_RES
<222> LOCATION: (19)..(19)
<223> OTHER INFORMATION: Val or Glu
<220> FEATURE:
<221> NAME/KEY: MOD_RES
<222> LOCATION: (24)..(24)
<223> OTHER INFORMATION: Val or Glu
<220> FEATURE:
<221> NAME/KEY: MOD_RES
<222> LOCATION: (29)..(29)
<223> OTHER INFORMATION: Val or Glu
<220> FEATURE:
<221> NAME/KEY: MOD_RES
<222> LOCATION: (34)..(34)
<223> OTHER INFORMATION: Val or Glu
<220> FEATURE:
<221> NAME/KEY: MOD_RES
<222> LOCATION: (39)..(39)
<223> OTHER INFORMATION: Val or Glu
<220> FEATURE:
<221> NAME/KEY: MOD_RES
<222> LOCATION: (44)..(44)
<223> OTHER INFORMATION: Val or Glu
<220> FEATURE:
<221> NAME/KEY: MOD_RES
<222> LOCATION: (49)..(49)
<223> OTHER INFORMATION: Val or Glu
<220> FEATURE:
<221> NAME/KEY: MOD_RES
<222> LOCATION: (54)..(54)
<223> OTHER INFORMATION: Val or Glu
<220> FEATURE:
<221> NAME/KEY: MOD_RES
<222> LOCATION: (59)..(59)
<223> OTHER INFORMATION: Val or Glu
<220> FEATURE:
<221> NAME/KEY: MOD_RES
<222> LOCATION: (64)..(64)
```

```
<223> OTHER INFORMATION: Val or Glu
<220> FEATURE:
<221> NAME/KEY: MOD_RES
<222> LOCATION: (69)..(69)
<223> OTHER INFORMATION: Val or Glu
<220> FEATURE:
<221> NAME/KEY: MOD_RES
<222> LOCATION: (74)..(74)
<223> OTHER INFORMATION: Val or Glu
<220> FEATURE:
<221> NAME/KEY: MOD_RES
<222> LOCATION: (79)..(79)
<223> OTHER INFORMATION: Val or Glu
<220> FEATURE:
<221> NAME/KEY: MOD_RES
<222> LOCATION: (84)..(84)
<223> OTHER INFORMATION: Val or Glu
<220> FEATURE:
<221> NAME/KEY: MOD_RES
<222> LOCATION: (89)..(89)
<223> OTHER INFORMATION: Val or Glu
<220> FEATURE:
<221> NAME/KEY: MOD_RES
<222> LOCATION: (94)..(94)
<223> OTHER INFORMATION: Val or Glu
<220> FEATURE:
<221> NAME/KEY: MOD_RES
<222> LOCATION: (99)..(99)
<223> OTHER INFORMATION: Val or Glu
<220> FEATURE:
<221> NAME/KEY: MOD_RES
<222> LOCATION: (104)..(104)
<223> OTHER INFORMATION: Val or Glu
<220> FEATURE:
<221> NAME/KEY: MOD_RES
<222> LOCATION: (109)..(109)
<223> OTHER INFORMATION: Val or Glu
<220> FEATURE:
<221> NAME/KEY: MOD_RES
<222> LOCATION: (114)..(114)
<223> OTHER INFORMATION: Val or Glu
<220> FEATURE:
<221> NAME/KEY: MOD_RES
<222> LOCATION: (119)..(119)
<223> OTHER INFORMATION: Val or Glu
<220> FEATURE:
<221> NAME/KEY: MOD_RES
<222> LOCATION: (124)..(124)
<223> OTHER INFORMATION: Val or Glu
<220> FEATURE:
<221> NAME/KEY: MOD_RES
<222> LOCATION: (129)..(129)
<223> OTHER INFORMATION: Val or Glu
<220> FEATURE:
<221> NAME/KEY: MOD_RES
<222> LOCATION: (134)..(134)
<223> OTHER INFORMATION: Val or Glu
<220> FEATURE:
<221> NAME/KEY: MOD_RES
<222> LOCATION: (139)..(139)
<223> OTHER INFORMATION: Val or Glu
<220> FEATURE:
<221> NAME/KEY: MOD_RES
<222> LOCATION: (144)..(144)
<223> OTHER INFORMATION: Val or Glu
<220> FEATURE:
<221> NAME/KEY: MOD_RES
<222> LOCATION: (149)..(149)
<223> OTHER INFORMATION: Val or Glu
<220> FEATURE:
<221> NAME/KEY: MOD_RES
<222> LOCATION: (154)..(154)
<223> OTHER INFORMATION: Val or Glu
<220> FEATURE:
<221> NAME/KEY: MOD_RES
<222> LOCATION: (159)..(159)
<223> OTHER INFORMATION: Val or Glu
<220> FEATURE:
<221> NAME/KEY: MOD_RES
```

```
<222> LOCATION: (164)..(164)
<223> OTHER INFORMATION: Val or Glu
<220> FEATURE:
<221> NAME/KEY: MOD_RES
<222> LOCATION: (169)..(169)
<223> OTHER INFORMATION: Val or Glu
<220> FEATURE:
<221> NAME/KEY: MOD_RES
<222> LOCATION: (174)..(174)
<223> OTHER INFORMATION: Val or Glu
<220> FEATURE:
<221> NAME/KEY: MOD_RES
<222> LOCATION: (179)..(179)
<223> OTHER INFORMATION: Val or Glu
<220> FEATURE:
<221> NAME/KEY: MOD_RES
<222> LOCATION: (184)..(184)
<223> OTHER INFORMATION: Val or Glu
<220> FEATURE:
<221> NAME/KEY: MOD_RES
<222> LOCATION: (189)..(189)
<223> OTHER INFORMATION: Val or Glu
<220> FEATURE:
<221> NAME/KEY: MOD_RES
<222> LOCATION: (194)..(194)
<223> OTHER INFORMATION: Val or Glu
<220> FEATURE:
<221> NAME/KEY: MOD_RES
<222> LOCATION: (199)..(199)
<223> OTHER INFORMATION: Val or Glu
<220> FEATURE:
<221> NAME/KEY: MOD_RES
<222> LOCATION: (204)..(204)
<223> OTHER INFORMATION: Val or Glu
<220> FEATURE:
<221> NAME/KEY: MOD_RES
<222> LOCATION: (209)..(209)
<223> OTHER INFORMATION: Val or Glu
<220> FEATURE:
<221> NAME/KEY: MOD_RES
<222> LOCATION: (214)..(214)
<223> OTHER INFORMATION: Val or Glu
<220> FEATURE:
<221> NAME/KEY: MOD_RES
<222> LOCATION: (219)..(219)
<223> OTHER INFORMATION: Val or Glu
<220> FEATURE:
<221> NAME/KEY: MOD_RES
<222> LOCATION: (224)..(224)
<223> OTHER INFORMATION: Val or Glu
<220> FEATURE:
<221> NAME/KEY: MOD_RES
<222> LOCATION: (229)..(229)
<223> OTHER INFORMATION: Val or Glu
<220> FEATURE:
<221> NAME/KEY: MOD_RES
<222> LOCATION: (234)..(234)
<223> OTHER INFORMATION: Val or Glu
<220> FEATURE:
<221> NAME/KEY: MOD_RES
<222> LOCATION: (239)..(239)
<223> OTHER INFORMATION: Val or Glu
<220> FEATURE:
<221> NAME/KEY: MOD_RES
<222> LOCATION: (244)..(244)
<223> OTHER INFORMATION: Val or Glu
<220> FEATURE:
<221> NAME/KEY: MOD_RES
<222> LOCATION: (249)..(249)
<223> OTHER INFORMATION: Val or Glu
<220> FEATURE:
<221> NAME/KEY: MOD_RES
<222> LOCATION: (254)..(254)
<223> OTHER INFORMATION: Val or Glu
<220> FEATURE:
<221> NAME/KEY: MOD_RES
<222> LOCATION: (259)..(259)
<223> OTHER INFORMATION: Val or Glu
<220> FEATURE:
```

```
<221> NAME/KEY: MOD_RES
<222> LOCATION: (264)..(264)
<223> OTHER INFORMATION: Val or Glu
<220> FEATURE:
<221> NAME/KEY: MOD_RES
<222> LOCATION: (269)..(269)
<223> OTHER INFORMATION: Val or Glu
<220> FEATURE:
<221> NAME/KEY: MOD_RES
<222> LOCATION: (274)..(274)
<223> OTHER INFORMATION: Val or Glu
<220> FEATURE:
<221> NAME/KEY: MOD_RES
<222> LOCATION: (279)..(279)
<223> OTHER INFORMATION: Val or Glu
<220> FEATURE:
<221> NAME/KEY: MOD_RES
<222> LOCATION: (284)..(284)
<223> OTHER INFORMATION: Val or Glu
<220> FEATURE:
<221> NAME/KEY: MOD_RES
<222> LOCATION: (289)..(289)
<223> OTHER INFORMATION: Val or Glu
<220> FEATURE:
<221> NAME/KEY: MOD_RES
<222> LOCATION: (294)..(294)
<223> OTHER INFORMATION: Val or Glu
<220> FEATURE:
<221> NAME/KEY: MOD_RES
<222> LOCATION: (299)..(299)
<223> OTHER INFORMATION: Val or Glu
<220> FEATURE:
<221> NAME/KEY: MOD_RES
<222> LOCATION: (304)..(304)
<223> OTHER INFORMATION: Val or Glu
<220> FEATURE:
<221> NAME/KEY: MOD_RES
<222> LOCATION: (309)..(309)
<223> OTHER INFORMATION: Val or Glu
<220> FEATURE:
<221> NAME/KEY: MOD_RES
<222> LOCATION: (314)..(314)
<223> OTHER INFORMATION: Val or Glu
<220> FEATURE:
<221> NAME/KEY: MOD_RES
<222> LOCATION: (319)..(319)
<223> OTHER INFORMATION: Val or Glu
<220> FEATURE:
<221> NAME/KEY: MOD_RES
<222> LOCATION: (324)..(324)
<223> OTHER INFORMATION: Val or Glu
<220> FEATURE:
<221> NAME/KEY: MOD_RES
<222> LOCATION: (329)..(329)
<223> OTHER INFORMATION: Val or Glu
<220> FEATURE:
<221> NAME/KEY: MOD_RES
<222> LOCATION: (334)..(334)
<223> OTHER INFORMATION: Val or Glu
<220> FEATURE:
<221> NAME/KEY: MOD_RES
<222> LOCATION: (339)..(339)
<223> OTHER INFORMATION: Val or Glu
<220> FEATURE:
<221> NAME/KEY: MOD_RES
<222> LOCATION: (344)..(344)
<223> OTHER INFORMATION: Val or Glu
<220> FEATURE:
<221> NAME/KEY: MOD_RES
<222> LOCATION: (349)..(349)
<223> OTHER INFORMATION: Val or Glu
<220> FEATURE:
<221> NAME/KEY: MOD_RES
<222> LOCATION: (354)..(354)
<223> OTHER INFORMATION: Val or Glu
<220> FEATURE:
<221> NAME/KEY: MOD_RES
<222> LOCATION: (359)..(359)
<223> OTHER INFORMATION: Val or Glu
```

```
-continued

<220> FEATURE:
<221> NAME/KEY: MOD_RES
<222> LOCATION: (364)..(364)
<223> OTHER INFORMATION: Val or Glu
<220> FEATURE:
<221> NAME/KEY: MOD_RES
<222> LOCATION: (369)..(369)
<223> OTHER INFORMATION: Val or Glu
<220> FEATURE:
<221> NAME/KEY: MOD_RES
<222> LOCATION: (374)..(374)
<223> OTHER INFORMATION: Val or Glu
<220> FEATURE:
<221> NAME/KEY: MOD_RES
<222> LOCATION: (379)..(379)
<223> OTHER INFORMATION: Val or Glu
<220> FEATURE:
<221> NAME/KEY: MOD_RES
<222> LOCATION: (384)..(384)
<223> OTHER INFORMATION: Val or Glu
<220> FEATURE:
<221> NAME/KEY: MOD_RES
<222> LOCATION: (389)..(389)
<223> OTHER INFORMATION: Val or Glu
<220> FEATURE:
<221> NAME/KEY: MOD_RES
<222> LOCATION: (394)..(394)
<223> OTHER INFORMATION: Val or Glu
<220> FEATURE:
<221> NAME/KEY: MOD_RES
<222> LOCATION: (399)..(399)
<223> OTHER INFORMATION: Val or Glu
<220> FEATURE:
<221> NAME/KEY: MOD_RES
<222> LOCATION: (404)..(404)
<223> OTHER INFORMATION: Val or Glu
<220> FEATURE:
<221> NAME/KEY: MOD_RES
<222> LOCATION: (409)..(409)
<223> OTHER INFORMATION: Val or Glu
<220> FEATURE:
<221> NAME/KEY: MOD_RES
<222> LOCATION: (414)..(414)
<223> OTHER INFORMATION: Val or Glu
<220> FEATURE:
<221> NAME/KEY: MOD_RES
<222> LOCATION: (419)..(419)
<223> OTHER INFORMATION: Val or Glu
<220> FEATURE:
<221> NAME/KEY: MOD_RES
<222> LOCATION: (424)..(424)
<223> OTHER INFORMATION: Val or Glu
<220> FEATURE:
<221> NAME/KEY: MOD_RES
<222> LOCATION: (429)..(429)
<223> OTHER INFORMATION: Val or Glu
<220> FEATURE:
<221> NAME/KEY: MOD_RES
<222> LOCATION: (434)..(434)
<223> OTHER INFORMATION: Val or Glu
<220> FEATURE:
<221> NAME/KEY: MOD_RES
<222> LOCATION: (439)..(439)
<223> OTHER INFORMATION: Val or Glu
<220> FEATURE:
<221> NAME/KEY: MOD_RES
<222> LOCATION: (444)..(444)
<223> OTHER INFORMATION: Val or Glu
<220> FEATURE:
<221> NAME/KEY: MOD_RES
<222> LOCATION: (449)..(449)
<223> OTHER INFORMATION: Val or Glu
<220> FEATURE:
<221> NAME/KEY: MOD_RES
<222> LOCATION: (454)..(454)
<223> OTHER INFORMATION: Val or Glu
<220> FEATURE:
<221> NAME/KEY: MOD_RES
<222> LOCATION: (459)..(459)
```

<223> OTHER INFORMATION: Val or Glu
<220> FEATURE:
<221> NAME/KEY: MOD_RES
<222> LOCATION: (464)..(464)
<223> OTHER INFORMATION: Val or Glu
<220> FEATURE:
<221> NAME/KEY: MOD_RES
<222> LOCATION: (469)..(469)
<223> OTHER INFORMATION: Val or Glu
<220> FEATURE:
<221> NAME/KEY: MOD_RES
<222> LOCATION: (474)..(474)
<223> OTHER INFORMATION: Val or Glu
<220> FEATURE:
<221> NAME/KEY: MOD_RES
<222> LOCATION: (479)..(479)
<223> OTHER INFORMATION: Val or Glu
<220> FEATURE:
<221> NAME/KEY: MOD_RES
<222> LOCATION: (484)..(484)
<223> OTHER INFORMATION: Val or Glu
<220> FEATURE:
<221> NAME/KEY: MOD_RES
<222> LOCATION: (489)..(489)
<223> OTHER INFORMATION: Val or Glu
<220> FEATURE:
<221> NAME/KEY: MOD_RES
<222> LOCATION: (494)..(494)
<223> OTHER INFORMATION: Val or Glu
<220> FEATURE:
<221> NAME/KEY: MOD_RES
<222> LOCATION: (499)..(499)
<223> OTHER INFORMATION: Val or Glu
<220> FEATURE:
<221> NAME/KEY: MISC_FEATURE
<222> LOCATION: (1)..(500)
<223> OTHER INFORMATION: This sequence may encompass 1-100 "Val Pro Gly
    Xaa Gly" repeating units wherein Xaa is Val or Glu
<220> FEATURE:
<223> OTHER INFORMATION: See specification as filed for detailed
    description of substitutions and preferred embodiments

<400> SEQUENCE: 19

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

```
Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
        210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
            245                 250                 255

Pro Gly Xaa Gly Val Pro Gly Xaa Gly Val Pro Gly Xaa Gly Val Pro
                260                 265                 270

Gly Xaa Gly Val Pro Gly Xaa Gly Val Pro Gly Xaa Gly Val Pro Gly
        275                 280                 285

Xaa Gly Val Pro Gly Xaa Gly Val Pro Gly Xaa Gly Val Pro Gly Xaa
        290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
            325                 330                 335

Pro Gly Xaa Gly Val Pro Gly Xaa Gly Val Pro Gly Xaa Gly Val Pro
                340                 345                 350

Gly Xaa Gly Val Pro Gly Xaa Gly Val Pro Gly Xaa Gly Val Pro Gly
        355                 360                 365

Xaa Gly Val Pro Gly Xaa Gly Val Pro Gly Xaa Gly Val Pro Gly Xaa
        370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
            405                 410                 415

Pro Gly Xaa Gly Val Pro Gly Xaa Gly Val Pro Gly Xaa Gly Val Pro
                420                 425                 430

Gly Xaa Gly Val Pro Gly Xaa Gly Val Pro Gly Xaa Gly Val Pro Gly
        435                 440                 445

Xaa Gly Val Pro Gly Xaa Gly Val Pro Gly Xaa Gly Val Pro Gly Xaa
        450                 455                 460

Gly Val Pro Gly Xaa Gly Val Pro Gly Xaa Gly Val Pro Gly Xaa Gly
465                 470                 475                 480

Val Pro Gly Xaa Gly Val Pro Gly Xaa Gly Val Pro Gly Xaa Gly Val
            485                 490                 495

Pro Gly Xaa Gly
        500

<210> SEQ ID NO 20
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Val or Glu
<220> FEATURE:
<221> NAME/KEY: MOD_RES
<222> LOCATION: (9)..(9)
<223> OTHER INFORMATION: Val or Glu
<220> FEATURE:
<221> NAME/KEY: MOD_RES
```

```
<222> LOCATION: (14)..(14)
<223> OTHER INFORMATION: Val or Glu
<220> FEATURE:
<221> NAME/KEY: MOD_RES
<222> LOCATION: (19)..(19)
<223> OTHER INFORMATION: Val or Glu
<220> FEATURE:
<221> NAME/KEY: MOD_RES
<222> LOCATION: (24)..(24)
<223> OTHER INFORMATION: Val or Glu
<220> FEATURE:
<221> NAME/KEY: MOD_RES
<222> LOCATION: (29)..(29)
<223> OTHER INFORMATION: Val or Glu
<220> FEATURE:
<221> NAME/KEY: MOD_RES
<222> LOCATION: (34)..(34)
<223> OTHER INFORMATION: Val or Glu
<220> FEATURE:
<221> NAME/KEY: MOD_RES
<222> LOCATION: (39)..(39)
<223> OTHER INFORMATION: Val or Glu
<220> FEATURE:
<221> NAME/KEY: MOD_RES
<222> LOCATION: (44)..(44)
<223> OTHER INFORMATION: Val or Glu
<220> FEATURE:
<221> NAME/KEY: MOD_RES
<222> LOCATION: (49)..(49)
<223> OTHER INFORMATION: Val or Glu
<220> FEATURE:
<221> NAME/KEY: MOD_RES
<222> LOCATION: (54)..(54)
<223> OTHER INFORMATION: Val or Glu
<220> FEATURE:
<221> NAME/KEY: MOD_RES
<222> LOCATION: (59)..(59)
<223> OTHER INFORMATION: Val or Glu
<220> FEATURE:
<221> NAME/KEY: MOD_RES
<222> LOCATION: (64)..(64)
<223> OTHER INFORMATION: Val or Glu
<220> FEATURE:
<221> NAME/KEY: MOD_RES
<222> LOCATION: (69)..(69)
<223> OTHER INFORMATION: Val or Glu
<220> FEATURE:
<221> NAME/KEY: MOD_RES
<222> LOCATION: (74)..(74)
<223> OTHER INFORMATION: Val or Glu
<220> FEATURE:
<223> OTHER INFORMATION: See specification as filed for detailed
      description of substitutions and preferred embodiments

<400> SEQUENCE: 20

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly
65                  70                  75

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Trp Ser His Pro Gln Phe Glu Lys
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Val or Glu
<220> FEATURE:
<223> OTHER INFORMATION: See specification as filed for detailed
      description of substitutions and preferred embodiments

<400> SEQUENCE: 22

Val Pro Gly Xaa Gly
1               5

<210> SEQ ID NO 23
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Val or Glu
<220> FEATURE:
<221> NAME/KEY: MOD_RES
<222> LOCATION: (9)..(9)
<223> OTHER INFORMATION: Val or Glu
<220> FEATURE:
<221> NAME/KEY: MOD_RES
<222> LOCATION: (14)..(14)
<223> OTHER INFORMATION: Val or Glu
<220> FEATURE:
<221> NAME/KEY: MOD_RES
<222> LOCATION: (19)..(19)
<223> OTHER INFORMATION: Val or Glu
<220> FEATURE:
<221> NAME/KEY: MOD_RES
<222> LOCATION: (24)..(24)
<223> OTHER INFORMATION: Val or Glu
<220> FEATURE:
<221> NAME/KEY: MOD_RES
<222> LOCATION: (29)..(29)
<223> OTHER INFORMATION: Val or Glu
<220> FEATURE:
<221> NAME/KEY: MOD_RES
<222> LOCATION: (34)..(34)
<223> OTHER INFORMATION: Val or Glu
<220> FEATURE:
<221> NAME/KEY: MOD_RES
<222> LOCATION: (39)..(39)
<223> OTHER INFORMATION: Val or Glu
<220> FEATURE:
<221> NAME/KEY: MOD_RES
<222> LOCATION: (44)..(44)
<223> OTHER INFORMATION: Val or Glu
<220> FEATURE:
<221> NAME/KEY: MOD_RES
<222> LOCATION: (49)..(49)
<223> OTHER INFORMATION: Val or Glu
<220> FEATURE:
<221> NAME/KEY: MOD_RES
<222> LOCATION: (54)..(54)
<223> OTHER INFORMATION: Val or Glu
```

```
<220> FEATURE:
<221> NAME/KEY: MOD_RES
<222> LOCATION: (59)..(59)
<223> OTHER INFORMATION: Val or Glu
<220> FEATURE:
<221> NAME/KEY: MOD_RES
<222> LOCATION: (64)..(64)
<223> OTHER INFORMATION: Val or Glu
<220> FEATURE:
<221> NAME/KEY: MOD_RES
<222> LOCATION: (69)..(69)
<223> OTHER INFORMATION: Val or Glu
<220> FEATURE:
<221> NAME/KEY: MOD_RES
<222> LOCATION: (74)..(74)
<223> OTHER INFORMATION: Val or Glu
<220> FEATURE:
<221> NAME/KEY: MOD_RES
<222> LOCATION: (79)..(79)
<223> OTHER INFORMATION: Val or Glu
<220> FEATURE:
<221> NAME/KEY: MOD_RES
<222> LOCATION: (84)..(84)
<223> OTHER INFORMATION: Val or Glu
<220> FEATURE:
<221> NAME/KEY: MOD_RES
<222> LOCATION: (89)..(89)
<223> OTHER INFORMATION: Val or Glu
<220> FEATURE:
<221> NAME/KEY: MOD_RES
<222> LOCATION: (94)..(94)
<223> OTHER INFORMATION: Val or Glu
<220> FEATURE:
<221> NAME/KEY: MOD_RES
<222> LOCATION: (99)..(99)
<223> OTHER INFORMATION: Val or Glu
<220> FEATURE:
<221> NAME/KEY: MOD_RES
<222> LOCATION: (104)..(104)
<223> OTHER INFORMATION: Val or Glu
<220> FEATURE:
<221> NAME/KEY: MOD_RES
<222> LOCATION: (109)..(109)
<223> OTHER INFORMATION: Val or Glu
<220> FEATURE:
<221> NAME/KEY: MOD_RES
<222> LOCATION: (114)..(114)
<223> OTHER INFORMATION: Val or Glu
<220> FEATURE:
<221> NAME/KEY: MOD_RES
<222> LOCATION: (119)..(119)
<223> OTHER INFORMATION: Val or Glu
<220> FEATURE:
<221> NAME/KEY: MOD_RES
<222> LOCATION: (124)..(124)
<223> OTHER INFORMATION: Val or Glu
<220> FEATURE:
<221> NAME/KEY: MISC_FEATURE
<222> LOCATION: (1)..(125)
<223> OTHER INFORMATION: This sequence may encompass 2-25 "Val Pro Gly
     Xaa Gly" repeating units wherein Xaa is Val or Glu
<220> FEATURE:
<223> OTHER INFORMATION: See specification as filed for detailed
     description of substitutions and preferred embodiments

<400> SEQUENCE: 23

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60
```

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
            85                  90                  95

Pro Gly Xaa Gly Val Pro Gly Xaa Gly Val Pro Gly Xaa Gly Val Pro
        100                 105                 110

Gly Xaa Gly Val Pro Gly Xaa Gly Val Pro Gly Xaa Gly
    115                 120                 125

```
<210> SEQ ID NO 24
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Val or Glu
<220> FEATURE:
<221> NAME/KEY: MOD_RES
<222> LOCATION: (9)..(9)
<223> OTHER INFORMATION: Val or Glu
<220> FEATURE:
<221> NAME/KEY: MOD_RES
<222> LOCATION: (14)..(14)
<223> OTHER INFORMATION: Val or Glu
<220> FEATURE:
<221> NAME/KEY: MOD_RES
<222> LOCATION: (19)..(19)
<223> OTHER INFORMATION: Val or Glu
<220> FEATURE:
<221> NAME/KEY: MOD_RES
<222> LOCATION: (24)..(24)
<223> OTHER INFORMATION: Val or Glu
<220> FEATURE:
<221> NAME/KEY: MOD_RES
<222> LOCATION: (29)..(29)
<223> OTHER INFORMATION: Val or Glu
<220> FEATURE:
<221> NAME/KEY: MOD_RES
<222> LOCATION: (34)..(34)
<223> OTHER INFORMATION: Val or Glu
<220> FEATURE:
<221> NAME/KEY: MOD_RES
<222> LOCATION: (39)..(39)
<223> OTHER INFORMATION: Val or Glu
<220> FEATURE:
<221> NAME/KEY: MOD_RES
<222> LOCATION: (44)..(44)
<223> OTHER INFORMATION: Val or Glu
<220> FEATURE:
<221> NAME/KEY: MOD_RES
<222> LOCATION: (49)..(49)
<223> OTHER INFORMATION: Val or Glu
<220> FEATURE:
<221> NAME/KEY: MOD_RES
<222> LOCATION: (54)..(54)
<223> OTHER INFORMATION: Val or Glu
<220> FEATURE:
<221> NAME/KEY: MOD_RES
<222> LOCATION: (59)..(59)
<223> OTHER INFORMATION: Val or Glu
<220> FEATURE:
<221> NAME/KEY: MOD_RES
<222> LOCATION: (64)..(64)
<223> OTHER INFORMATION: Val or Glu
<220> FEATURE:
<221> NAME/KEY: MOD_RES
<222> LOCATION: (69)..(69)
<223> OTHER INFORMATION: Val or Glu
```

```
<220> FEATURE:
<221> NAME/KEY: MOD_RES
<222> LOCATION: (74)..(74)
<223> OTHER INFORMATION: Val or Glu
<220> FEATURE:
<221> NAME/KEY: MOD_RES
<222> LOCATION: (79)..(79)
<223> OTHER INFORMATION: Val or Glu
<220> FEATURE:
<221> NAME/KEY: MOD_RES
<222> LOCATION: (84)..(84)
<223> OTHER INFORMATION: Val or Glu
<220> FEATURE:
<221> NAME/KEY: MOD_RES
<222> LOCATION: (89)..(89)
<223> OTHER INFORMATION: Val or Glu
<220> FEATURE:
<221> NAME/KEY: MOD_RES
<222> LOCATION: (94)..(94)
<223> OTHER INFORMATION: Val or Glu
<220> FEATURE:
<221> NAME/KEY: MOD_RES
<222> LOCATION: (99)..(99)
<223> OTHER INFORMATION: Val or Glu
<220> FEATURE:
<221> NAME/KEY: MOD_RES
<222> LOCATION: (104)..(104)
<223> OTHER INFORMATION: Val or Glu
<220> FEATURE:
<221> NAME/KEY: MOD_RES
<222> LOCATION: (109)..(109)
<223> OTHER INFORMATION: Val or Glu
<220> FEATURE:
<221> NAME/KEY: MOD_RES
<222> LOCATION: (114)..(114)
<223> OTHER INFORMATION: Val or Glu
<220> FEATURE:
<221> NAME/KEY: MOD_RES
<222> LOCATION: (119)..(119)
<223> OTHER INFORMATION: Val or Glu
<220> FEATURE:
<221> NAME/KEY: MOD_RES
<222> LOCATION: (124)..(124)
<223> OTHER INFORMATION: Val or Glu
<220> FEATURE:
<221> NAME/KEY: MISC_FEATURE
<222> LOCATION: (1)..(125)
<223> OTHER INFORMATION: This sequence may encompass 5-25 "Val Pro Gly
     Xaa Gly" repeating units wherein Xaa is Val or Glu
<220> FEATURE:
<223> OTHER INFORMATION: See specification as filed for detailed
     description of substitutions and preferred embodiments

<400> SEQUENCE: 24

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
            85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly
        115                 120                 125
```

```
<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5
```